(12) United States Patent
Arcot Desai et al.

(10) Patent No.: US 12,303,693 B2
(45) Date of Patent: May 20, 2025

(54) SYSTEMS AND METHODS FOR CONTROLLING OPERATION OF AN IMPLANTED NEUROSTIMULATION SYSTEM BASED ON A MAPPING OF EPISODE DURATIONS AND SEIZURE PROBABILITY BIOMARKERS

(71) Applicant: NeuroPace, Inc., Mountain View, CA (US)

(72) Inventors: Sharanya Arcot Desai, Sunnyvale, CA (US); David A. Greene, Fort Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 499 days.

(21) Appl. No.: 17/709,227

(22) Filed: Mar. 30, 2022

(65) Prior Publication Data

US 2022/0314002 A1    Oct. 6, 2022

Related U.S. Application Data

(60) Provisional application No. 63/312,429, filed on Feb. 22, 2022, provisional application No. 63/170,018, filed on Apr. 2, 2021.

(51) Int. Cl.
*A61N 1/36* (2006.01)
*A61B 5/00* (2006.01)
(Continued)

(52) U.S. Cl.
CPC ........ *A61N 1/36139* (2013.01); *A61B 5/0006* (2013.01); *A61B 5/0031* (2013.01);
(Continued)

(58) Field of Classification Search
None
See application file for complete search history.

(56) References Cited

U.S. PATENT DOCUMENTS 6,016,449 A * 1/2000 Fischell ............... A61B 5/4094
607/45
6,480,743 B1 * 11/2002 Kirkpatrick ........ A61N 1/36135
607/45
(Continued)

FOREIGN PATENT DOCUMENTS

WO    2016154298    9/2016

OTHER PUBLICATIONS

Shoeb et al., "Application of Machine Learning to Epileptic Seizure Detection", Appearing in the Proceedings of the 27th International Conference on Machine Learning, Haifa, Israel 2010, Copyright 2010.
(Continued)

*Primary Examiner* — Carl H Layno
*Assistant Examiner* — Manolis Pahakis
(74) *Attorney, Agent, or Firm* — LOZA & LOZA, LLP; David S. Sarisky

(57) ABSTRACT

An implanted neurostimulation system is configured to sense episodes of electrographic events and determine durations of episodes. Durations of electrographic events sensed by the implanted neurostimulation system are mapped with seizure probability biomarkers derived from records of the electrographic events to create a mapping function. A seizure probability biomarker that has a value desired for the operation of the implanted neurostimulation system is selected. The duration mapped to the selected seizure probability biomarker is identified and programmed into a control module of the implanted neurostimulation system as a programmed parameter that triggers the operation by the implanted neurostimulation system. The process may be
(Continued)

repeated for other operations of the implanted neurostimulation system.

19 Claims, 37 Drawing Sheets

(51) Int. Cl.
    *A61N 1/05*       (2006.01)
    *A61N 1/372*     (2006.01)
    *G06N 3/044*     (2023.01)
    *G06N 3/045*     (2023.01)
    *G06N 3/047*     (2023.01)
    *G06N 20/20*     (2019.01)
    *G16H 50/20*     (2018.01)

(52) U.S. Cl.
    CPC .......... *A61B 5/4064* (2013.01); *A61B 5/4094* (2013.01); *A61B 5/4848* (2013.01); *A61B 5/7267* (2013.01); *A61N 1/0526* (2013.01); *A61N 1/0529* (2013.01); *A61N 1/36064* (2013.01); *A61N 1/37247* (2013.01); *G06N 3/044* (2023.01); *G06N 3/045* (2023.01); *G06N 3/047* (2023.01); *G06N 20/20* (2019.01); *G16H 50/20* (2018.01)

(56) References Cited

U.S. PATENT DOCUMENTS

| | | | |
|---|---|---|---|
| 6,594,524 B2 * | 7/2003 | Esteller | G16H 20/70 607/45 |
| 6,810,285 B2 | 10/2004 | Pless et al. | |
| 7,209,787 B2 | 4/2007 | Dilorenzo | |
| 7,231,254 B2 | 6/2007 | Dilorenzo | |
| 7,242,984 B2 | 7/2007 | Dilorenzo | |
| 7,277,758 B2 | 10/2007 | Dilorenzo | |
| 7,280,867 B2 * | 10/2007 | Frei | A61N 1/36082 600/545 |
| 7,324,851 B1 | 1/2008 | Dilorenzo | |
| 7,403,820 B2 | 7/2008 | Dilorenzo | |
| 7,529,582 B1 | 5/2009 | Dilorenzo | |
| 7,542,803 B2 | 6/2009 | Heruth et al. | |
| 7,599,736 B2 | 10/2009 | Dilorenzo | |
| 7,623,928 B2 | 11/2009 | Dilorenzo | |
| 7,676,273 B2 | 3/2010 | Goetz et al. | |
| 7,747,325 B2 | 6/2010 | Dilorenzo | |
| 7,822,481 B2 | 10/2010 | Gerber et al. | |
| 7,853,322 B2 | 12/2010 | Bourget et al. | |
| 7,853,329 B2 | 12/2010 | Dilorenzo | |
| 7,894,903 B2 | 2/2011 | John | |
| 7,899,545 B2 | 3/2011 | John | |
| 7,930,035 B2 | 4/2011 | Dilorenzo | |
| 7,957,797 B2 | 6/2011 | Bourget et al. | |
| 7,957,809 B2 | 6/2011 | Bourget et al. | |
| 7,966,073 B2 | 6/2011 | Pless et al. | |
| 7,974,696 B1 | 7/2011 | Dilorenzo | |
| 7,976,465 B2 * | 7/2011 | Frei | A61N 1/3614 600/301 |
| 8,027,730 B2 | 9/2011 | John | |
| 8,126,567 B2 | 2/2012 | Gerber et al. | |
| 8,376,943 B2 * | 2/2013 | Kovach | A61B 5/4094 607/45 |
| 8,478,417 B2 * | 7/2013 | Drew | A61B 5/686 607/59 |
| 8,543,214 B2 | 9/2013 | Osorio et al. | |
| 8,543,217 B2 | 9/2013 | Stone et al. | |
| 8,694,115 B2 | 4/2014 | Goetz et al. | |
| 8,706,237 B2 | 4/2014 | Giftakis et al. | |
| 8,731,656 B2 | 5/2014 | Bourget et al. | |
| 8,903,486 B2 | 12/2014 | Bourget et al. | |
| 9,931,508 B2 | 4/2018 | Burdick et al. | |
| 9,955,921 B2 * | 5/2018 | Esteller | A61B 5/37 |
| 10,123,717 B2 | 11/2018 | Tcheng | |
| 10,252,056 B2 | 4/2019 | Mogul | |
| 10,448,877 B2 * | 10/2019 | Truccolo | A61B 5/375 |
| 10,729,907 B2 | 8/2020 | Desai et al. | |
| 10,993,652 B2 * | 5/2021 | Osorio | A61B 5/0205 |
| 2002/0103512 A1 * | 8/2002 | Echauz | A61B 5/375 607/9 |
| 2003/0018367 A1 | 1/2003 | Dilorenzo | |
| 2003/0171789 A1 | 9/2003 | Malek et al. | |
| 2004/0199217 A1 | 10/2004 | Lee et al. | |
| 2004/0199218 A1 | 10/2004 | Lee et al. | |
| 2004/0215286 A1 | 10/2004 | Stypulkowski | |
| 2004/0267330 A1 | 12/2004 | Lee et al. | |
| 2005/0021103 A1 | 1/2005 | Dilorenzo | |
| 2005/0021104 A1 | 1/2005 | Dilorenzo | |
| 2005/0060007 A1 | 3/2005 | Goetz | |
| 2005/0060008 A1 | 3/2005 | Goetz | |
| 2005/0197590 A1 * | 9/2005 | Osorio | A61B 5/4094 600/544 |
| 2006/0111644 A1 * | 5/2006 | Guttag | A61B 5/7267 600/544 |
| 2006/0265022 A1 | 11/2006 | John et al. | |
| 2007/0073355 A1 | 3/2007 | Dilorenzo | |
| 2007/0142862 A1 | 6/2007 | Dilorenzo | |
| 2007/0142874 A1 * | 6/2007 | John | A61N 2/006 607/45 |
| 2007/0162086 A1 | 7/2007 | Dilorenzo | |
| 2007/0167991 A1 | 7/2007 | Dilorenzo | |
| 2007/0208212 A1 | 9/2007 | Dilorenzo | |
| 2007/0213786 A1 * | 9/2007 | Sackellares | A61B 5/369 607/45 |
| 2007/0287931 A1 | 12/2007 | Dilorenzo | |
| 2008/0058773 A1 | 3/2008 | John | |
| 2008/0061961 A1 | 3/2008 | John | |
| 2008/0071314 A1 | 3/2008 | John | |
| 2008/0109005 A1 | 5/2008 | Trudeau et al. | |
| 2008/0119900 A1 | 5/2008 | Dilorenzo | |
| 2008/0269631 A1 * | 10/2008 | Denison | A61B 5/4839 600/544 |
| 2009/0018609 A1 | 1/2009 | Dilorenzo | |
| 2010/0023089 A1 | 1/2010 | Dilorenzo | |
| 2010/0217348 A1 | 8/2010 | Dilorenzo | |
| 2010/0241183 A1 | 9/2010 | Dilorenzo | |
| 2010/0249859 A1 | 9/2010 | Dilorenzo | |
| 2010/0292602 A1 * | 11/2010 | Worrell | A61B 5/377 607/45 |
| 2011/0040353 A1 | 2/2011 | Gerber et al. | |
| 2011/0307030 A1 | 12/2011 | John | |
| 2012/0245481 A1 * | 9/2012 | Blanco | A61B 5/4094 600/544 |
| 2012/0265262 A1 * | 10/2012 | Osorio | A61N 1/36114 607/45 |
| 2013/0096840 A1 * | 4/2013 | Osorio | A61B 5/0205 702/19 |
| 2013/0345526 A1 * | 12/2013 | Osorio | A61B 5/4094 600/309 |
| 2014/0148723 A1 * | 5/2014 | Nierenberg | A61B 5/7203 600/544 |
| 2015/0005592 A1 * | 1/2015 | Osorio | A61B 5/02055 607/45 |
| 2015/0080670 A1 * | 3/2015 | Osorio | A61B 5/0826 600/509 |
| 2016/0228705 A1 * | 8/2016 | Crowder | A61N 1/36064 |
| 2016/0310070 A1 * | 10/2016 | Sabesan | A61B 5/686 |
| 2017/0095194 A1 * | 4/2017 | Krauss | G16H 40/67 |
| 2017/0196497 A1 * | 7/2017 | Ray | G06N 7/01 |
| 2017/0265764 A1 * | 9/2017 | Osorio | A61N 1/0534 |
| 2019/0117978 A1 | 4/2019 | Desai et al. | |
| 2019/0150774 A1 * | 5/2019 | Brinkmann | A61B 5/0006 |
| 2019/0246990 A1 * | 8/2019 | Karoly | A61B 5/7267 |
| 2019/0274566 A1 * | 9/2019 | Wilson | A61B 5/4094 |
| 2020/0129111 A1 * | 4/2020 | Osorio | A61B 5/00 |
| 2020/0194120 A1 * | 6/2020 | Kabrams | A61B 5/7221 |
| 2020/0272857 A1 | 8/2020 | Desai et al. | |
| 2021/0282701 A1 * | 9/2021 | Chan | A61B 5/37 |
| 2021/0369181 A1 * | 12/2021 | Nierenberg | G16H 50/50 |
| 2021/0369183 A1 * | 12/2021 | Osorio | A61B 5/1118 |

(56) References Cited

U.S. PATENT DOCUMENTS

2022/0095994 A1* 3/2022 Osorio .................. A61B 5/024
2022/0180993 A1* 6/2022 Kuperman ............. G16H 40/63

OTHER PUBLICATIONS

Spencer et al., "Morphological patterns of seizures recorded intracranially," 33:537-545 (1992).
Lee et al., "Intracranial EEG seizure-onset patterns in neocortical epilepsy," 41:297-307 (2000).
Langan et al., "Case-control study of SUDEP, " Neurology,64:1131-1133 (2005).
Bateman et al., "Serotonin reuptake inhibitors are associated with reduced severity of ictal hypoxemia in medically refractory partial epilepsy," 51:2211-2214 (2010).
Shoeb, Thesis "Application of Machine Learning to Epileptic Seizure Onset Detection and Treatment", Submitted to Harvard-MIT Div. of Health Sciences re Dr. of Philosophy in EE and Med Engineering at MIT, Sep. 2009.
D'Alessandro et al., "A multi-feature and multi-channel univariate selection process for seizure prediction", Clinical Neurophysiology 116 (2005) 506-516.
Conradsen et al., "Automated algorithm for generalised tonic-clonic epileptic seizure onset detection based on sEMG zero-crossing rate", IEEE Transactions On Biomedical Engineering, Copyright IEEE 2011, pubs-permissions@ieee.org.
Kharbouch et al., "An algorithm for seizure onset detection using intracranial EEG," Epilepsy Balmy. Dec. 2011, 22(01): S29-S35.
Khan et al., "Automatic Detection Of Seizure Onset In Pediatric EEG", International Journal of Embedded Systems and Applications (IJESA) vol. 2, No. 3, Sep. 2012.
Zhang et al., "An automatic patient-specific seizure onset detection method in intracranial EEG based on incremental nonlinear dimensionality reduction", Computers in Biology and Medicine 40 (2010) 889-899. Automated Detection and Quantitative Analysis of Seizures and Short-Term Prediction of Clinical Onset, Epilepsia, 39(6):615-627 (1998).
Gabor et al., "Automated Seizure Detection Using A Self-Organizing Neural Network", Dept. of Neurology, University of CA, Davis Medical Center, Jan. 5, 1996; Published Apr. 15, 1996, Electroencephalography and Clinical Neurophysiology 99 (1996) 257-266.
Gabor, "Seizure Detection Using A Self-Organizing Neural Network: Validation and Comparison with Other Detection Strategies", Dept. of Neurology, University of CA, Davis Medical Center, Accepted for Publication Feb. 28, 1998, Electroencephalography and Clinical Neurophysiology 107 (1998) 27-32.
Russakovsky et al., "ImageNet Large Scale Visual Recognition Challenge", International Journal of Computer Vision, available online Apr. 11, 2015, published Dec. 2015; vol. 115, Issue 3, DOI 10.1007/s11263-015-0816-; pp. 211-252.
Lecun et al., "Deep Learning", Nature, May 27, 2015, vol. 521; DOI: 10.1038/nature 14539; pp. 436-444.
Xu et al., "Survey of Clustering Algorithms", IEEE Transactions on Neural Networks, vol. 16, No. 3, May 1, 2005; 35 pages.
Krizhevsky et al., "ImageNet Classification with Deep Convolutional Neural Networks", NIPS'12 Proceedings of the 25th International Conference on Neural Information Processing Systems—vol. 1, pp. 1097-1105, Dec. 3, 2012.
Desai, "Insights from mining large-scale human EcoG data", ICTAL2017, The Penumbra Conference, presented Aug. 21, 2017; 9 pages.
Esteva et al. "Dermatologist level classification of skin cancer with deep neural networks", Nature, vol. 542, published Feb. 2, 2017, pp. 115-118.
Desai et al., "Transfer-learning for differentiating epileptic patients who respond to treatment based on chronic ambulatory ECoG data," in 2019 9th International IEEE/EMBS Conference on Neural Engineering (NER), 2019: IEEE, pp. 1-4.
Hussein et al., "Epileptic Seizure Detection: A Deep Learning Approach", ArXiv:1803.09848v1, Mar. 27, 2018, pp. 1-12; 2018.
Tsiouris et al., "A Long Short-Term Memory deep learning network for the prediction of epileptic seizures using EEG signals", Computers in Biology and Medicine, vol. 99, Aug. 1, 2018, pp. 24-37.
Thodoroff et al., "Learning Robust Features using Deep Learning for Automatic Seizure Detection", ArXiv:1608.00220, Jul. 31, 2016, pp. 1-12.
Pailla et al., "Autoencoders for learning template spectrograms in electrocorticographic signals", Journal of Neural Engineering, vol. 16, No. 1, Jan. 14, 2019.
Ling et al., "Waveform Modeling and Generation Using Hierarchical Recurrent Neural Networks for Speech Bandwidth Extension", IEEE/ACM Transactions on Audio, Speech, and Language Processing, vol. 26, No. 5, pp. 883-894, May 2018.
Zeiler et al., "Visualizing and Understanding Convolutional Networks", ArXiv:1311.2901v3, Nov. 28, 2013, pp. 1-11.
Barry et al., "A High Accuracy Electrographic Seizure Classifier Trained Using Semi-Supervised Labeling Applied to a Large Spectrogram Dataset." Frontiers in Neuroscience, vol. 15, pp. 1-20, (Jun. 28, 2021).
Baud et al., "Multi-day rhythms modulate seizure risk in epilepsy." Nat Commun 9, 88, (2018).
Brinkmann et al., "Forecasting Seizures Using Intracranial EEG Measures and SVM in Naturally Occurring Canine Epilepsy," G. A. PLoS.One., 10:e0133900 (2015).
Cantero et al., "Sleep-dependent theta oscillations in the human hippocampus and neocortex,", J Neurosci,23:10897-10903 (2003).
Carrington et al.,"Effect of focal low-frequency stimulation on amygdala-kindled afterdischarge thresholds and seizure profiles in fast- and slow-kindling rat strains," Epilepsia, 48:1604-1613 (2007).
Chan et al., "Automated seizure onset detection for accurate onset time determination in intracranial EEG," Clin. Neurophysiol., 119:2687-2696 (2008).
Colom, "Septal networks: relevance to theta rhythm, epilepsy and Alzheimer's disease," J Neurochem., 96:609-623 (2006).
Crespel et al., "Sleep influence on seizures and epilepsy effects on sleep in partial frontal and temporal lobe epilepsies," M. Clin. Neurophysiol., 111 Suppl 2:S54-S59 (2000).
Desai et al., "Deep Learning for seizure classification and potential seizure biomarker discovery", Abstract, published online at www.aesnet.org on Nov. 20, 2017; 2 pages.
Desai et al., "Quantitative electrocorticographic biomarkers of clinical outcomes in mesial temporal lobe epileptic patients treated with the RNS system", Clinical Neurophysiology 130, 1364-1374, (2019).
García-Hernández et al., "Septo-hippocampal networks in chronic epilepsy", EAT Neurol. Mar. 2010; 222(1): 86-92.
Goodman et al., "Preemptive low-frequency stimulation decreases the incidence of amygdala-kindled seizures," Epilepsia,46:1-7 (2005).
Herman et al., "Distribution of partial seizures during the sleep—wake cycle: differences by seizure onset site," Neurology, 56:1453-1459 (2001).
Karoly et al., "The circadian profile of epilepsy improves seizure forecasting." Brain 140, 2169-2182, (2017).
Karoly et al., "Forecasting cycles of seizure likelihood". Epilepsia 61, 776-786, (Dec, 19, 2019).
Kisilev et al., "Medical Image Description Using Multi-task-loss CNN." Deep Learning and Data Labeling for Medical Applications. DLMIA Labels 2016 2016. Lecture Notes in Computer Science(), vol. 10008. Springer, Cham. https://doi.org/10.1007/978-3-319-46976-8_13.
Litt et al., "Epileptic Seizures May Begin Hours in Advance of Clinical Onset: A Report of Five Patients", Neuron, vol. 30, 51-64, Apr. 2001.
Logesparan et al., "Optimal features for online seizure detection", Medical & Biological Engineering & Computing, 50.7 (2012): 659-669, and Supplementary Material relating to article.
Lysyansky et al., "Optimal number of stimulation contacts for coordinated reset neuromodulation," Front Neuroeng.,6:5 (2013).
Malow, "The interaction between sleep and epilepsy," Epilepsia,48 Suppl 9:36-38 (2007).

(56) References Cited

OTHER PUBLICATIONS

Maturana et al., "Critical slowing down as a biomarker for seizure susceptibility". Nat Commun 11, 2172, (2020).

Meisel et al., "Intrinsic excitability measures track antiepileptic drug action and uncover increasing/ decreasing excitability over the wake/sleep cycle". Proc Natl Acad Sci U S A 112, 14694-14699, (Nov. 6, 2015).

Miller et al., "Anticonvulsant effects of the experimental induction of hippocampal theta activity," Epilepsy Res., 18:195-204 (1994).

Minecan et al., "Relationship of epileptic seizures to sleep stage and sleep depth," Sleep, 25:899-904 (2002).

Ng et al., "Why are seizures rare in rapid eye movement sleep? Review of the frequency of seizures in different sleep stages, " M. Epilepsy Res. Treat.,2013:932790 (2013).

Ogren et al., "Three-dimensional hippocampal atrophy maps distinguish two common temporal lobe seizure-onset patterns," Epilepsia, 50(6):1361-1370 (2009).

Osorio et al., "Real-Time Automated Detection and Quantitative Analysis of Seizures and Short-Term Prediction of Clinical Onset", Epilepsia, 39(6):615-627 (1998).

Perucca et al., "Intracranial electroencephalographic seizure-onset patterns: effect of underlying pathology," J. Brain: 137:183-196 (2014).

Popovych et al., "Desynchronizing electrical and sensory coordinated reset neuromodulation", Frontiers in Human Neuroscience, Mar. 20, 2012, vol. 6, Article 58.

Quigg et al., Electrocorticographic events from long-term ambulatory brain recordings can potentially supplement seizure diaries. Epilepsy Res 161, 106302, (2020).

Schiller et al., "Characterization and comparison of local onset and remote propagated electrographic seizures recorded with intracranial electrodes," Epilepsia, 39:380-388 (1998).

Si et al., "Fully end-to-end deep-learning-based diagnosis of pancreatic tumors". Theranostics 11, 1982, (2021).

Skarpaas et al., "Clinical and electrocorticographic response to antiepileptic drugs in patients treated with responsive stimulation", Epilepsy & Behavior 83, 192-200, (2018).

Tass et al., "Long-lasting desynchronization in rat hippocampal slice induced by coordinated reset stimulation", Physical Review F 80, 011902 (2009).

Tass et al., "Coordinated reset has sustained aftereffects in Parkinsonian monkeys," Ann.Neurol,72:816-820 (2012).

Uriguen et al., "Comparison of background EEG activity of different groups of patients with idiopathic epilepsy using Shannon spectral entropy and cluster-based permutation statistical testing". PLoS One 12, (Sep. 18, 2017).

Van Putten et al., "Detecting temporal lobe seizures from scalp EEG recordings: a comparison of various features," Clin.Neurophysiol., 116:2480-2489 (2005).

Vaswani et al., "Attention is all you need". Advances in Neural Information Processing Systems 30 (2017).

Wackermann, "Beyond mapping: estimating complexity of multi-channel EEG recordings, " Acta Neurobiol. Exp. (Wars.),56:197-208 (1996).

Welsh et al., "A circadian rhythm of hippocampal theta activity in the mouse," Physiol.Behav,35:533-538 (1985).

Gorospe et al., A Generalization Performance Study Using Deep Learning Networks in Embedded Systems. Sensors (Basel) 21, (2021).

\* cited by examiner

| Episode # | Date/Time | Duration | Pattern/Therapy Information |
|---|---|---|---|
| 353 | Fri, Feb 19, 2021 05:57:58 | 4.5 seconds | Pattern B2 Therapy Delivery Inhibited by Therapies Programmed Off; Episode End Redetection Counts: Pattern A1=0, Pattern B2=0 |
| 354 | Fri, Feb 19, 2021 05:58:10 | 4.5 seconds | Pattern B2 Therapy Delivery Inhibited by Therapies Programmed Off; Episode End Redetection Counts: Pattern A1=0, Pattern B2=0 |
| 355 | Fri, Feb 19, 2021 05:58:43 | 4.5 seconds | Pattern B2 Therapy Delivery Inhibited by Therapies Programmed Off; Episode End Redetection Counts: Pattern A1=0, Pattern B2=0 |
| 356 | Fri, Feb 19, 2021 06:05:41 | 4.5 seconds | Pattern B2 Therapy Delivery Inhibited by Therapies Programmed Off; Episode End Redetection Counts: Pattern A1=0, Pattern B2=0 |
| 357 | Fri, Feb 19, 2021 06:05:47 | 93.5 seconds | Pattern B2 Therapy Delivery Inhibited by Therapies Programmed Off; 7 Saturations; Episode End Redetection Counts: Pattern A1=11, Pattern B2=14 |
| 358 | Fri, Feb 19, 2021 06:12:08 | 4.5 seconds | Pattern B2 Therapy Delivery Inhibited by Therapies Programmed Off; Episode End Redetection Counts: Pattern A1=0, Pattern B2=0 |
| 359 | Fri, Feb 19, 2021 06:12:15 | 5.0 seconds | Pattern B2 Therapy Delivery Inhibited by Therapies Programmed Off; Episode End Redetection Counts: Pattern A1=0, Pattern B2=0 |
| 360 | Fri, Feb 19, 2021 06:12:24 | 4.5 seconds | Pattern B2 Therapy Delivery Inhibited by Therapies Programmed Off; Episode End Redetection Counts: Pattern A1=0, Pattern B2=0 |
| 361 | Fri, Feb 19, 2021 06:13:00 | 4.5 seconds | Pattern B2 Therapy Delivery Inhibited by Therapies Programmed Off; Episode End Redetection Counts: Pattern A1=0, Pattern B2=0 |

FIG. 14B

| ECOG | Seizure Probability | ECOG Duration |
|---|---|---|
| Feb 21, 2021 11:28:34 Long Episode | 90% | 85 sec |
| Feb 17, 2021 21:10:37 Long Episode | 92% | 92 sec |
| Feb 20, 2021 18:32:31 Long Episode | 70% | 55 sec |
| Feb 18, 2021 21:23:55 Long Episode | 20% | 24 sec |
| Feb 20, 2021 10:38:49 Long Episode | 99% | 102 sec |

FIG. 16

Model Qualification

Composite CRE Biomarker indentification

| Rank | Importance | Data Type |
|---|---|---|
| 1. | 60% | Theta gamma coupling |
| 2. | 22% | Detection rate |
| 3. | 10% | Interictal spike rate |
| 4. | 6% | Seizure onset zone |
| 5. | 2% | High gamma power |

SYSTEMS AND METHODS FOR CONTROLLING OPERATION OF AN IMPLANTED NEUROSTIMULATION SYSTEM BASED ON A MAPPING OF EPISODE DURATIONS AND SEIZURE PROBABILITY BIOMARKERS

CROSS-REFERENCE TO RELATED APPLICATION(S)

This application claims the benefit of and priority to U.S. Provisional Patent Application Ser. No. 63/170,018, filed Apr. 2, 2021, for "Systems and Methods for Combining Neurostimulator Device Data for Estimating Patient's Clinical Outcomes," and U.S. Provisional Patent Application Ser. No. 63/312,429, filed Feb. 22, 2022, for "Systems and Methods for Combining Neurostimulator Device Data for Estimating Patient's Clinical Outcomes," the entire disclosures of which are incorporated herein by reference.

TECHNICAL FIELD

The present disclosure relates generally to biomarkers that provide an estimate of a patient's clinical response to a therapy for a neurological condition, e.g., epilepsy, and more particularly, to systems and methods for obtaining a clinical response estimate (CRE) biomarker using machine-learned models trained on data types derived from implanted neurostimulation systems.

BACKGROUND

One of the biggest challenges in epilepsy treatment is getting a reliable estimate of patient outcomes to treatments. Patient reports of outcomes can be unreliable and incomplete. For example, nighttime seizures are often not counted, and a fraction of epileptic patients have memory-related comorbidities and often do not remember if and when they had a seizure. Achieving an accurate estimate of seizure burden in patients with epilepsy is highly desirable because it would not only allow assessment of therapy effectiveness, but may even help with seizure warning since seizures in patients often have cyclical trends.

SUMMARY

In one aspect of the disclosure, a method of monitoring a clinical response estimate (CRE) biomarker of a patient having an implanted neurostimulation system includes, deriving an input dataset from a subject-patient dataset comprising a plurality of data types that are based on electrical activity of the patient's brain sensed and stored by the implanted neurostimulation system, and at least one feature of the patient. The input dataset is derived based on a plurality of key inputs of the subject-patient dataset. The method also includes processing the input dataset to obtain a plurality of model inputs, and applying a machine-learned CRE model to the plurality of model inputs to determine the CRE biomarker.

In another aspect of the disclosure, an apparatus includes a memory having a plurality of modules, and a processor coupled to the memory. The processor is configured to execute operations based on the plurality of modules, to thereby implement the foregoing method of monitoring a CRE biomarker of a patient having an implanted neurostimulation system.

In one aspect of the disclosure, a method of producing a clinical response estimator for applying to a plurality of model inputs to derive a clinical response estimate (CRE) biomarker for a patient includes, training a first machine-learned model based on a first input dataset derived from a first training dataset. The first training set includes: 1) data types derived from records of electrical activity of a brain sensed and stored by implanted neurostimulation systems, and classified as ictal records, while excluding data types of records of electrical activity of the brain sensed and stored by implanted neurostimulation systems and classified as interictal records, and 2) at least one patient feature. The method also includes training a second machine-learned model based on a second input dataset derived from a second training dataset. The second training set includes: 1) data types derived from records of electrical activity of the brain sensed and stored by implanted neurostimulation systems, and classified as interictal records, while excluding data types of records of electrical activity of the brain sensed and stored by implanted neurostimulation systems and classified as ictal records, and 2) at least one patient feature. The method further includes training an ensemble machine-learned model based on model outputs of the first machine-learned model and model outputs of the second machine-learned model.

In another aspect of the disclosure, an apparatus includes a memory having a plurality of modules including a first training module, a second training module, and an ensemble training module, and a processor coupled to the memory. The processor is configured to execute operations based on the plurality of modules, to thereby implement the foregoing method of producing a clinical response estimator.

In one aspect of the disclosure, a method of informing of a clinical response of a patient as a function of an event of interest that occurred at an associated time includes, processing an input dataset to obtain a pre-event window of model inputs and a post-event window of model inputs. The input dataset is selected from a subject-patient dataset that includes a plurality of data types based on electrical activity of the patient's brain sensed and stored by an implanted neurostimulation system, and at least one feature of the patient. The method also includes applying a clinical response estimator (CRE) model to the pre-event window of model inputs to derive one or more pre-event CRE biomarkers, and applying the CRE model to the post-event window of model inputs to derive one or more post-event CRE biomarkers. The method further includes displaying as a function of time, the one or more pre-event CRE biomarkers, the one or more post-event CRE biomarkers, and an occurrence of the event of interest.

In another aspect of the disclosure, an apparatus includes a display, a memory having a plurality of modules, and a processor coupled to the memory and the display. The processor is configured to execute operations based on the plurality of modules, to thereby implement the foregoing method of informing of a clinical response of a patient as a function of an event of interest.

In one aspect of the disclosure, a method of modifying an operation of an implanted neurostimulation system of a patient includes determining a clinical response estimate (CRE) biomarker includes, comparing the CRE biomarker to a criterion, and responsive to the criterion not being met, adjusting a parameter of the operation, or triggering the operation. The CRE biomarker is determined by deriving an input dataset from a subject-patient dataset that includes a plurality of data types that are based on electrical activity of the patient's brain sensed and stored by the implanted neurostimulation system, and at least one feature of the patient. The input dataset is derived based on a plurality of key inputs of the subject-patient dataset. The input dataset is then processed to obtain a plurality of model inputs, and a machine-learned CRE model trained on datasets across a patient population is applied to the plurality of model inputs to determine the CRE biomarker.

In another aspect of the disclosure, an implantable neurostimulation system includes a detection subsystem, a therapy subsystem, a memory having a plurality of modules, and a processor coupled to the memory, the detection subsystem, and the therapy subsystem. The processor is configured to execute operations based on the plurality of modules to thereby implement the foregoing method of informing of modifying an operation of an implanted neurostimulation system of a patient.

In one aspect of the disclosure, a method of controlling operation of an implanted neurostimulation system configured to sense episodes of electrographic events and determine durations of episodes includes, mapping durations of electrographic events sensed by the implanted neurostimulation system with seizure probability biomarkers derived from records of the electrographic events to create a mapping function. The method further includes, for each of one or more operations of the implanted neurostimulation system, selecting a seizure probability biomarker having a value desired for the operation, selecting a duration mapped to the selected seizure probability biomarker, and programming the duration into a control module of the implanted neurostimulation system as a programmed parameter that triggers the operation by the implanted neurostimulation system.

In another aspect of the disclosure, an apparatus includes a memory having a plurality of modules, and a processor coupled to the memory. The processor is configured to execute operations based on the plurality of modules, to thereby implement the foregoing method of controlling operation of an implanted neurostimulation system.

In one aspect of the disclosure, a method of operation of an implanted neurostimulation system of a patient includes, detecting an electrographic event, determining a duration of an episode of the electrographic event, comparing the episode duration to threshold duration, and initiating an operation of the implanted neurostimulation system solely in response to the episode duration satisfying the threshold duration. The threshold duration corresponds to one of a plurality of threshold durations, each threshold duration associated with a different seizure probability biomarker by a mapping function.

In another aspect of the disclosure, an implantable neurostimulation system includes a detection subsystem, a therapy subsystem, a memory having a plurality of modules, and a processor coupled to the memory, the detection subsystem, and the therapy subsystem. The processor is configured to execute operations based on the plurality of modules, to thereby implement the foregoing method of operation of an implanted neurostimulation system.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects.

Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIG. 14B are records of characteristics of event episodes detected by an implantable neurostimulation system.

FIG. 16 shows various EEG records and a corresponding seizure probability for each.

DETAILED DESCRIPTION

Figure 1A:
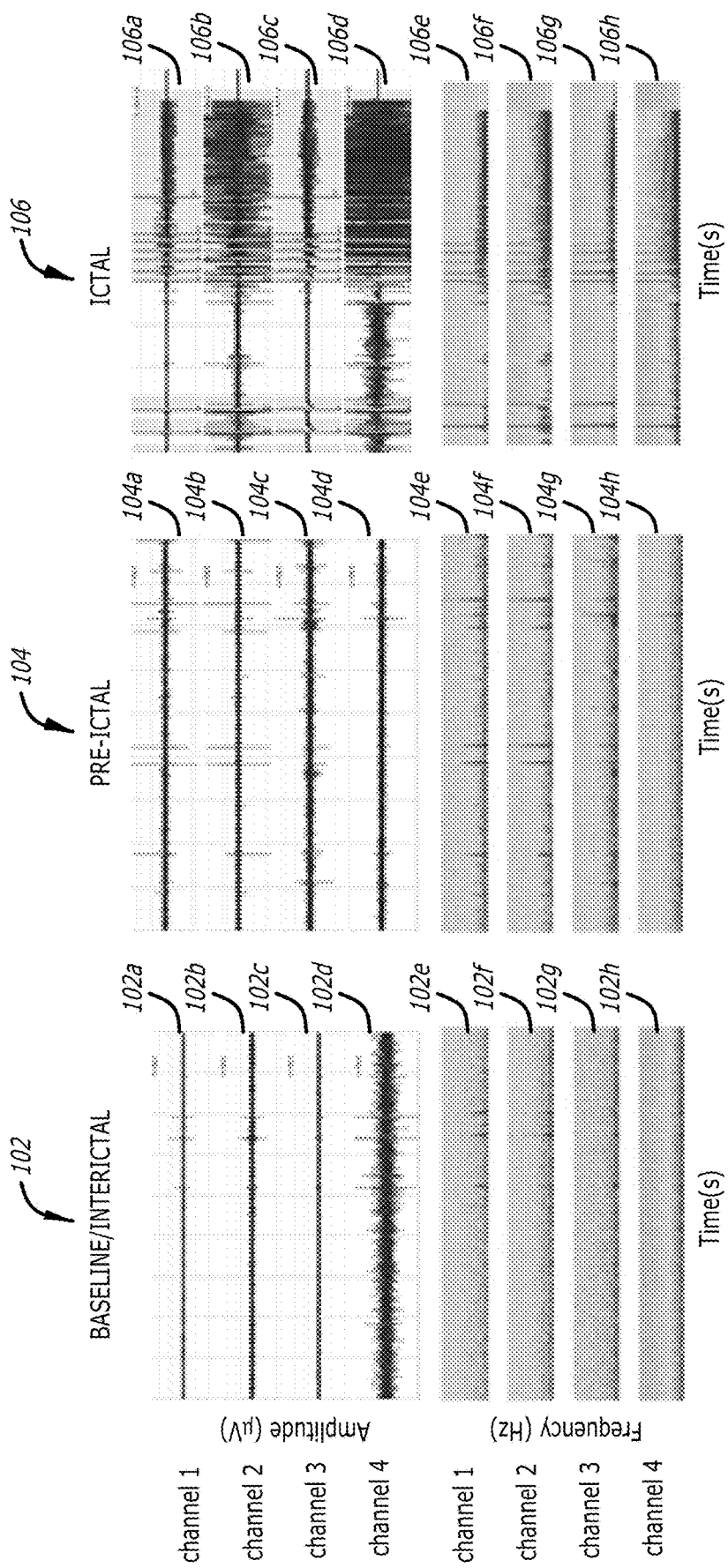
FIG. 1A are example time-series waveform visual representations of EEG records corresponding to electrical activity of the brain recorded by the implanted neurostimulation system, together with their corresponding spectrogram visual representations.

Implantable neurostimulation systems implanted in the brain of patients with the intention of providing electrical stimulation therapy have the ability to sense and record electrical brain activity. For example, an implanted neurostimulation system may capture and store electrical brain activity at specific times of day or in response to a triggering event, such as 1) a magnet swipe over the neurostimulator, or 2) sensing of electrical activity containing high amplitude activity that saturates electronics of the neurostimulation system, or 3) sensing of electrical activity containing long episodes of abnormal patterns or abnormal events (e.g., patient-specific patterns, spikes, etc.). An implanted neurostimulation system may derive different data types from these records of electrical activity, such as counts of abnormal events, the timing and duration of every abnormal event, and measures of power in the recorded electrical activity.

Previous published work shows that some of these data types are associated with clinical outcomes. These works further show that different data types are associated with outcomes in different patient groups. For example, interictal spike rate (i.e., the number of interictal spikes per second) computed in scheduled records of electrical brain activity are correlated with outcomes in patients with mesiotemporal lobe epilepsy. See Desai et al., Quantitative electrocorticographic biomarkers of clinical outcomes in mesial temporal lobe epileptic patients treated with the RNS system, Clinical Neurophysiology 130, 1364-1374, (2019). Power in the high gamma band computed in scheduled records of electrical brain activity are correlated with patient outcomes in the neocortical patient population. See Evaluation of potential epilepsy biomarkers in long-term electrocorticographic activity, AES abstract no. 1.133, www.aesnet.org, (2016). Additionally, long episode rates in records of electrical brain activity have also been shown to be correlated with patient outcomes. See Skarpaas et al., Clinical and electrocorticographic response to antiepileptic drugs in patients treated with responsive stimulation, Epilepsy & Behavior 83, 192-200, (2018).

In accordance with embodiments disclosed herein, a clinical response estimate (CRE) biomarker of a patient having an implanted neurostimulation system is monitored. To this end, an input dataset is derived from a subject-patient dataset that includes various different data types and different features of the patient. The data types are based on of electrical activity the patient's brain sensed and stored by the implanted neurostimulation system. The input dataset is a subset of the larger subject-patient dataset, and the specific data types and patient features included in that subset are derived based on a plurality of key inputs of the subject-patient dataset. Once the input dataset is derived, it is processed to obtain model inputs for a machine-learned clinical response estimator model. Processing of the input dataset may include applying different components or elements of the dataset to different machine-learned models, combining components or elements of the dataset, or a combination of the foregoing. For example, a machine-learned model may be applied to components of the dataset and the output of the model may be combined with another component of the input dataset to provide a model input. The machine-learned clinical response estimator model is applied to the model inputs to determine the CRE biomarker.

Datasets/Data Types

As used herein, a "dataset" refers to a collection of information that may be used to train, test, validate, and use a machine learning model. A dataset may include one or more records or files of information from a patient in whom an implantable medical device (IMD) is implanted. This information may include physiological information from the patient and non-physiological information related to the patient's environment, device configuration, device operation, demographics, conditions, and therapies. Physiological information is also referred to herein as data or data types, while non-physiological information is referred to as patient features.

With respect to physiological information, in the case of an implanted neurostimulation system, a dataset may include records or files of physiological information corresponding to electrical activity of the brain that is sensed by the system. Hereinafter, electrical activity of the brain is referred to as "EEG," and a physiological record corresponding to electrical activity of a patient's brain is referred to as an "EEG record." It will be understood that EEG includes electrical activity sensed directly from the neural tissue, which sometimes is referred to as electrocorticographic activity, an electrocorticogram, or "ECoG," or intracranial EEG ("iEEG").

With additional reference to FIG. 1A, EEG records 102, 104, 106 included in a dataset may be visualized or represented in different forms. In the upper portion of FIG. 1A, EEG records 102, 104, 106 are represented by time series waveform images 102a-d, 104a-d, 106a-d for each of four sensing channels of an implanted neurostimulation system. Each EEG record 102, 104, 106 was captured with an implanted neurostimulator system during a respective one of a baseline/interictal brain state (e.g., no seizure), a preictal brain state (e.g., activity captured within the hours before the onset of seizures), and an ictal brain states (e.g., a seizure) in an example patient. In the lower portion, the same EEG records 102, 104, 106 are represented by spectrograms 102e-h, 104e-h, 106e-h for each of four sensing channels.

Figure 1B:
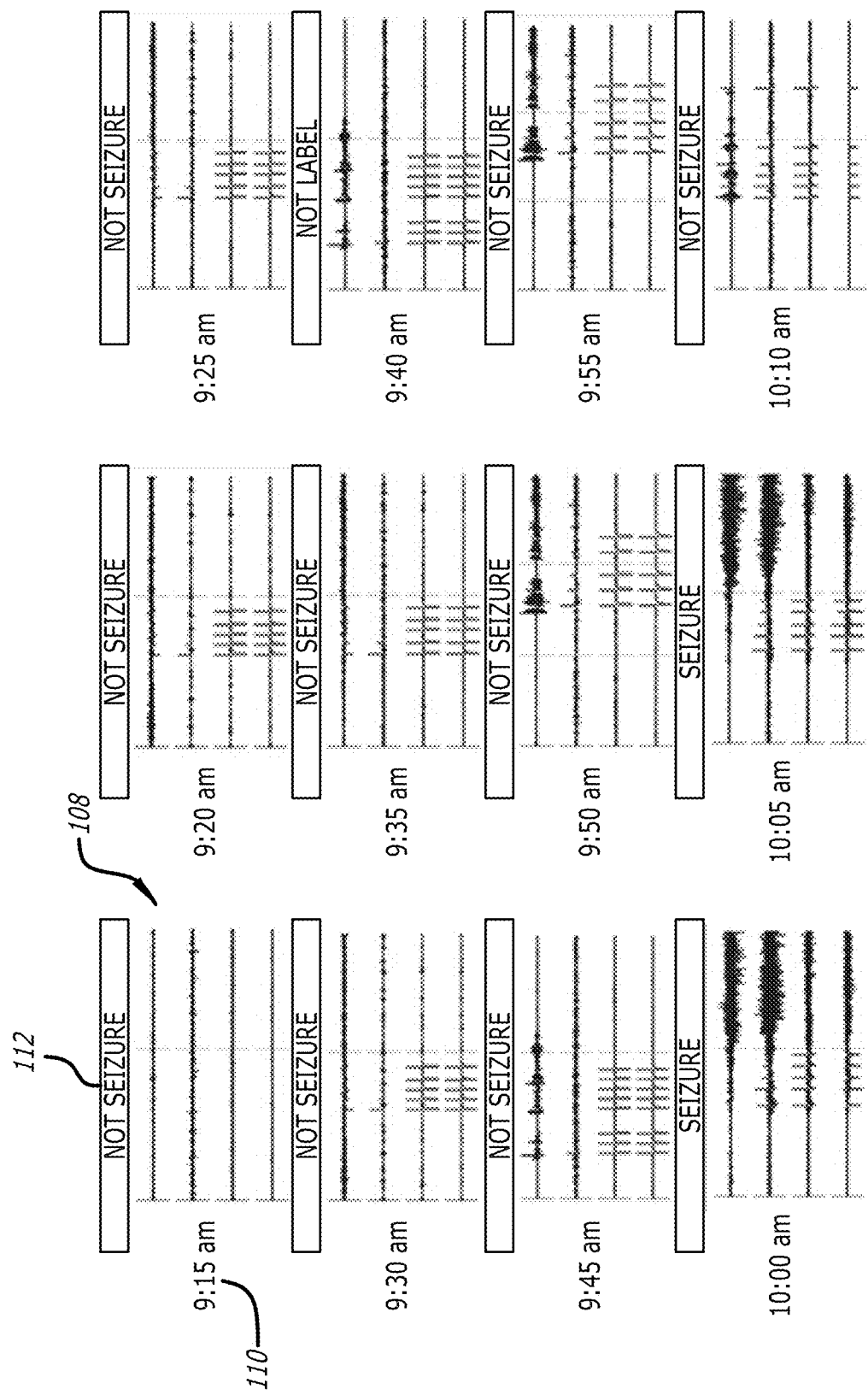
FIG. 1B are examples time-series waveform visual representations of EEG records, together with additional information, e.g., time stamps and seizure/non-seizure labels, associated with the records and included in the patient dataset.

With reference to FIG. 1B, additional information or data type may be associated with EEG records. For example, each individual EEG record 108 may have an associated time stamp 110 corresponding to the time the EEG signals within the record were captured by the implanted neurostimulation system. Each individual EEG record 108 may also have an associated label 112 classifying the EEG signals within the record as being indicative of a seizure or not a seizure. Other examples of additional information that may be associated with each EEG record include the event that triggered creation of the EEG record. As described further below, such triggering events may include a detection of abnormal electrical activity in an EEG signal, a patient-initiated event, e.g., a swipe of a magnet in the area of the implanted neurostimulation system, or a scheduled passage of time.

Figure 1C:
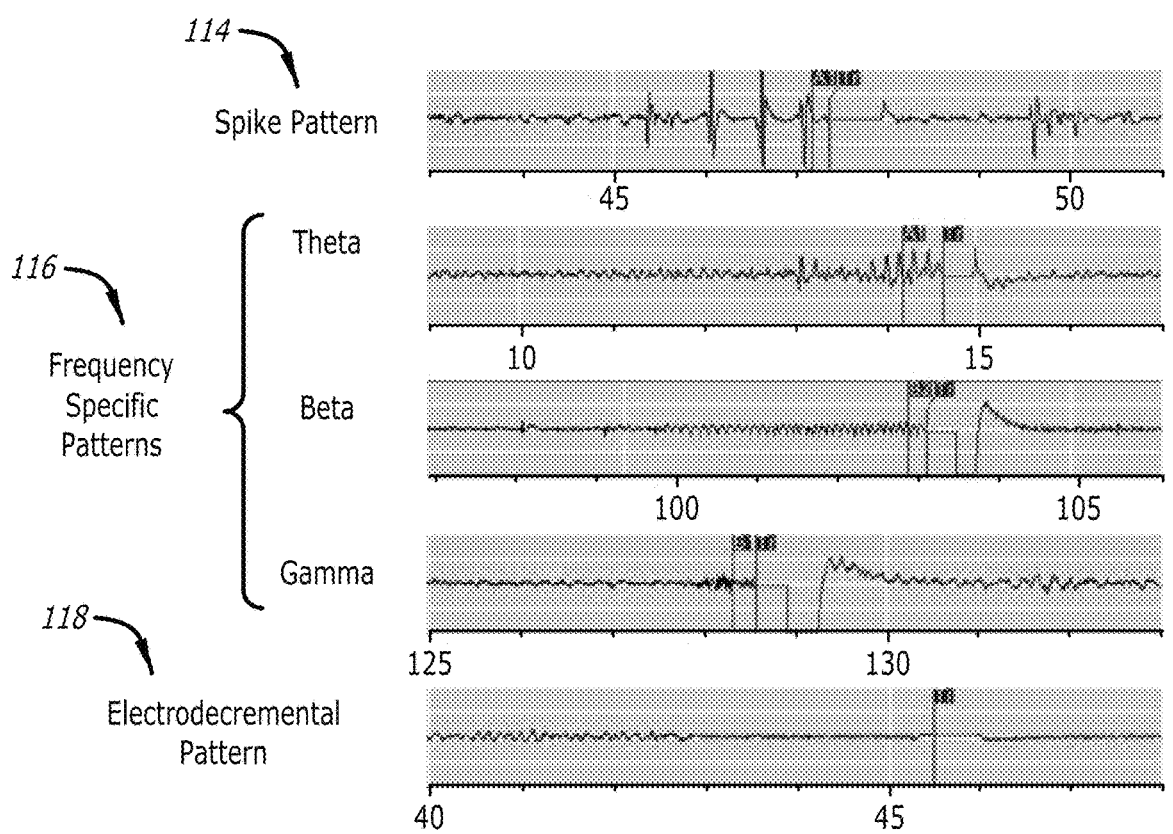
FIG. 1C are examples of time-series waveform visual representations of EEG records corresponding to patterns of electrical brain activity including spikes, oscillatory patterns, and amplitude and/or frequency changes.
Figure 1C:
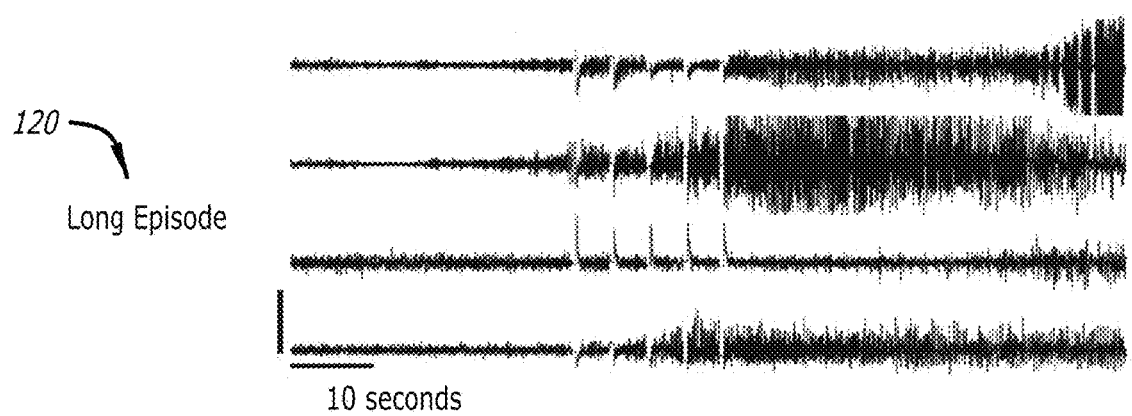

Additional information or data types may be derived by an implanted neurostimulation system from sensed EEG signals and included in a dataset. For example, the implanted neurostimulation system may be configured to detect patterns in a patient's electrical brain activity and to maintain records of the timing of detections, the count of the number of detections, and a detection rate. The count of such detections may be included in a dataset, either with or without an EEG record of the detected patterns. With reference to FIG. 1C, example patterns of electrical brain activity include spikes 114, oscillatory patterns 116, and amplitude and/or frequency changes 118. The implanted neurostimulation system may also be configured to detect abnormal electrical brain activity having a duration that exceeds a specified threshold, and to maintain records of the timing and count of the number of such detections together with information, e.g., time stamps, indicative of the time and duration each detection. This abnormal electrical brain activity is referred to as a "long episode." An example pattern of a long episode 120 is shown in FIG. 1C. The count of detections of long episodes 120 and the respective duration information of each may be included in a dataset, either with or without EEG records of the detected long episodes.

The implanted neurostimulation system may be configured to derive measures from a patient's electrical brain activity and to maintain records of the measures. For example, the implanted neurostimulation system may measure spectral power in certain frequency bands (example 1-4 Hz band, 4-8 Hz band, 8-2 Hz band, 12-25 Hz band, 25-50 Hz band, 50-90 Hz band and so on) computed in small moving and overlapping time windows such as 128, 256 or 512 milliseconds.

While the methods and systems disclosed herein are primarily described with reference to EEG records, it will be appreciated that other physiological information and non-physiological information may be processed. To this end, other types or modalities of physiological information derived from sources other than EEG records may be included in a dataset. For example, physiological records may include measurements of pH level in neural tissue, blood oxygen levels in neural tissue, blood flow rates, neurotransmitters concentrations in neural tissue, temperatures, heart rates, blood pressures, blood glucose levels, hormones sensed in sweat, skin conductivity, accelerometer/motion recordings, posture, and sleep patterns. This information may be sensed and recorded locally by an implanted medical device, or sensed remote from the implanted medical device, such as from an external wearable device, and may be transmitted to the implanted device for local storage.

With respect to non-physiological information or patient features, a dataset may include records or files of the patient's demographics (e.g., age, gender, etc.), the patient's drug regimen (e.g., type of drug, dose, and time of day of dose), and the patient's clinical outcomes, such as the rate of clinical seizures (e.g., as reported in a seizure diary), mood, or questionnaire information. A dataset may also include configuration/operation information of the implanted neurostimulation system. Example configuration/operation information includes detection parameters used by the system to detect patterns in a patient's electrical brain activity, and stimulation parameters that define a stimulation therapy delivered by the system.

Examples of different data types that may be included in a patient dataset are listed in Table 1:

TABLE 1

| Data Source | Data Type |
| --- | --- |
| EEG (electrical activity of the brain) | counts - long episodes (LE), spikes, electrographic seizures, abnormal patterns/events<br>rates - long episodes (LE), spikes, electrographic seizures, abnormal patterns/events<br>durations - long episodes (LE), spikes, electrographic seizures, abnormal patterns/events<br>distributions - long train distributions (distribution of episodes that are >10 seconds)<br>classifications - ictal or interictal<br>brain activity type (determined by machine-learned model) |

TABLE 1-continued

| Data Source | Data Type |
|---|---|
| | measures - total spectral power, spectral power in certain frequency bands (example 1-4 Hz band, 4-8 Hz band, 8-2 Hz band, 12-25 Hz band, 25-50 Hz band, 50-90 Hz band, phase amplitude coupling, coherence. |
| | spectrogram images |
| | time-series images |
| | coherograms, coherence in seizure activity |
| | coherograms, coherence in scheduled EEG record activity |
| non-EEG | pH level |
| | blood oxygen, flow rate, pressure |
| | temperature |
| | heart rate |
| | neurotransmitter concentrations |
| | glucose level |
| | skin conductivity |
| | hormones sensed |
| | motion/accelerometer |
| | posture |
| | sleep pattern |

Examples of different patient features that may be included in a patient dataset are listed in Table 2:

TABLE 2

| Feature Source | Feature |
|---|---|
| patient demographics | age - current, at epilepsy onset, age at implant, sex, race, etc. |
| | duration of epilepsy (years) |
| | sex |
| | type of job |
| | geographical location |
| patient diagnoses/ treatments | seizure frequency during pre-implant period |
| | lobe of epilepsy onset - MTL, neocortical, MTL + neocortical |
| | brain abnormalities - presence of sclerosis, dysplasia |
| | prior cortical resection (yes/no) |
| | prior vagus nerve stimulation (yes/no) |
| | prior EEG monitoring with intracranial electrodes (yes/no) |
| | drug regimen - list and dosage of medications |
| | clinical outcomes |
| | seizure diary |
| implanted neurostimulation system | setting - detection parameters, stimulation parameters |
| | lead implant location |
| | lead type/number - strip, depth |

Overview of System

Figure 2:
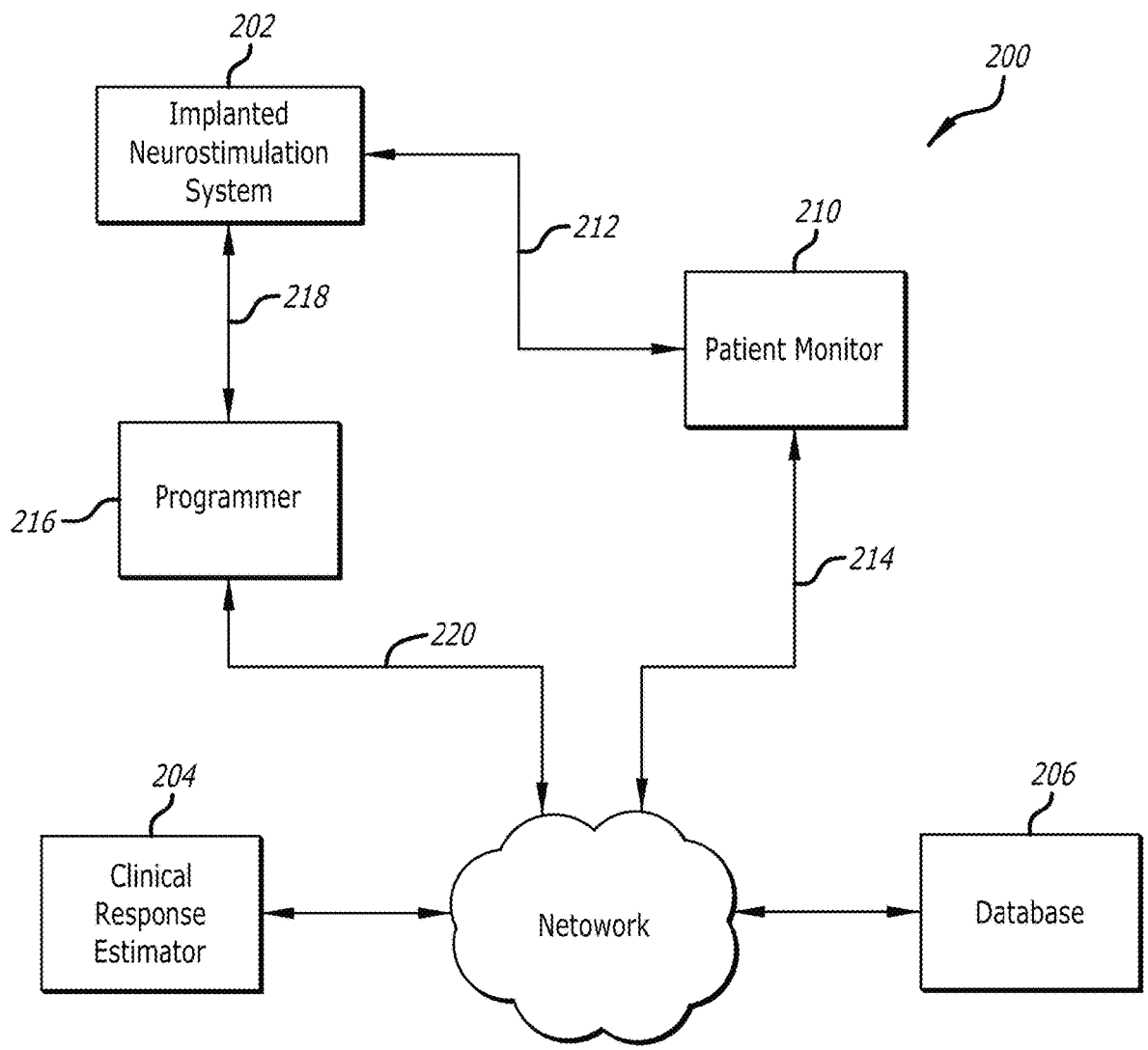
FIG. 2 is a block diagram illustration of a system, including an implanted neurostimulation system, a clinical response estimator, and other external equipment, which enable the derivation of a clinical response estimate (CRE) biomarker for a patient.

FIG. 2 is a block diagram illustration of a system 200 in which machine-learned models, e.g., deep learning models, are applied to a dataset of a patient to derive estimates of a patient's clinical response. The system includes an implanted neurostimulation system 202, a clinical response estimator 204, and a database 206, each configured to provide and/or obtain a patient's physiological and non-physiological information over a network 208.

Physiological records corresponding to EEG records may be captured by the implanted neurostimulation system 202. As noted above, these EEG records may correspond to digitally recorded time series samples of electrocorticographic activity (e.g., a time series waveform). These EEG records may also be in another form or format derived from the time series samples. For example, an EEG record may be a spectrogram image or a time series waveform image of the brain electrical activity. (It will be appreciated that any time-series EEG can be represented as a spectrogram.) Alternatively, time-series waveforms may be directly used.

Other types of physiological information, e.g., pH levels, blood oxygen levels, neurotransmitters concentrations, heart rate, blood pressure, blood glucose levels, hormone levels, sleep states, posture, etc., may be captured and preserved by an implanted neurostimulation system 202 as physiological records. Collectively, the EEG records and other physiological records preserved by an implanted neurostimulation system 202 are part of a dataset for the patient in which the device is implanted. Non-physiological information, forms part of the dataset and may include records or files of patient demographics (e.g., age, gender), patient drug regimen (e.g., type of drug, dose, and time of day of dose), and patient clinical outcomes, such as the rate of electrographic seizure detection and electrographic seizure onset (e.g., as detected and recorded by the implanted neurostimulation system), the rate of clinical seizures (e.g., as reported in a seizure diary or detected based on accelerometer recordings).

The neurostimulation system 202 includes implantable components, namely, an active medical device or neurostimulator, and one or more electrode-bearing leads. The electrodes are configured to rest in or on neural tissue in the patient's brain when the leads are implanted. The neurostimulator may be configured to be implanted in or on the patient's cranium or elsewhere in the patient (e.g., pectorally). Once the neurostimulator is implanted, a proximal end of each lead is connected to the neurostimulator. The combination of the active implanted medical device and the implanted lead(s) is configurable to sense physiological signals from the brain and process and store records of the sensed signals. In this example, the physiological signals the electrodes sense and transmit through the lead(s) to the neurostimulator are electrocorticographic signals. The neurostimulator is configured to record samples or segments of the sensed EEGs, and to store them in a memory.

A neurostimulation system 202 may capture data types listed in Table 1 based on EEG signals. Data types may be captured at different time scales. Some examples of data types captured by a neurostimulation system 202 include: (1) continuous recordings (ECoG records) of raw brain data at a certain sampling rate such as 1000, 500 or 250 Hz, (2) continuous measures of derived brain data such as spectral power in certain frequency bands (example 1-4 Hz band, 4-8 Hz band, 8-2 Hz band, 12-25 Hz band, 25-50 Hz band, 50-90 Hz band and so on) computed in small moving and overlapping time windows such as 128, 256 or 512 milliseconds; (3) counts of abnormal events in bins of varying durations such as minutes, days or hours; (4) sampled raw time series or derived brain data that are saved at random time points, specific time points (preprogrammed by a physician for example) or are sampled in response to a trigger such as detection of abnormal events in brain or when a patient swipes a magnet over the neurostimulator; and (5) patient reports of outcomes. These are almost always not continuous and only intermittently available.

A neurostimulation system 202 may also be configured to sense and record other types of physiological signals besides EEG signals. To this end, the neurostimulation system 202 may include a lead as disclosed in U.S. Pat. No. 10,123,717, entitled Multimodal Brain Sensing Lead, which is herein incorporated by reference. Such a multimodal brain sensing lead may include: (1) macroelectrodes; (2) microelectrodes; (3) light emitters; and (4) photodetectors. Different sensing modalities of the implanted neurostimulation system 202 use the different transducers as follows: (1) neuronal field potential measurements are made using macroelectrodes; (2) neuronal single unit activity measurements are made using microelectrodes; (3) neuronal multi-unit activity measurements are also made using microelectrodes; (4) rheoencephalography measurements are made using macroelectrodes; (5) neurochemical and pharmaceutical voltammetric measurements are made using both macroelectrodes and microelectrodes; (6) optical blood flow and volume measurements are made using light emitters and photodetectors; and (7) optical blood oxygenation measurements are also made using light emitters and photodetectors.

Configured as such, the neurostimulation system 202 may sense and record signals indicative of blood oxygen level and blood volume in neural tissue, and signals indicative of chemical concentrations and neurotransmitter concentrations in neural tissue. From these signals, the neurostimulation system 202 may derive other physiological information. For example, blood flow, blood oxygenation, blood pressure, heart rate, and breathing rate may be estimated from blood oxygen and blood volume measurements, while pH levels and blood glucose levels may be derived from chemical concentrations and neurotransmitter concentrations.

The neurostimulation system 202 may also include one or more electrodes configured to sense electrical cardiac activity indicative of heart rate, a pressure sensor configured to provide signals indicative of blood pressure, an accelerometer configured to provide motion signals indicative of motion and the position of the patient. From these accelerometer signals, the implanted neurostimulation system 202 may derive other physiological information corresponding to clinical seizures, patient posture, and sleep state.

Other types of physiological information may be obtained and stored by the neurostimulation system 202 from sources independent of the neurostimulation system. For example, an external wearable device, e.g., patch, may include a sensor configured to sense and track cortisol levels, i.e., stress hormones, in sweat, while an external wearable device, e.g., watch, may include or a sensor configured to sense blood pressure. The physiological information from these external devices may be transmitted to the implanted neurostimulation system 202 for inclusion in the patient's dataset.

Records of physiological information may be generated by the neurostimulation system 202 based on an occurrence of an event or trigger. To this end, a neurostimulation system 202 can be configured to create an EEG record of a sensed EEG when an event the system is programmed to detect is detected. For example, the neurostimulation system 202 may be configured to detect an event corresponding to an electrographic seizure or the onset of an electrographic seizure from a sensed EEG, and to create an EEG record of the corresponding EEG signal spanning the time period 60 seconds before the event was detected and 30 seconds thereafter. The neurostimulation system 202 can also be programmed to create an EEG record of a sensed EEG at certain times of day (e.g., at noon and at midnight). These are sometimes referred to as "scheduled EEGs." In addition, then neurostimulation system 202 may be configured to store an EEG record upon some other trigger, such as when the patient swipes a magnet over the location on the patient's body at which the neurostimulator is implanted (the patient might be instructed to do this whenever he or she thinks a seizure is coming on).

The neurostimulation system 202 can also be programmed to designate EEG records based on the event that triggered its recording and to include that designation in the EEG record. For example, EEG records resulting from the detection of abnormal electrical activity, e.g., an electrographic seizure or the onset of an electrographic seizure, may be marked as such, while EEG records EEGs that do not reflect abnormal activity may be designated as baseline EEG records. Thus, for a given patient, a dataset may contain EEG records corresponding to what is happening in the patient's brain during and around when an event occurs, scheduled EEG records acquired at a particular time, and EEG records stored by the neurostimulator when a patient triggers storage with a magnet. Some of these EEG records, especially the ones recorded at the time of an event or when triggered by a magnet swipe, may reflect the patient's electrographic seizures. The dataset may include information or a data type about whatever triggered the neurostimulator to store a given EEG, such as the type of event (e.g., Pattern "A" or Pattern "B," a magnet swipe) or the time of day (e.g., scheduled EEG).

Typically, some sort of linkage or mapping among the various types of physiological information is provided in a dataset. To this end, each record may have one or more associated tags or parameters. For example, physiological records may have a time stamp that allows a set of physiological records at a given point in time to be located for processing. Physiological records may have a tag that indicates the basis, e.g., seizure detection, magnet swipe, scheduled time of day, for preserving the record. These tags allow a set of physiological records to be selected for processing based on a single criterion or a combination of criteria. Other tags may include day of capture, area of the brain at which the electrical activity was captured, basis for record creation (e.g., seizure detection, scheduled, patient initiated), characteristic of the record (e.g., power spectral density of EEG signal prior to stimulation).

Once created by a neurostimulation system 202, physiological records stored in the system can be relayed elsewhere, such as to an external component like the database 206 either directly or through an interim external component. For example, the patient monitor 210 can be used with an accessory (not shown) to establish a communications link 212 with the implanted neurostimulator (e.g., a short-range telemetry link), which allows records stored on the neurostimulator to be transmitted to the patient monitor 210. Once on the patient monitor, the physiological records can be transmitted to the database 206 via the network 208 (which may comprise a physical 214, WiFi, or cellular internet transmission).

Alternatively, the clinician may be provided with an external component, such as a programmer 216 that, like the patient monitor 210, is configured to establish a communications link 218 with the implanted neurostimulator. The clinician can use the programmer to adjust the programmable parameters of the neurostimulator (e.g., the parameters that govern the electrical stimulation waveform that is used for therapy). The programmer 216 is able to specify and set variable parameters in the implanted neurostimulation system 202 (e.g., detection parameter sets and stimulation parameter sets) to adapt the function of the device to meet the patient's needs, upload or receive data from the neurostimulation system to the programmer, download or transmit program code and other information from the programmer to the neurostimulator, or command the neurostimulator to perform specific actions or change modes as desired by a physician operating the programmer.

The programmer also may be used to display the real-time EEG signals being sensed by the electrodes from the patient and to store them on the programmer. It also can be used like the patient monitor 210 to acquire physiological records that have been stored by the neurostimulator since the last time the neurostimulator was "interrogated" for those records by either a patient monitor 210 or programmer. As is the case with a patient monitor 210, once physiological records are stored on a programmer, they can be transmitted via the network 208 to other components of the system 200, such as the database 206 and/or the clinical response estimator 204 (either directly or via the database 206).

A neurostimulation system 202 may be configured to deliver electrical stimulation therapy in response to "events" that the neurostimulator is configured to detect. An event may be defined for the neurostimulator by setting the values of programmable detection parameters such that when a pattern corresponding to a pattern defined by the detection parameters occurs in the monitored EEG signals, the occurrence of that pattern will be detected as an event. Other implantable neurostimulation systems that might be used in the subject system may not have this feature of responsive neurostimulation at all or may not have it enabled.

The database 206 may store other information about a patient as the result of other algorithms or computations. For example, the system and methods for labeling EEG records disclosed herein may be applied to EEG records stored in the database 206 to classify or label the EEG records as evidencing an event or condition, such as those evidencing an electrographic seizure or onset of an electrographic seizure, and those evidencing no electrographic seizure activity at all or those considered to comprise a "baseline" condition for the patient.

While FIG. 2 illustrates a single implanted neurostimulation system 202 and patient monitor 210 and programmer 216, numerous neurostimulation systems implanted across a patient population may access the network 208 to provide patient physiological records and patient information to the clinical response estimator 204 and the database 206. Accordingly, the system 200 can provide access to tens of thousands of patient EEG records.

Clinical Response Estimator

Figure 3:
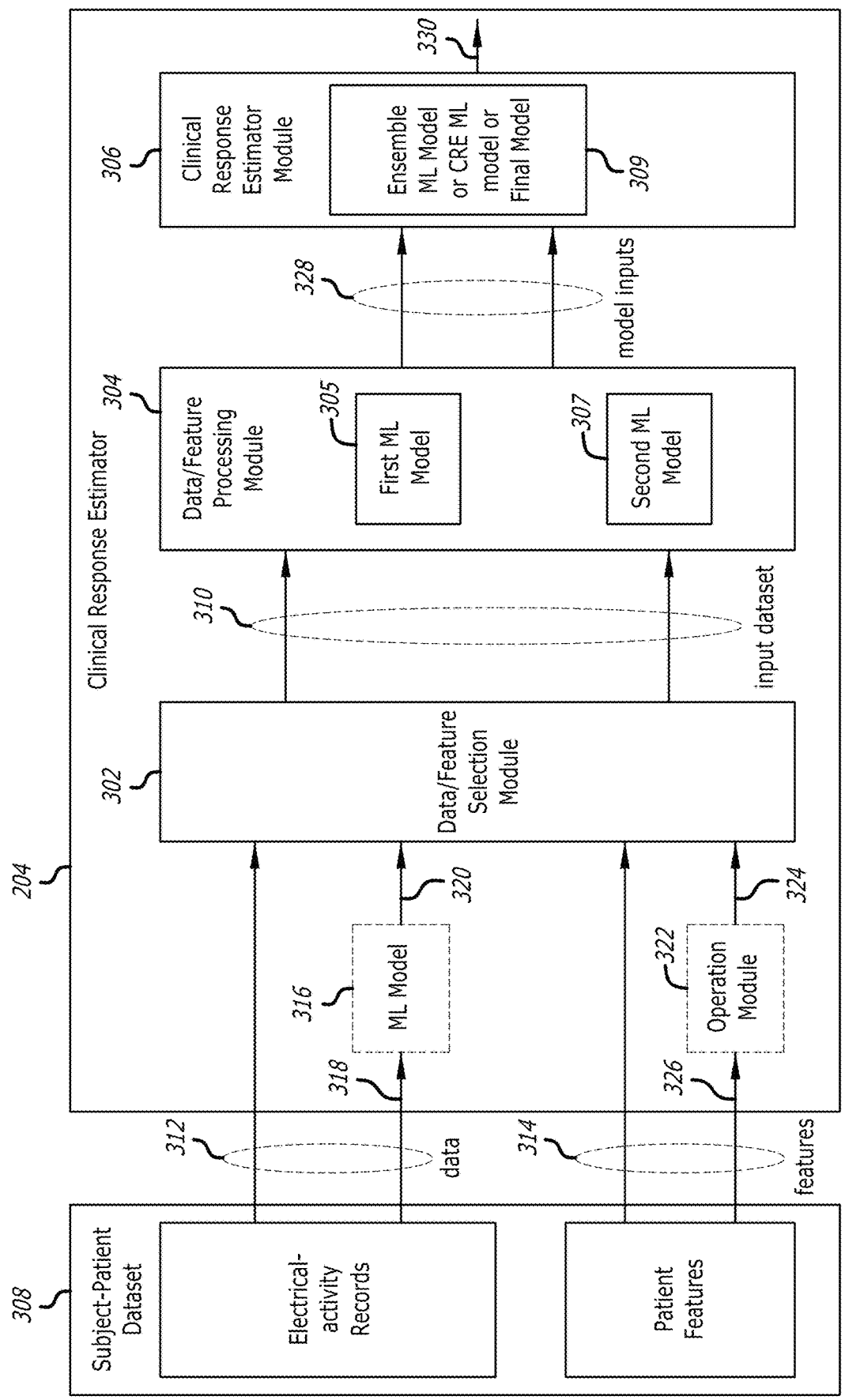
FIG. 3 is a functional block diagram of a clinical response estimator that includes a machine-learned clinical response estimator model that estimates, based on a patient dataset, a patient's clinical response to a treatment, e.g., neurostimulation therapy, drug therapy, surgery, or to an event of interest.

With reference to FIG. 3, in some embodiments a clinical response estimator 204 for monitoring a CRE biomarker of a patient having a neurostimulation system 202 includes a data/feature selection module 302, a data/feature processing module 304 having a first machine-learned model 305 and a second machine-learned model 307, and a clinical response estimator module 306 having an ensemble machine-learned model 309 (also referred to herein as a CRE model or a final model). The data/feature processing module 304 may have other machine-learned models in addition to the first machine-learned model 305 and the second machine-learned model 307. The clinical response estimator 204 obtains data 312 and features 314 from a subject-patient dataset 308 for the patient. The subject-patient dataset 308, which may be obtained from the database 206 of the system of FIG. 2 or directly from the implanted neurostimulation system 202, may include data 312 of different types including data types that are based on electrical activity records, and patient demographic features 314, such as described above and listed in Table 1.

The data/feature selection module 302 derives an input dataset 310 from the subject-patient dataset 308 based on a plurality of key inputs of the subject-patient dataset. The key inputs may include one or more of the different types of data 312, one or more of the different patient features 314, or a combination of data types and features.

A key input may automatically be derived based on one or more data types 312 or one or more patient features 314. For example, a key input may be a brain activity classification or brain activity type derived from raw EEG records of the patient. Accordingly, in some embodiments the clinical response estimator 204 may include a machine-learned model 316 that is applied to raw EEG records 318 to determine a brain activity type 320 of the patient that serves as a key input. Examples of machine-learned models for determining brain activity type are disclosed in U.S. Patent Application Publication Nos. 2019/0117978 and 2020/0272857, which are hereby incorporated by reference. In another example, a key input may be a combination of patient features 314. Accordingly, in some embodiments the clinical response estimator 204 may include an operation module 322 configured to perform operations on the multiple features 326 to determine a combined patient feature 324 that serves as a key input. To this end, the operation module 322 may receive one or more demographic features 326 and perform an AND or OR combine operation on the features. For example, the key input 324 is a '1' if the patient's age is less than 30 AND if the patient has sclerosis. If the AND conditions are not satisfied, then the key input 324 is a '0' otherwise.

A key input may also be manually specified by a user. For example, based on literature, a user may determine that patient features like the lobe of onset and presence or absence of sclerosis are key inputs.

The data/feature selection module 302 processes the key inputs to determine the input dataset 310 to which the first machine-learned model 305 and the second machine-learned model of the data/feature processing module 304 will be applied. To this end, the data/feature selection module 302 may be configured to automatically determine one or more data types to include in the input dataset 310 based on 'type of brain activity.' For example, if a key input 320 indicates the patient has type 5 brain activity, the data/feature selection module 302 may determine that the input dataset includes long episode counts and power in theta band. If the key input 320 indicates the patient has type 7 brain activity, the data/feature selection module 302 may determine that the input dataset includes power in gamma band and interictal spike rate.

The data/feature processing module 304 processes the input dataset 310 to obtain a plurality of model inputs 328 to which the ensemble machine-learned model 309 of the clinical response estimator module 306 is applied. The types of processing executed by the data/feature processing module 304 may be based on the one or more of the key inputs.

Types of processing executed by the data/feature processing module 304 may include: (1) raw EEG data processing, (2) applying machine-learned models to subsets of the input dataset 310, and (3) combining two or more components of the input dataset.

(1) In some embodiments the input dataset 310 may include EEG records comprising raw EEG data. In this case, the data/feature processing module 304 may be configured to process the raw data to provide different types of data. For example, the data/feature processing module 304 may be configured to process raw EEG data to obtain one or more of the following data types: abnormal event (AE) detection counts, AE detection rate, AE duration, long episode (LE) detection counts, LE rate, LE duration, spike detection, spike count, spike rate. The data/feature processing module 304 may be configured to process the raw EEG data to obtain a data type corresponding to a measure. For example, the data/feature processing module 304 may be configured determine spectral power in certain frequency bands (e.g., 1-4 Hz band, 4-8 Hz band, 8-2 Hz band, 12-25 Hz band, 25-50 Hz band, 50-90 Hz band, etc.) computed in small moving and overlapping time windows such as 128, 256 or 512 milliseconds. The extracting of spectral power in specific frequency bands may be referred to herein as "filtering." The data/feature processing module 304 may be configured to process the raw EEG data to obtain a data type in the form of graphical representations such as time-series waveforms, spectrograms, and coherograms.

(2) Applying machine-learned models to subsets of the input dataset 310. The first machine-learned model 305 may be applied to a subset of the input dataset 310 that include data types based on ictal activity of the brain. The second machine-learned model 307 may be applied to data types based on interictal activity of the brain. Applying models may include:

(i) Applying an unsupervised dimensionality reduction algorithm, such as principal component analysis (PCA) or t-SNE. For example, power in 10 different frequency bands, spike rate, long episode rate and features extracted by a trained convolutional neural network (CNN) applied to a spectrograms of raw EEG data may be passed through a PCA to extract the top ten principal components.

(ii) Applying supervised machine learning models. A trained support vector machine (SVM) classifier can be applied on different data types. For example, a data type may be processed to determine two different types of transformed data corresponding to spike rate and LE rate. A trained SVM regression model may be applied to the spike rate and LE rate. The output of the SVM model could be the seizure rate in the patient example (3 seizures/month).

(iii) Multi-level processing. For example, a level-1 ML model may be applied to two different types of data to produce a level-1 output. A level-2 ML model is then applied to the level-1 output and a subset of data types (e.g., two transformed data).

(3) Combining two or more components of the input dataset, including:

(i) Using an AND or OR operator. For example, a demographic feature such as gender can be ANDed with another demographic feature such as age>30 filter.

(ii) Calculating the mean, median, maximum, minimum values of the measures. For example, the spectral power in each of a first frequency band and a second frequency band may be measured and the mean of spectral powers may be computed. Using a weighted average approach. For example, 0.3*power in high gamma frequency band+ 0.7*power in delta frequency band.

(iii) Deriving a threshold episode duration for identifying electrographic events having a certain probability of being and electrographic seizure, where the threshold episode duration is based on a combination of episode durations and seizure probabilities.

The ensemble machine-learned model 309 included in the clinical response estimator module 306 is configured to be applied to the model inputs 328 to provide a CRE biomarker. In some embodiments, the ensemble machine-learned model 309 includes a weighted model. In some embodiments, the ensemble machine-learned model 309 includes a regression model (e.g., a partial least squares regression model, or a random forest regression model). In some embodiments, the ensemble machine-learned model 309 includes recurrent neural networks, convolutional neural networks, transformers, classification models, deep learning models. In one configuration, the ensemble machine-learned model 309 is a machine-learned algorithm trained as described below in the "Building a Clinical Response Estimator" section of this disclosure.

The ensemble machine-learned model 309 is applied to the model inputs 328 to provide a CRE biomarker 330. The CRE biomarker 330 may be a value or a quantity that represents, for example: a) an estimate of the seizure rate in a given window of interest (example in the most recent 14 days, 28 days, 84 days, or since the last event of interest), or b) an estimate of change in seizure rate since the last event of interest. The CRE biomarker 330 may additionally be a classification along with classification accuracy. For example, the CRE biomarker 330 could be a classification of patient's response into five response buckets (example: bucket 1: increase in seizures, bucket 2: 0-25% reduction in seizures, bucket 3: 25-50% reduction in seizures, bucket 4: 50-75% reduction in seizures, and bucket 5: 75-100% reduction in seizures), along with classification certainty (a value between 0 and 100%). Examples of different representations of CRE biomarkers are provided later below with reference to FIGS. 9A-9D.

Process Graphs of Patient-Specific Input Datasets

Figure 4:
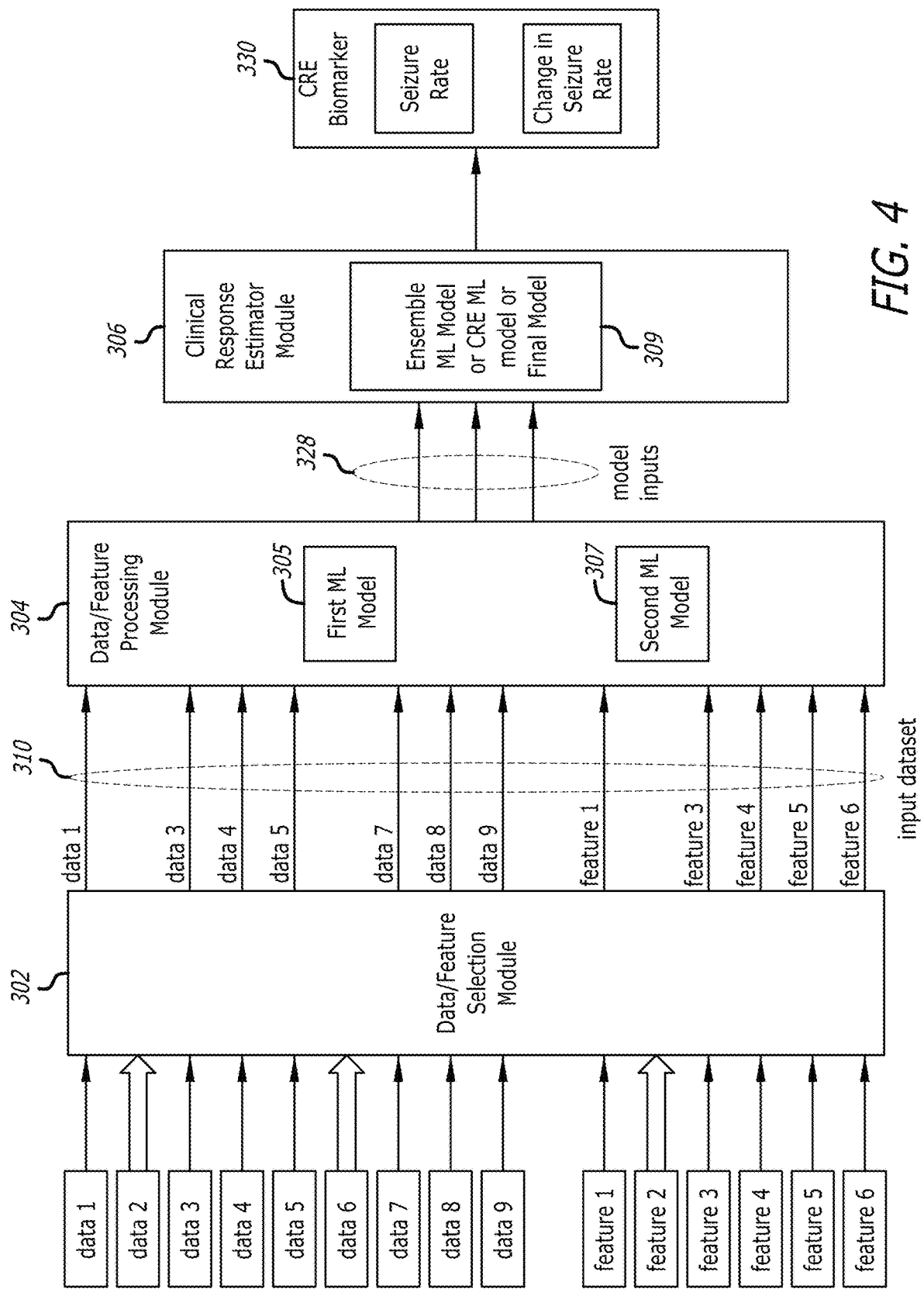
FIG. 4 is a generic process flow graph of a clinical response estimator illustrating various steps involved in determining a CRE biomarker from a patient-specific dataset.

FIG. 4 is a generic process flow graph of a clinical response estimator illustrating various steps involved in determining a CRE biomarker 330 from a patient-specific dataset. "Graph" in this context refers to the way that the clinical response estimator selects and processes an input dataset 310.

Starting from the left side of the graph, a patient-specific dataset including different data types (data1-data9) from an implanted neurostimulation system and patient features (feature1-feature6) are used as input. Depending on one or more key inputs corresponding to one or more of the data types (data1-data9) and one or more of the patient features (feature1-feature6), the graph of the clinical response estimator is automatically or manually determined. In FIG. 4, data2 and data6 from the implanted neurostimulator and patient feature 2 are the key inputs.

As previously described, key inputs may be determined manually or automatically via training a machine learning model. As an example, a set of key inputs may include a key feature that is manually identified to be patient age, and a key data that is manually identified to be spike rate. Manually designed rules may be applied for estimating the final output. Example: if the patient age is over 30 years and if the spike rate is over 1 spike/minute, then the clinical response estimator may use long episode rate and spike rate at 0.5 weight each to estimate the seizure rate. In an automatic determination, one or more key inputs are selected from the patient-specific dataset (data1-data9 and feature1-feature6) by applying a machine-learned model to the dataset that is trained to identify the key inputs (e.g., data2 and data6).

A machine-learned model may be applied to the key inputs to automatically determine the graph, or rule-based methods may be used to determine the graph manually. The key inputs may also be applied to a machine-learned model to determine the input dataset 310 (one or more data1-data9 and feature1-feature6) used to determine the CRE biomarker 330 (e.g., estimated seizure rate for the patient or an estimated change in seizure rate for the patient). In FIG. 4, data1, data3-data5, data7-data9, feature1, and feature 3-feature6 are the input dataset 310

The key inputs also determine how the data and features in the input dataset 310 are processed by the data/feature processing module 304 to provide the model inputs 328 to the clinical response estimator module 306.

Figure 5A:
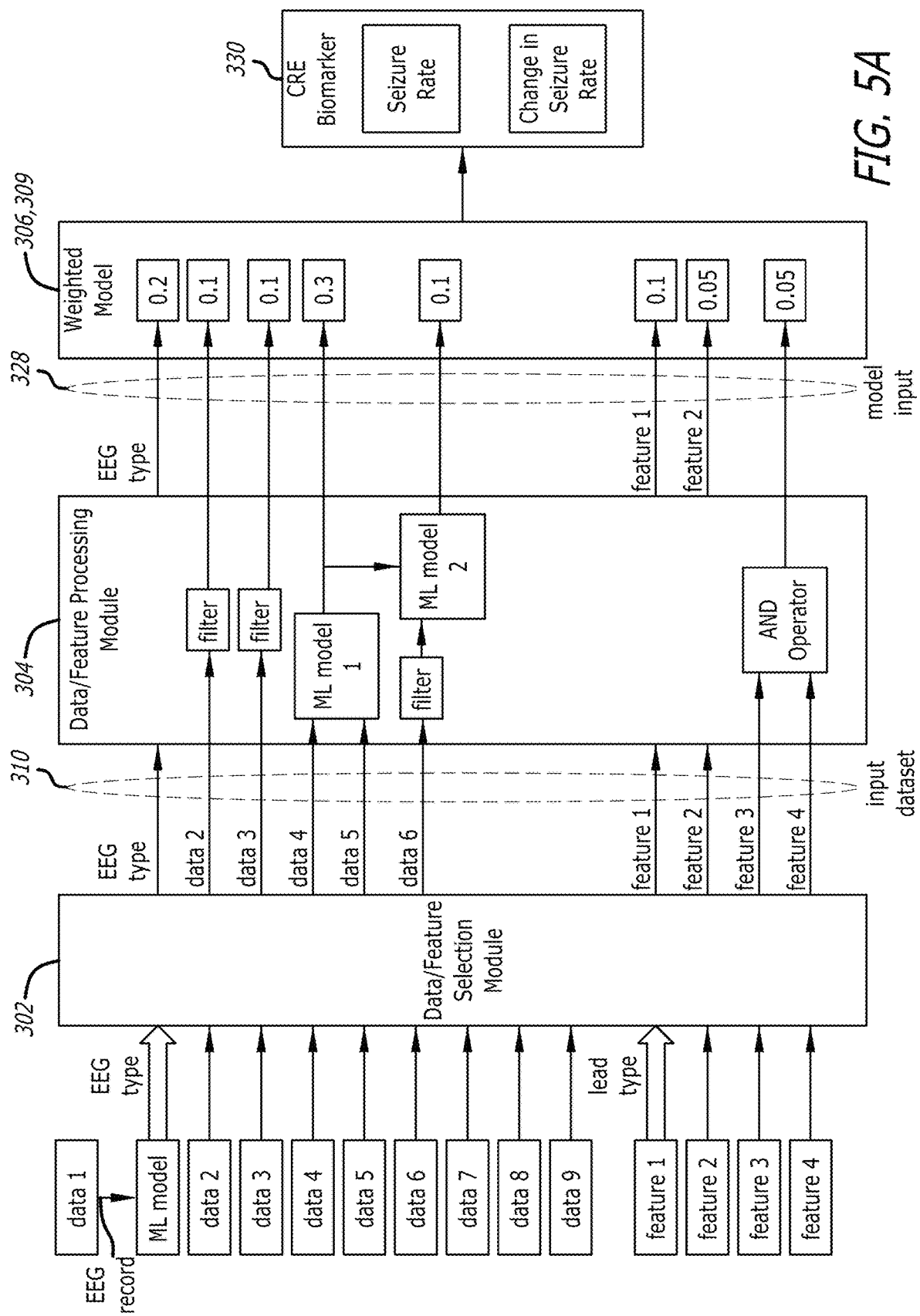
FIGS. 5A and 5B are example process flow graphs of a clinical response estimator illustrating various steps involved in determining a CRE biomarker from a patient-specific dataset.

FIG. 5A is an example process flow graph of a clinical response estimator illustrating various steps involved in determining a CRE biomarker from a patient-specific dataset.

Starting from the left side of the graph, a patient-specific dataset including different data types (data1-data9) from an implanted neurostimulation system and patient features (feature1-feature4) are used as input. In this example, a first key input is derived from data corresponding to EEG records and a second key input is a patient feature corresponding to a type of lead of the implanted neurostimulation system.

Regarding the first key input, it may be derived by comparing EEG records of ictal and interictal activity of the patient with EEG records of ictal and interictal activity from other patients. To this end, a machine-learned model may be applied to the EEG records of the patient and the EEG records of other patients to determine a brain activity type for the subject patient. Examples of machine-learned models for determining brain activity type are disclosed in U.S. Patent Application Publication Nos. 2019/0117978 and 2020/0272857, which are hereby incorporated by reference. As a result of this comparison, it may be determined that the patient's ictal/seizure activity belongs to type 2 and the patient's interictal/non-seizure activity belongs to type 5. As an example, type 2 ictal activity may be low voltage fast type electrographic seizure activity, and type 5 interictal activity may be interictal activity with high levels of theta power.

Regarding the second key input, it corresponds to a type of lead of the implanted neurostimulation system. For example, the lead type for the subject patient may be bilateral depth leads.

Based on these two key inputs (EEG type and lead type), the clinical response estimator determines to use EEG activity type, data2-data6 and feature1-feature4 as the input dataset 310 for determining the CRE biomarker, while data7-data9 are not used.

The key inputs also determine how the data and features in the input dataset 310 are processed by the data/feature processing module 304 to provide the model inputs 328 to the clinical response estimator module 306. In this example, based on the key inputs: 1) EEG activity type passes through the data/feature processing module and is provided as a model input to a CRE model corresponding to a weighted model, 2) data2 and data 3 are respectively filtered and provided as model inputs to the CRE model, 3) a level 1 machine-learned model is applied to data4 and data5 and the output is provided as a model input to the CRE model, 4) data6 is filtered and a level 2 machine-learned model is applied to filtered data6 and to the output of the level 1 machine-learned model, and the output of the level 2 machine-learned model is provided as a model input to the CRE model, 5) feature1 and feature2 are provided as model inputs to the CRE model, and 6) an AND operation is performed between the feature3 and feature4 and the result is provided as a model input to the CRE model. The filter operations mentioned above may refer to the extracting of spectral power in specific frequency bands.

Figure 5B:
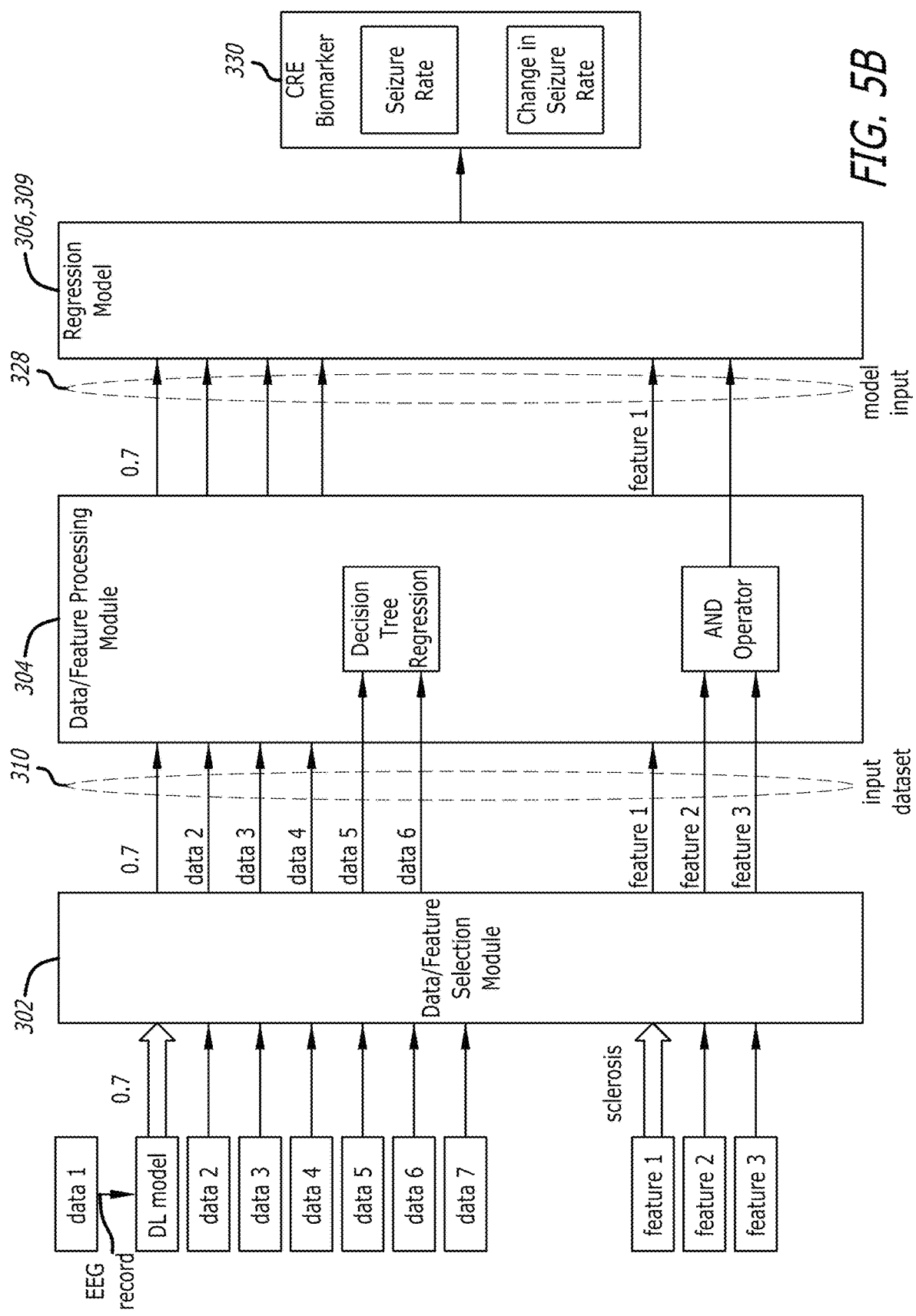

FIG. 5B is a process flow graph of a clinical response estimator illustrating various steps involved in determining a CRE biomarker from a patient-specific dataset.

Starting from the left side of the graph, a patient-specific dataset including different data types (data1-data7) from an implanted neurostimulation system and patient features (feature1-feature3) are used as input. In this example, a first key input is derived from data corresponding to EEG records and a second key input is a patient feature corresponding to a brain abnormality, e.g., sclerosis, of the patient.

Regarding the first key input, it may be derived by passing EEG records of the patient through a trained deep learning model. The deep learning model may be a regression model trained on data from other patients which assigns a value between 0 and 1 based on the activity in the EEG record. For this patient, assume that the deep learning model assigns a value of 0.7 for the patient's EEG record. Thus, the first key input is the value 0.7.

Regarding the second key input, it corresponds to a brain abnormality of the patient. For example, the brain abnormality may be sclerosis.

Based on these two key inputs (0.7 and sclerosis), the clinical response estimator determines to use 0.7, data2-data6 and feature1-feature3 as the input dataset 310 for determining the CRE biomarker, while data7 is not used. In this example, data2-data6 correspond respectively to spike rate, high gamma power, long episode rate, long train events, delta power, data7 corresponds to theta power, and feature2-feature3 correspond respectively to sex and age.

The key inputs also determine how the data and features in the input dataset 310 are processed by the data/feature processing module 304 to provide the model inputs 328 to the clinical response estimator module 306. In this example, based on the key inputs: 1) 0.7 and data2-data4 (spike rate, high gamma power, long episode rate) pass through the data/feature processing module and are provided as model inputs to a CRE model corresponding to a regression model, 2) data5 (long train events) and data6 (delta power) are used as inputs to a decision regression model and the output is provided as a model input to the CRE model, 3) feature1 (sclerosis) passes through the data/feature processing module and is provided as a model input to a CRE model, and 4) an AND operation is performed between feature2 (gender) and feature3 (age) and the result is provided as a model input to the CRE model.

In the foregoing example, the data and features included in an input dataset depend on data availability. For example, if the key inputs determine an input dataset that includes spike rate, but there are no EEG records of the patient available for computing the spike rate, a different derived data type such as the circadian cycle of brain activity may be used instead of the spike rate. The circadian cycle may be computed either from pH levels or long episode EEG records, or from the long episode rate. In the case of a CRE model that is a weighted model, the weights given to different model inputs may also be adjusted.

Figure 6:
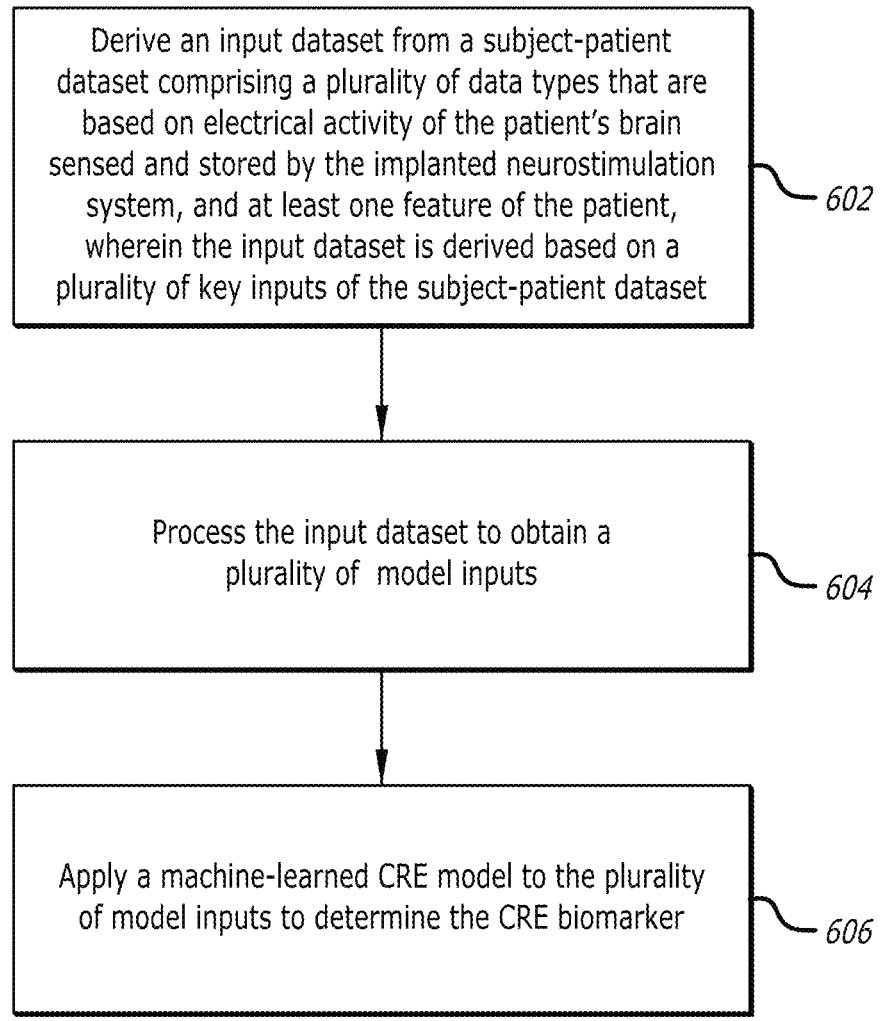
FIG. 6 is a flowchart of a method of determining a CRE biomarker of a patient having an implanted neurostimulation system.

FIG. 6 is a flowchart of a method of determining a CRE biomarker of a patient having an implanted neurostimulation system. The method may be enabled and performed by the clinical response estimator described above with reference to FIGS. 3 and 4, and later below with reference to FIG. 7.

At block 602, an input dataset 310 is derived from a subject-patient dataset 308 that includes a variety of data types that are based on electrical activity of the patient's brain sensed and stored by the implanted neurostimulation system, and at least one feature of the patient. With reference to Tables 1 and 2, the subject-patient dataset 308 may include one or more of: a data type that is based on records of electrical activity of the brain, a data type that is based on something other than records of electrical activity of the brain, a feature that is based on patient demographics, a feature that is based on patient diagnoses/treatment, and a feature that is based on the implanted neurostimulation system.

The input dataset 310 is derived based on key inputs of the subject-patient dataset 308. As previously describe, the key inputs may be manually determined by a physician or automatically determined based on the subject-patient dataset. In some embodiments, the key inputs may be determined by applying a machine-learned model to the subject-patient dataset. The machine-learned model may be one of a decision tree, neural network or trained supervised machine learning model that takes in the entire subject-patient dataset and returns a subset corresponding to the key inputs.

As an example, a trained decision tree model may determine that out of twenty inputs (e.g., data types and patient features) from a subject-patient dataset 308, only the lead location and the age of the patient are key inputs. The training of the decision tree model may have been performed previously on a cross-patient dataset. As an example, data from thousands of patients may be used to train a model to estimate an output metric such as patient's clinical seizure rate. As a result of training process, the machine-learned model may identify dependencies in the dataset—for example if the patient is less than 30 years of age and had depth leads, then the lobe of seizure onset is a key input which determines which features and data types are needed to determine the seizure rate. As another example, if the patient has type 5 brain activity and is a female, then the type of lead implanted and power in theta band are the key inputs which determine which features and data types are needed to determine the change in seizure rate.

With reference to Tables 1 and 2, in either case, the key inputs may include one or more of: a data type that is based on records of electrical activity of the brain, a feature that is based on patient demographics, a feature that is based on patient diagnoses/treatment, and a feature that is based on the implanted neurostimulation system. In some embodiments, one of the key inputs may correspond to transformed data. In this case, determining the plurality of key inputs includes transforming a data type into the transformed data. For example, as described above with reference to FIGS. 5A and 5B, EEG records may be transformed into a brain activity type (FIG. 5A) or a numeric value (FIG. 5B). To these ends, a machine-learned model may be applied to the EEG records.

Once the key inputs are determined, the input dataset 310 is determined based on the key inputs. In some embodiments, a machine-learned model is applied to the key inputs to derive the input dataset 310. The machine-learned model may be a deep learning model trained.

At block 604, the input dataset 310 is processed to obtain a plurality of model inputs 328. In some embodiments, a first machine-learned model 305 is applied to a first subset of the input dataset 310 to obtain one or more of the plurality of model inputs. The first machine-learned model 305 is trained on datasets that include data types derived from records of electrical activity of the brain sensed and stored by implanted neurostimulation systems, and classified as ictal records, and exclude data types of records of electrical activity of the brain sensed and stored by implanted neurostimulation systems and classified as interictal records.

In some embodiments, a second machine-learned model 307 is applied to a second subset of the input dataset 310 to obtain one or more of the plurality of model inputs 328. The second machine-learned model 307 is trained on datasets that include data types derived from records of electrical activity of the brain sensed and stored by implanted neurostimulation systems, and classified as interictal records, and exclude data types of records of electrical activity of the brain sensed and stored by implanted neurostimulation systems and classified as ictal records.

In some embodiments, additional machine-learned models may be respectively applied to additional subsets of the input dataset 310 of obtain one or more of the plurality of model inputs 328.

In some embodiments, the input dataset 310 is processed by determining one or more transformations that are performed on one or more data types to obtain one or more corresponding model inputs. With references to FIGS. 5A and 5B, example transformations include one or a combination of: combining a plurality of data types, combining a plurality of patient features, apply a plurality of data types to a convolutional neural network, apply a machine-learned model to one or more of a plurality of data types, and passing a component as a model input. A transformation may include a combination of the foregoing transformations, such as a series combination. For example, a machine-learned model may be applied to a pair of data types, followed by a combining operation that ADDs the output of the model and a data type.

At block 606, a machine-learned CRE model 309 (also referred to as an ensemble machine-learned model or final model) is applied to the plurality of model inputs 328 to determine the CRE biomarker 330. The machine-learned CRE model 309 is trained on datasets across a patient population. To this end, in some embodiments the CRE model 309 is trained on model inputs 328 corresponding to outputs of other machine-learned models, e.g., the above described first machine-learned model 305 and the second machine-learned model 307.

In some embodiments, the subject-patient dataset 308 and the input dataset 310 derived therefrom include a data type that is sensed and stored over a time period, and that is characterized by a value. The data type may be one of the key inputs. For example, with reference to FIG. 9C, a key input may be the LE count. In this case, the processing (block 604) and applying (block 606) of the method of FIG. 6 are performed a number of times for the time period to determine a corresponding number of CRE biomarkers. Having this information, the CRE biomarker 330 may be displayed as a function of time over the time period, together with the values of the at least one data type. Also, an occurrence of an event of interest during the time period may be displayed. For example, with reference to FIG. 9C, a vertical line may indicate a device programming change.

Figure 7:
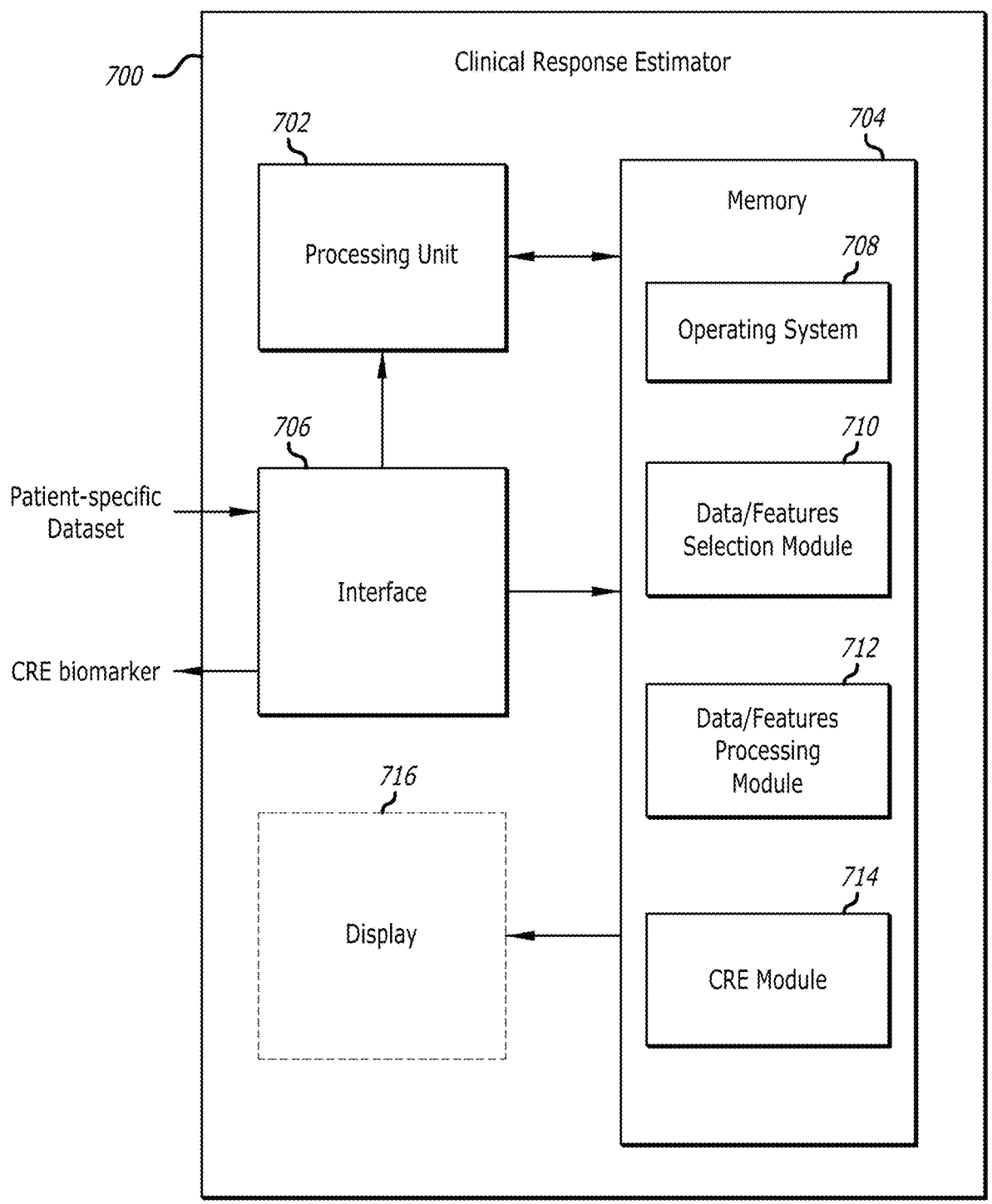
FIG. 7 is a block diagram of an apparatus corresponding to a clinical response estimator.

FIG. 7 is a schematic block diagram of an apparatus 700 corresponding to the clinical response estimator 204 of FIG. 3. The apparatus 700 is configured to execute instructions related to the processes described above with reference to FIGS. 3-6. The apparatus 700 may be embodied in any number of processor-driven devices, including, but not limited to, a server computer, a personal computer, one or more networked computing devices, an application-specific circuit, a minicomputer, a microcontroller, and/or any other processor-based device and/or combination of devices.

The apparatus 700 may include one or more processing units 702 configured to access and execute computer-executable instructions stored in at least one memory 704. The processing unit 702 may be implemented as appropriate in hardware, software, firmware, or combinations thereof. Software or firmware implementations of the processing unit 702 may include computer-executable or machine-executable instructions written in any suitable programming language to perform the various functions described herein. The processing unit 702 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The apparatus 700 may also include a chipset (not shown) for controlling communications between the processing unit 702 and one or more of the other components of the apparatus 700. The processing unit 702 may also include one or more application-specific integrated circuits (ASICs) or application-specific standard products (ASSPs) for handling specific data processing functions or tasks.

The memory 704 may include, but is not limited to, random access memory (RAM), flash RAM, magnetic media storage, optical media storage, and so forth. The memory 704 may include volatile memory configured to store information when supplied with power and/or non-volatile memory configured to store information even when not supplied with power. The memory 704 may store various program modules, application programs, and so forth that may include computer-executable instructions that upon execution by the processing unit 702 may cause various operations to be performed. The memory 704 may further store a variety of data manipulated and/or generated during execution of computer-executable instructions by the processing unit 702.

The apparatus 700 may further include one or more interfaces 706 that may facilitate communication between the apparatus and one or more other apparatuses. For example, the interface 706 may be configured to obtain patient-specific dataset for a patient from a patient's implanted neurostimulation system 202 or a database 206. The interface 706 is also configured to transmit or send CRE biomarkers and values for data types to a network 208 server. Communication may be implemented using any suitable communications standard. For example, a LAN interface may implement protocols and/or algorithms that comply with various communication standards of the Institute of Electrical and Electronics Engineers (IEEE), such as IEEE 802.11.

The memory 704 may store various program modules, application programs, and so forth that may include computer-executable instructions that upon execution by the processing unit 702 may cause various operations to be performed. For example, the memory 704 may include an operating system module (O/S) 708 that may be configured to manage hardware resources such as the interface 706 and provide various services to applications executing on the apparatus 700.

The memory 704 stores additional program modules such as a data/feature selection module 710, a data/feature processing module 712, a CRE module 714, and an optional a display module 716. These modules 710, 712, 714, 716 includes computer-executable instructions that when executed by the processing unit 702 cause various operations to be performed, such as the operations described immediately above and earlier with reference to FIGS. 3-6. For example, the data/feature selection module 710 is configured to derive an input dataset from a subject-patient dataset comprising a plurality of data types that are based on electrical activity of the patient's brain sensed and stored by the implanted neurostimulation system, and at least one feature of the patient, wherein the input dataset is derived based on a plurality of key inputs of the subject-patient dataset. The data/feature processing module 712 is configured to process the input dataset to obtain a plurality of model inputs. The CRE module 714 is configured to apply a machine-learned clinical response estimator model to the plurality of model inputs to determine the CRE biomarker, wherein the machine-learned clinical response estimator is trained on datasets across a patient population. The display module 716 is configured to receive time stamped information corresponding to one or more of values of CRE biomarkers, events of interest, and values of data types, and to process the information and render a graphical display of the information as a function of time.

The apparatus 700 and modules disclosed herein may be implemented in hardware or software that is executed on a hardware platform. The hardware or hardware platform may be a general-purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Offline Clinical Response Estimator

As mentioned above with reference to the method of FIG. 6, the clinical response estimator can determine CRE biomarkers over a time period and display this information as a function of time. These displays can inform a physician or caregiver about a patient's response to an event of interest. For example, with reference to FIG. 8, physicians and caregivers may want to know how an event of interest affects a patient's response to treatment. In the case of a patient having an implanted neurostimulation system and being treated for epilepsy, a physician may want to know if the patient is having more or less electrographic events after an occurrence of one of the following events of interest: 1) a neurostimulator implant or replacement, 2) an operational change to an implanted neurostimulation system, such as changes to detection parameters and/or stimulation parameters, 3) a change to the patient's anti-seizure medication dosage, or 4) a change in lifestyle patterns such as sleep or diet habits.

In accordance with disclosed embodiments, data types provided by the neurostimulation system implanted in the patient, and patient features, e.g., patient demographics, are used to assess and inform on the effect of an event of interest. To this end, the clinical response estimator disclosed herein is configured to periodically derive a clinical response estimate (CRE) biomarker based on an input dataset and model inputs obtained based on the input dataset. The input dataset may be derived and processed as described above with reference to FIG. 3-6. The CRE biomarkers may be derived over a time encompassing a time period before the event of interest and a time period after the event of interest. A change or trend in the CRE biomarker over this time may inform the physician of the effect of the event of interest.

For example, and with additional reference to FIG. 3, in cases where a CRE biomarker since a last event of interest is desired, the input dataset 310 derived and processed by the clinical response estimator 204 includes data types and features from a time window before the event of interest and a time window after the event of interest. To this end, to assist in processing information relevant to each respective window of time a data type, e.g., spike rate/minute, includes a binary flag (example 1 or 0) that indicates if the spike rate/minute measure is from the period before or after the event of interest. An equal number of days before and after the event of interest may additionally be used in this case. For example, if the event of interest happened 60 days ago, spike rate/minute in the 60 days since the event of interest will be used (with a flag 1 to indicate that this data is captured after the event), and spike rate/minute 60 days before the event (with a flag of 0) will be used.

In the offline implementation scenario, a physician may log into a website and be presented with an image that displays trends and values of different data type before and after one or more events of interest, together with a trend and value of a CRE biomarker determined by a clinical response estimator. Example display images are shown in FIGS. 9A-9D.

Figure 9A:
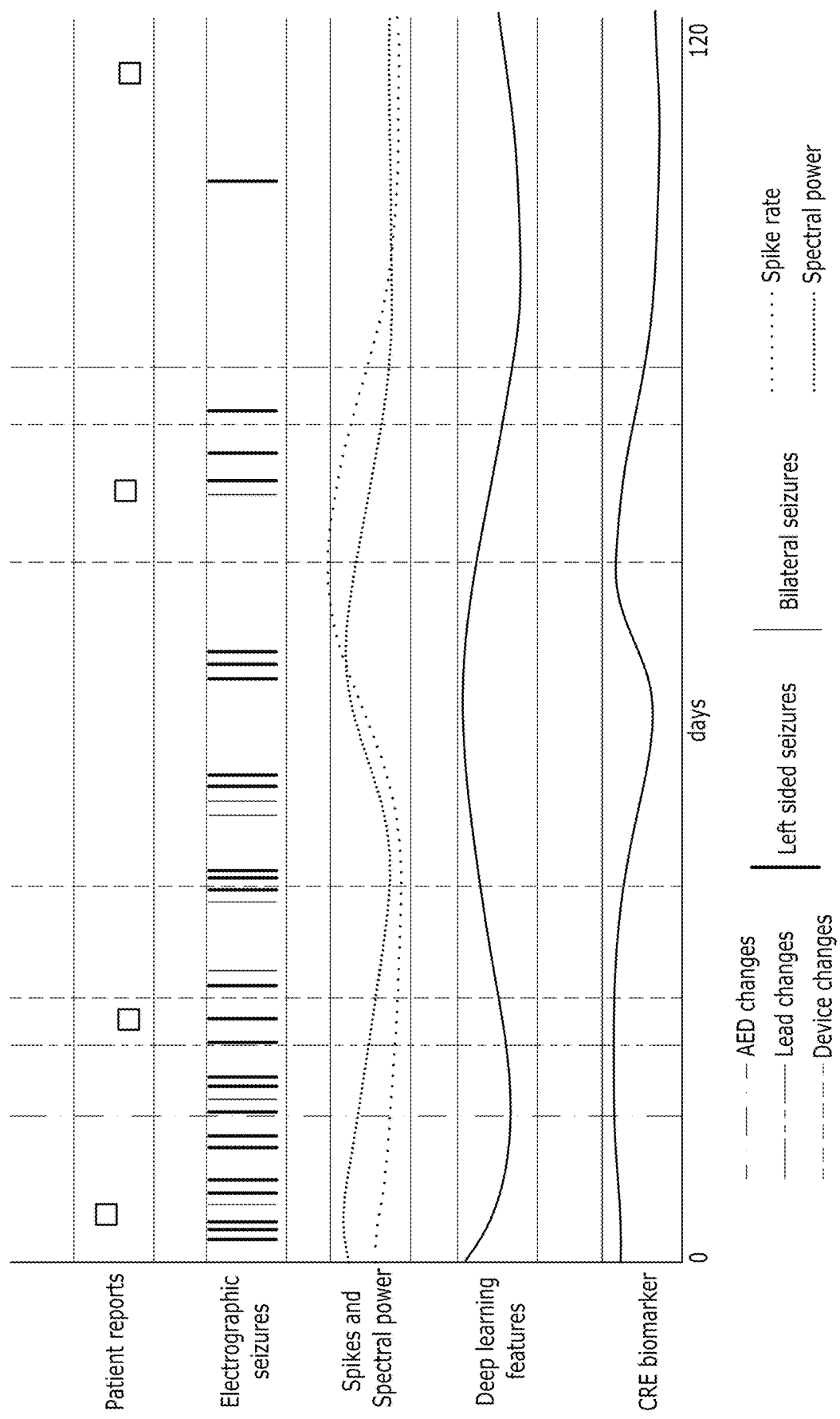
FIG. 9A is an example presentation of clinical response information for a patient as a function of time, wherein different events of interest are indicated together with a CRE biomarker.

FIG. 9A is an example presentation of clinical response information for a patient having an implanted neurostimulation system. The information is presented as a function of time, wherein different events of interest (e.g., anti-epileptic drug (AED) changes, device lead changes, device programming changes) are indicated together with a CRE biomarker. A clinical response estimator configured in accordance with disclosed embodiments, determined a CRE biomarker for the patient based on a patient-specific dataset including various data types and patient features of the patient. The range or window of time selected for processing by the clinical response estimator and display is the most recent 120 days. The clinical response estimator selected an input dataset from the patient-specific dataset and processed the input dataset to determine a CRE biomarker. A subset of the input dataset, including five data types and one patient feature is visualized. The subset includes patient seizure reports, electrographic seizure classifications (e.g., left-sided seizure, bilateral seizure), spike rate, spectral power measures, and output features of a deep learning model. The display of FIG. 9A informs the physician, for example, that after the most recent device programming change: (1) the patient has a seizure rate of 3/month (70% certainty); and (2) that the patient has a 20% reduction in seizures compared to the previous epoch (65% certainty). The downward trend in the CRE biomarker following the second most device programming change indicates that the patient's outcome is improving.

Figure 9B:
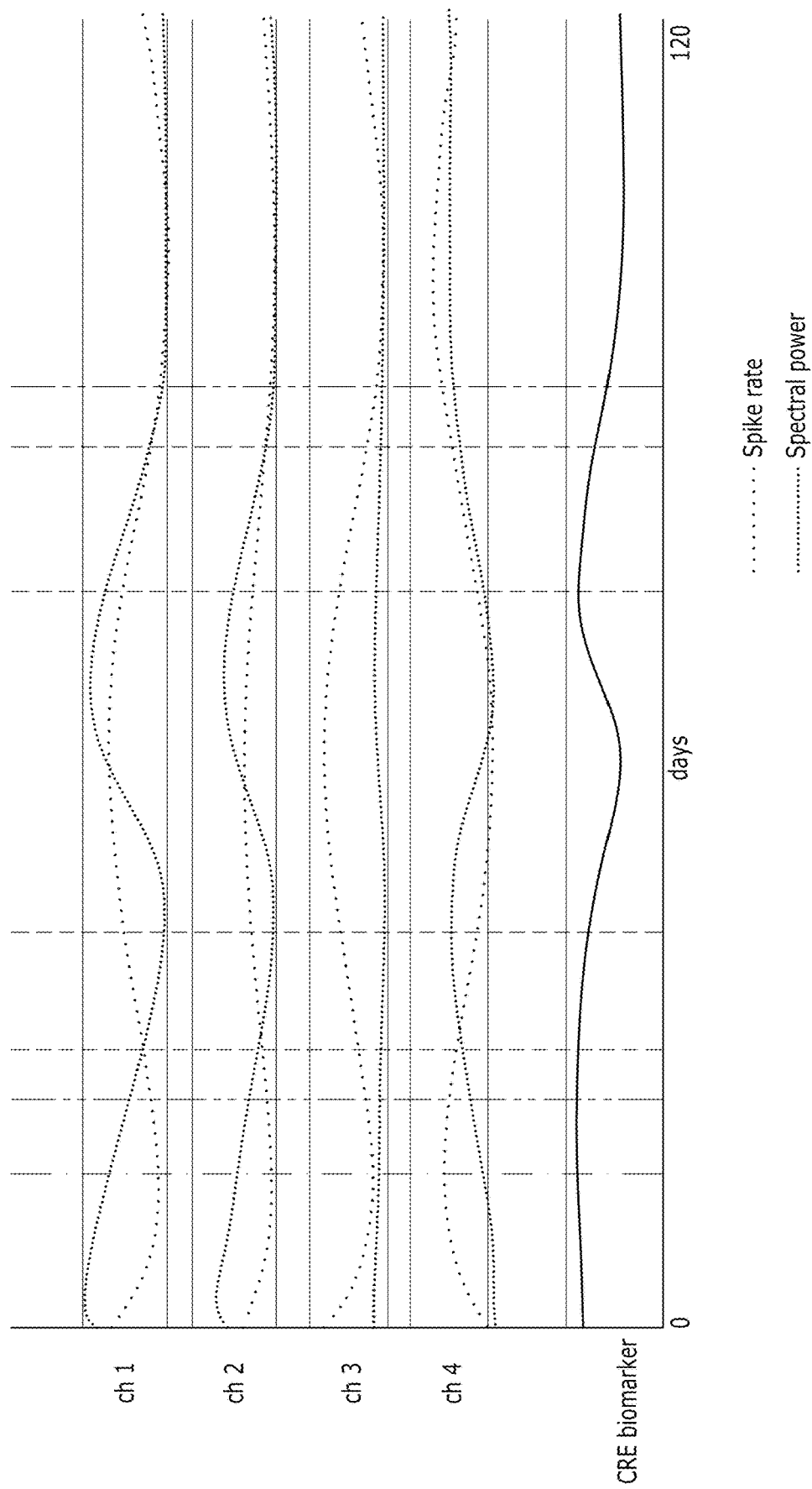
FIG. 9B is an example presentation of clinical response information for a patient as a function of time, wherein sensing channels of an implanted neurostimulation system are individually displayed together with a CRE biomarker.

FIG. 9B is an example presentation of clinical response information for a patient having an implanted neurostimulation system. The information is presented as a function of time, wherein select data types for each sensing channel of an implanted neurostimulation system are individually displayed together with a CRE biomarker. The range or window of time selected for the display is the most recent 120 days. Similar to the process of FIG. 9A, the clinical response estimator selected an input dataset from the patient-specific dataset and processed the input dataset to determine the CRE biomarker. A subset of the input dataset, including two data types is visualized for each sensing channel. The subset includes spike rate, spectral power measures. The display of FIG. 9B informs the physician, for example, how the spike rate and spectral power changed in the patient. The physician may use this information to determine the next treatment steps in the patient. For example, if the display shows that the spike rate increased in the patient, the physician may decide to treat the patient with an anti-seizure medication whose mechanism of action is to reduce the occurrence of interictal spikes.

Figure 9C:
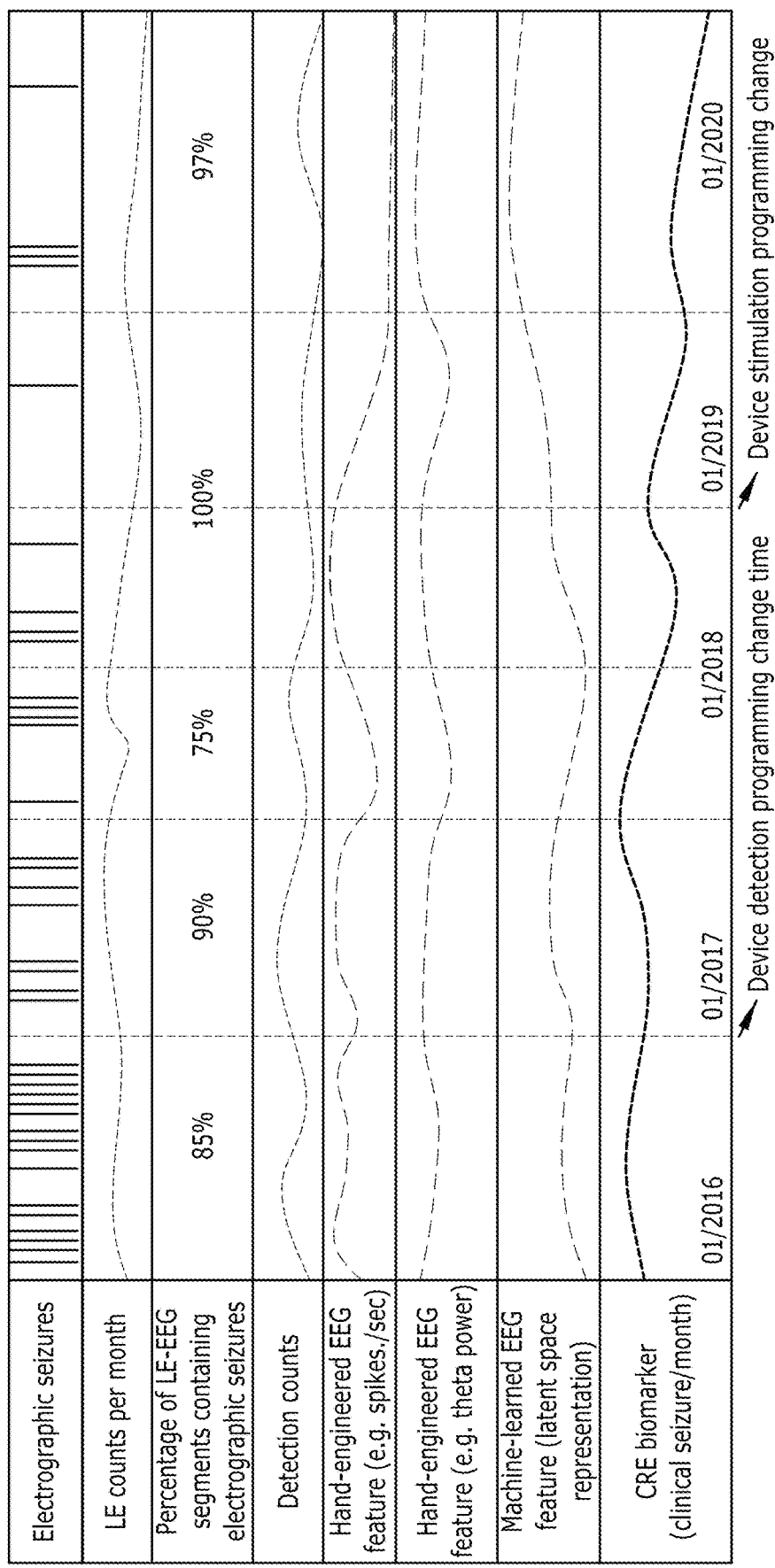
FIG. 9C is an example is presentation of clinical response information for a patient as a function of time, wherein different events of interest are indicated together with key inputs and a CRE biomarker.

FIG. 9C is an example presentation of clinical response information for a patient having an implanted neurostimulation system. The information is presented as a function of time, showing a longitudinal plot of several model inputs and the resulting CRE biomarker (e.g., estimate of clinical seizure rate) over a period of several years that includes two events of interest, e.g., two programming change epochs. The model inputs in the display may correspond to key inputs that were determined to be important for the CRE model prediction.

Figure 9D:
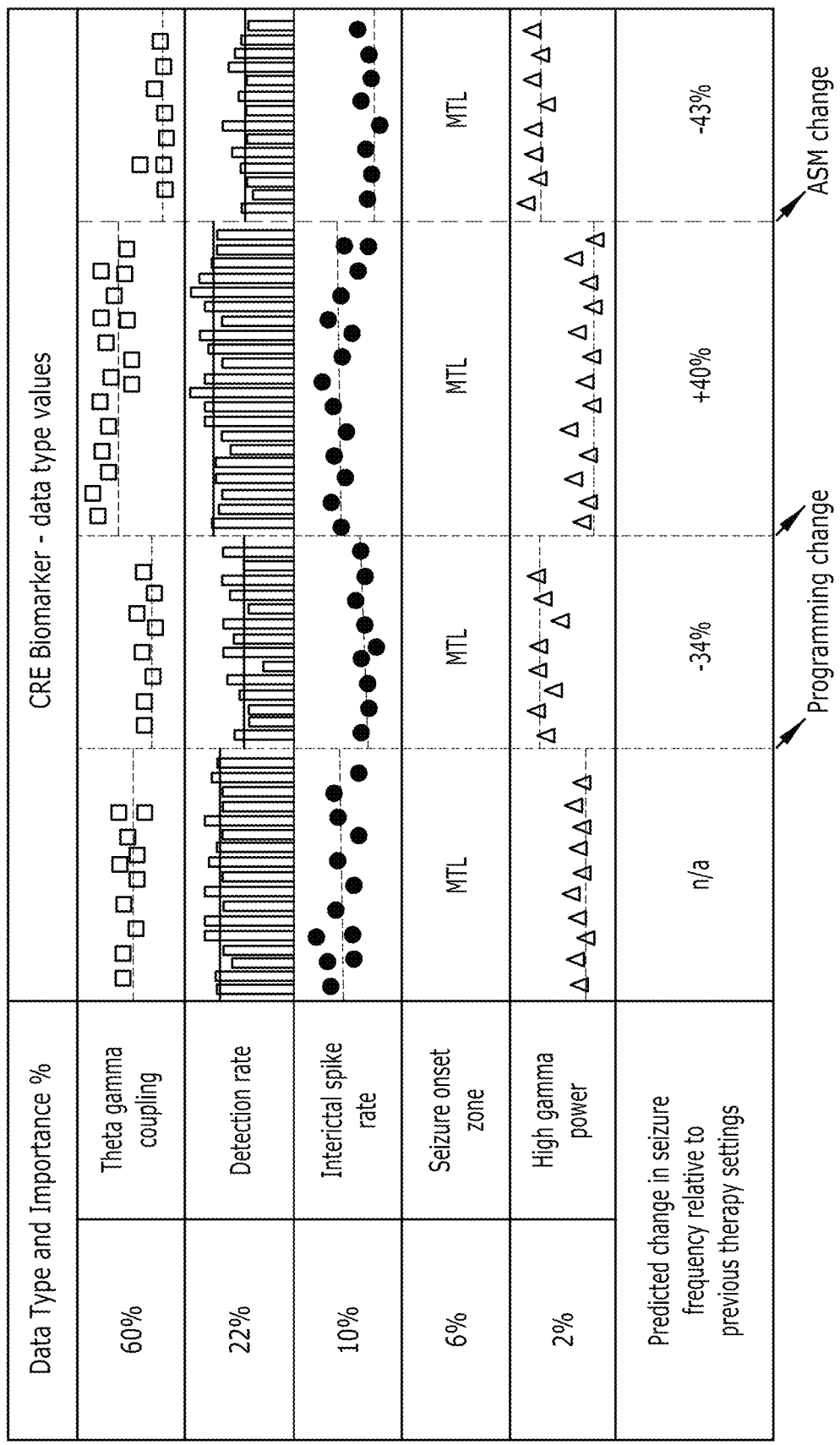
FIG. 9D is an example is presentation of clinical response information for a patient as a function of time, wherein different events of interest are indicated together with key inputs and a CRE biomarker.

FIG. 9D is an example presentation of clinical response information for a patient having an implanted neurostimulation system. The information is presented as a function of time, showing a longitudinal plot of several model inputs and the resulting CRE biomarker (e.g., change in seizure frequency) over a period that includes two events of interest, e.g., a programming change, and a change in antiseizure medication (ASM). The model inputs in the display may correspond to the key inputs that were determined to be important for the CRE model prediction. A measure of importance for each model input is also displayed. The importance is in relation to the machine-learned CRE model.

Figure 8:
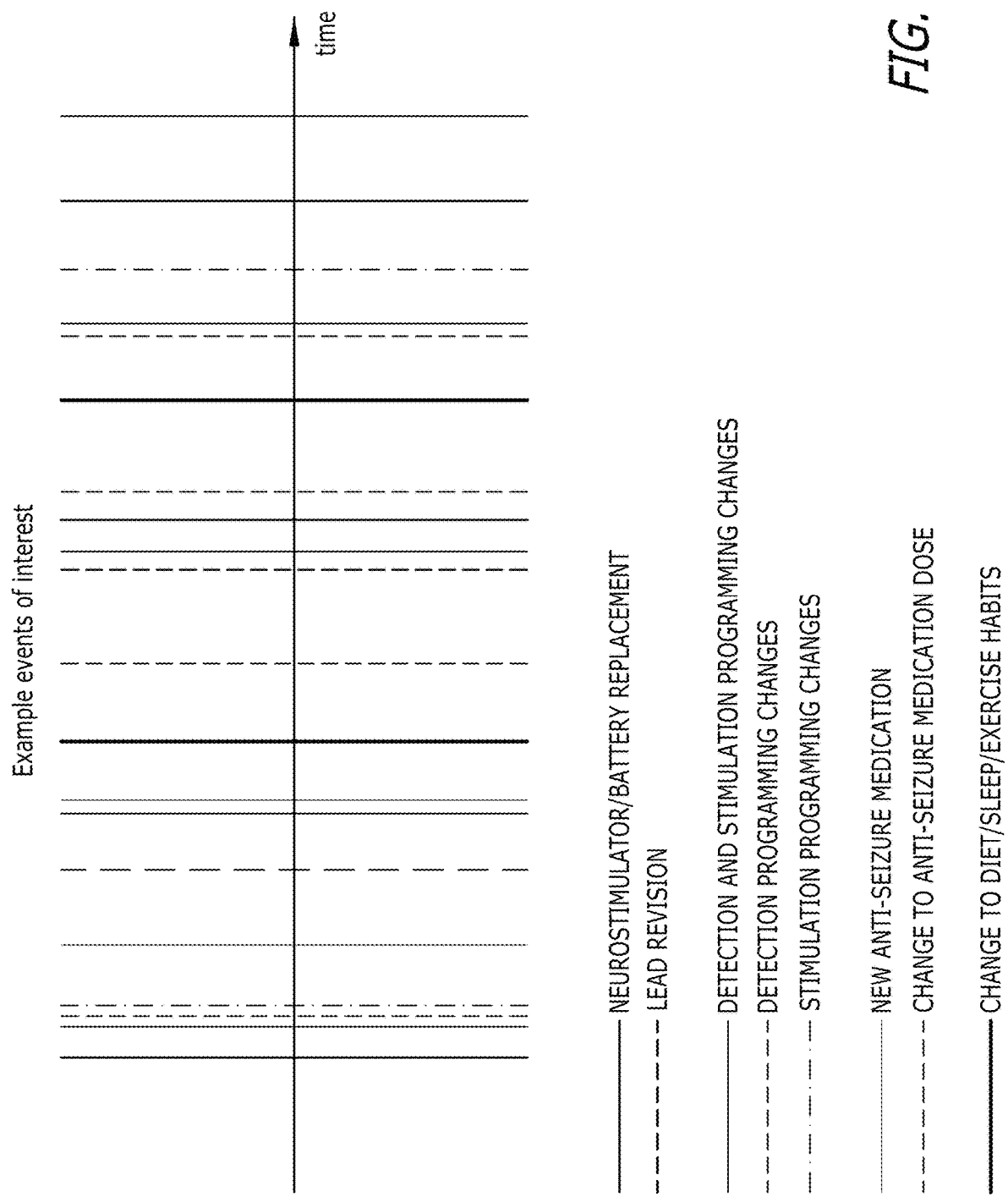
FIG. 8 is a timeline with example events of interest that may trigger a determining of a CRE biomarker.
Figure 10:
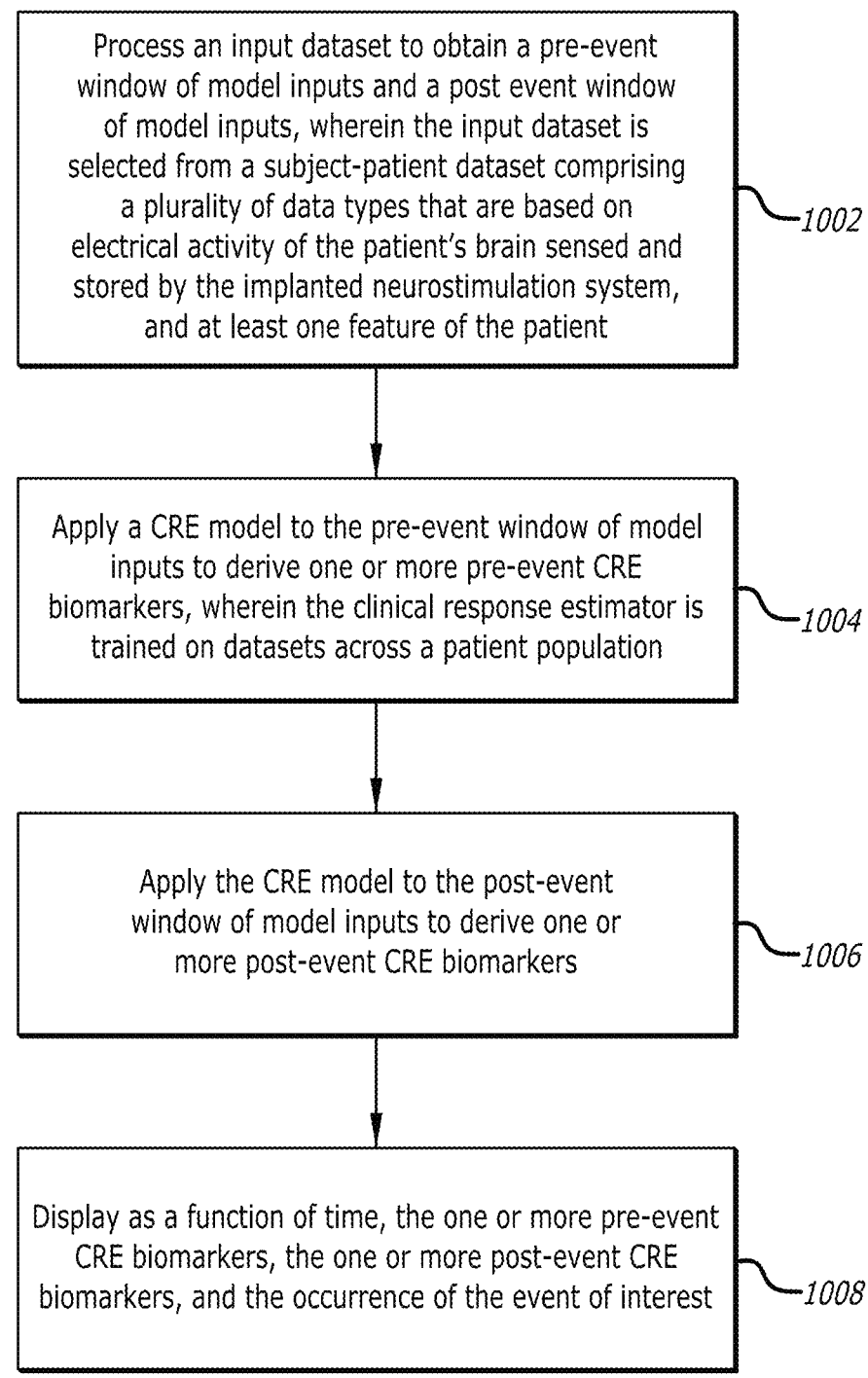
FIG. 10 is a flowchart of a method of informing of a clinical response of a patient as a function of an event of interest.

FIG. 10 is a flowchart of a method of informing of a clinical response of a patient as a function of an event of interest that occurred at an associated time. The method may be enabled and performed by an offline embodiment of the clinical response estimator described above with reference to FIGS. 3, 4, and 7. With reference to FIG. 8, the event of interest may be one of a replacement of a component (e.g., battery) of the IMD, a change in operation of the IMD (e.g., lead revision, detection and/or stimulation programming changes, a change in therapy for the patient (new anti-seizure medication or change in dose), a change in patient habits (change to diet, sleep, exercise).

At block 1002, an input dataset 310 is processed to obtain a pre-event window of model inputs and a post-event window of model inputs. The input dataset 310 is selected from a subject-patient dataset 308 that includes various data types and at least one feature of the patient in the same manner as described above with reference to FIGS. 3-7. To this end, the data/feature processing module 304 is configured to process the input dataset, while the data/feature selection module 302 is configured to select the input dataset 310 from a subject-patient dataset 308.

In some embodiments, the input dataset 310 is processed to obtain a pre-event window of model inputs and a post-event window of model inputs by applying a first machine-learned model 305 to a first subset of the input dataset 310 to obtain one or more of the plurality of model inputs 328. The first machine-learned model 305 is trained on datasets that include data types derived from records of electrical activity of the brain sensed and stored by implanted neurostimulation systems, and classified as ictal records, and exclude data types of records of electrical activity of the brain sensed and stored by implanted neurostimulation systems and classified as interictal records.

In some embodiments, the input dataset 310 is processed to obtain a pre-event window of model inputs and a post-event window of model inputs by applying a second machine-learned model 307 to a second subset of the input dataset to obtain one or more of the plurality of model inputs 328. The second machine-learned model 307 is trained on datasets that include data types derived from records of electrical activity of the brain sensed and stored by implanted neurostimulation systems, and classified as inter-ictal records, and exclude data types of records of electrical activity of the brain sensed and stored by implanted neurostimulation systems and classified as ictal records.

In some embodiments, additional machine-learned models may be respectively applied to additional subsets of the input dataset 310 of obtain one or more of the plurality of model inputs 328

At block 1004, an ensemble machine-learned model 309 is applied to the pre-event window of model inputs to derive one or more pre-event CRE biomarkers. At block 1006, the ensemble machine-learned model 309 is applied to the post-event window of model inputs to derive one or more post-event CRE biomarkers. The ensemble machine-learned model 309 may be the machine-learned CRE model described above with reference to FIGS. 3-7. To this end, in some embodiments the ensemble machine-learned model 309 is trained on model inputs corresponding to outputs of other machine-learned models, e.g., the above described first machine-learned model and the second machine-learned model.

At block 1008, the one or more pre-event CRE biomarkers, the one or more post-event CRE biomarkers, and the time of occurrence of the event of interest are displayed as a function of time. In some embodiments, the input dataset 310 includes at least one data type (e.g., event detections, detection rate, spike count, spike rate, spectral power, deep learning feature, LE counts, etc.) that is sensed and stored over a time period, and that is characterized by a value, and the values of the at least one data type are displayed as a function of time. The input dataset 310 may also include a patient features (e.g., patient-reported seizure) stored over a time period. To this end, the apparatus 700 of FIG. 7 includes a display 716 that is coupled with the memory 704 to receive information corresponding to the pre-event CRE biomarkers, the post-event CRE biomarkers, the time of occurrence of the event of interest, values of the at least one data type, and values of the patient feature. The display 716 is configured to process the information and render a graphical display of the information.

Online Clinical Response Estimator

A clinical response estimator 204 may be incorporated in the implantable neurostimulation system 202 and used to adjust an operation of the system. Such an application of the clinical response estimator 204, referred to as an "online" application, may function in real time using a patient-specific dataset maintained onboard the implantable neurostimulation system 202. For example, if the CRE biomarker determined by the clinical response estimator 204 using the patient-specific dataset suggests that the patient is not responding to current stimulation therapy, the implantable neurostimulation system 202 may automatically change one or more of the detection parameters and stimulation parameters of the system. For example, the detection parameters and stimulation parameters may be adjusted using an algorithm such as Bayesian Optimization, as described in U.S. Patent Application Publication No. 2020/0272857, which is hereby incorporated by reference. In this way, the implantable neurostimulation system 202 can search through the large detection and stimulation parameter space and automatically find the optimal settings for individual patients.

Figure 11:
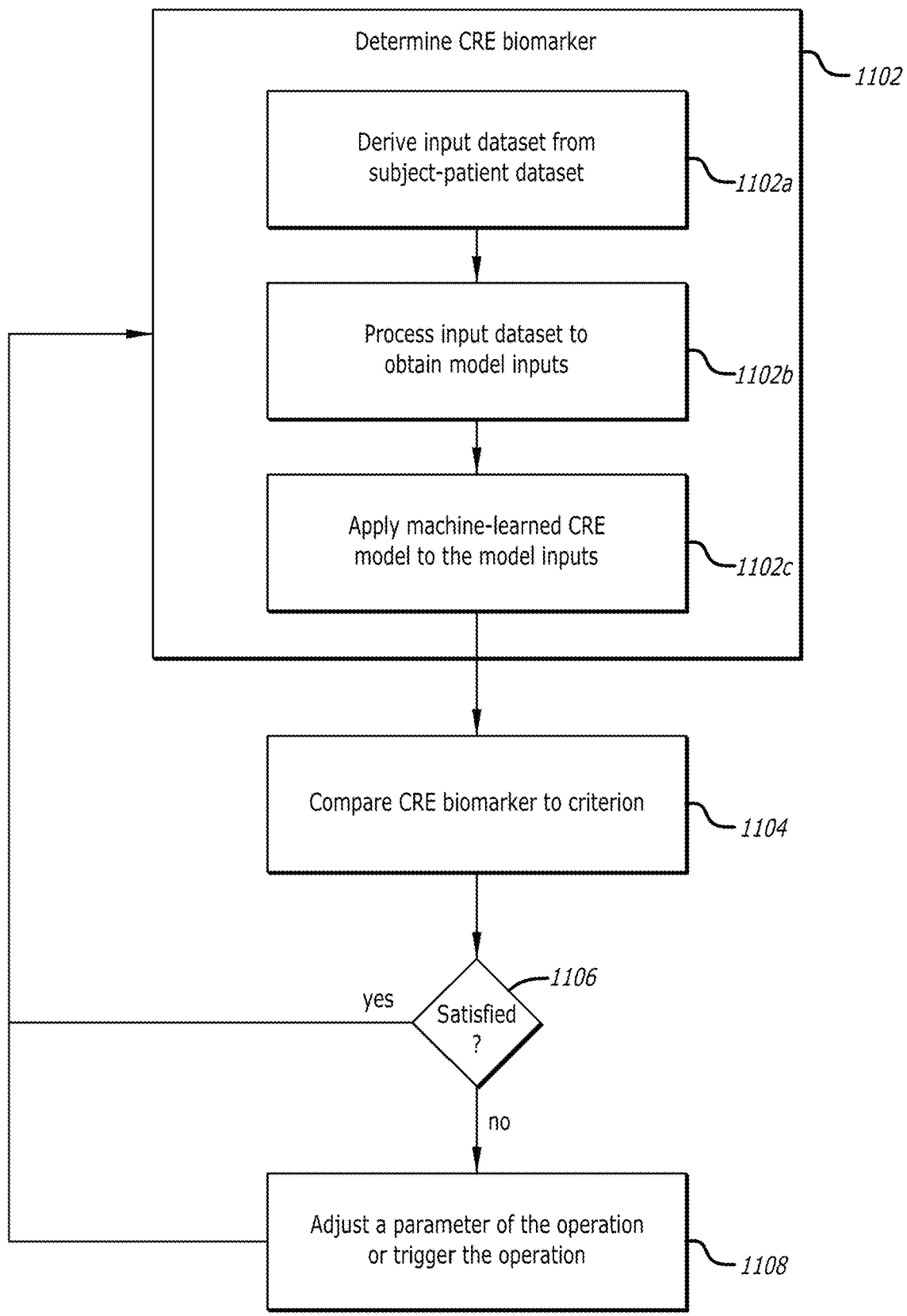
FIG. 11 is a flowchart of a method modifying an operation of an implanted neurostimulation system having an online or built-in clinical response estimator.

FIG. 11 is a flowchart of a method of modifying an operation of an implanted neurostimulation system of a patient in real time. The method may be enabled and performed by an implantable neurostimulation system, as described later below with reference to FIGS. 12 and 21, that has an online or built-in clinical response estimator 304 as described above with reference to FIG. 3.

At block 1102, a clinical response estimate (CRE) biomarker 330 is determined by the implanted neurostimulation system. The CRE biomarker 330 may be, for example, a value indicative of an estimated seizure rate or an estimated change in seizure rate. The CRE biomarker 330 for example may be an average of the interictal spike rate and long episode rate in the patient. The CRE biomarker 330 may be determined continuously by the implanted neurostimulation system or periodically based on a patient-specific dataset on board the implanted neurostimulation system.

The following are performed by the implanted neurostimulation system to determine the CRE biomarker:

At block 1102a, an input dataset 310 is derived from a subject-patient dataset 308 that includes various data types that are based on electrical activity of the patient's brain that is sensed and stored as EEG records by the implanted neurostimulation system, and at least one feature of the patient. The subject-patient dataset 308 may be stored in the implanted neurostimulation system and may be continuously updated in real time by the system. The input dataset 310 is derived based on a plurality of key inputs of the subject-patient dataset. The input dataset 310 may be derived in the same manner as described above with reference to FIGS. 3-7. Accordingly, the details of deriving an input dataset are not repeated here.

At block 1102*b*, the input dataset 310 is processed to obtain a plurality of model inputs 328. The input dataset 310 may be processed to obtain model inputs 328 in the same manner as described above with reference to FIGS. 3-7. Accordingly, the details of obtaining model inputs from an input dataset are not repeated here.

At block 1102*c*, a machine-learned clinical response estimator (CRE) model 309 is applied to the plurality of model inputs 328 to determine the CRE biomarker 330. The machine-learned CRE model 309 is trained on datasets across a patient population. The machine-learned CRE model 309 may be the same model as described above with reference to FIGS. 3-7. Accordingly, the details of the CRE model are not repeated here.

At block 1104, the CRE biomarker 330 is compared to a criterion. For example, in cases where the CRE biomarker 330 is a value indicative of an estimated seizure rate, the criterion may be a threshold value, such as 50%, at or below which the CRE biomarker is preferred to be (i.e., a value which indicates that the patient is having a low clinical seizure rate). In cases where the CRE biomarker 330 is a value indicative of estimated change in seizure rate, the criterion may be a threshold value, such as a 50% increase, below which the CRE biomarker is preferred to be.

Figure 12:
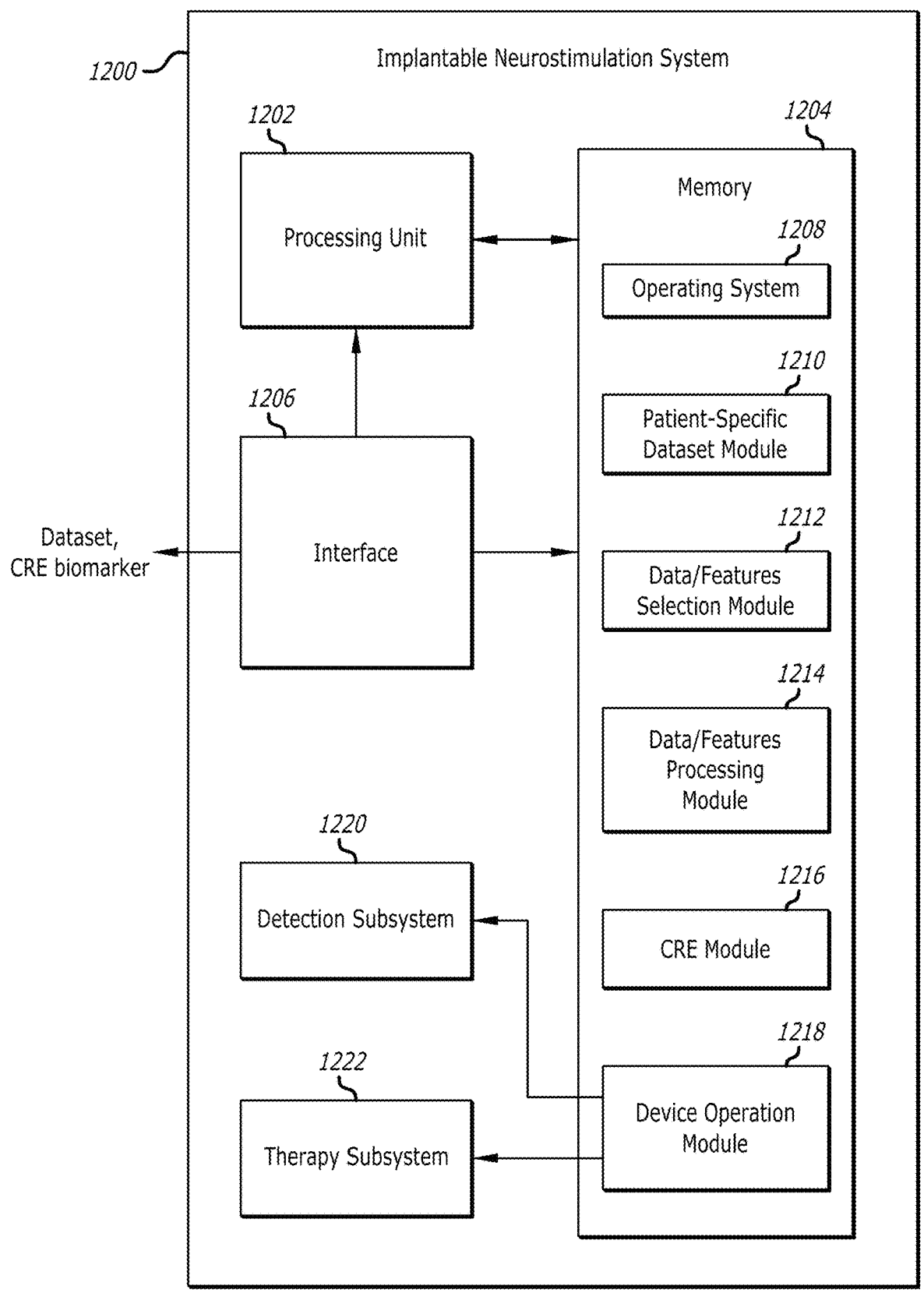
FIG. 12 is a schematic block diagram of an apparatus corresponding to an implantable neurostimulation system having an online or built-in clinical response estimator.
Figure 13A:
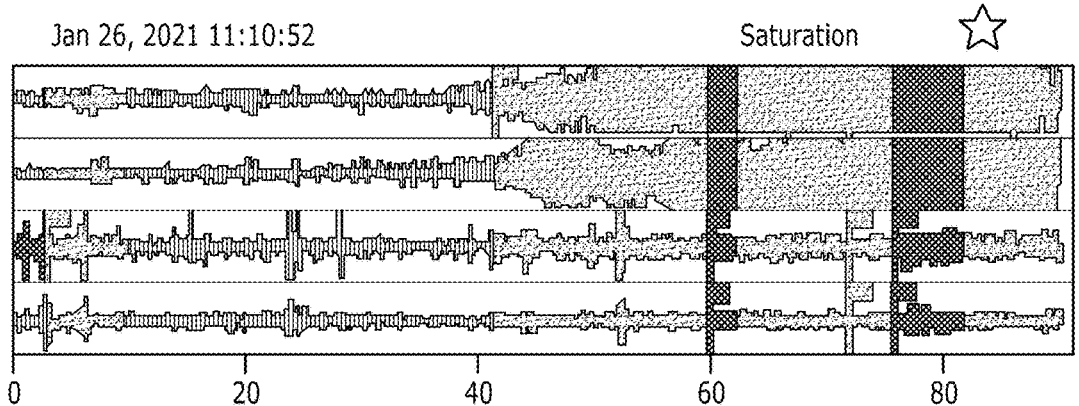
FIGS. 13A-13I are schematic illustrations of time-series waveforms representations of EEG records.
Figure 13B:
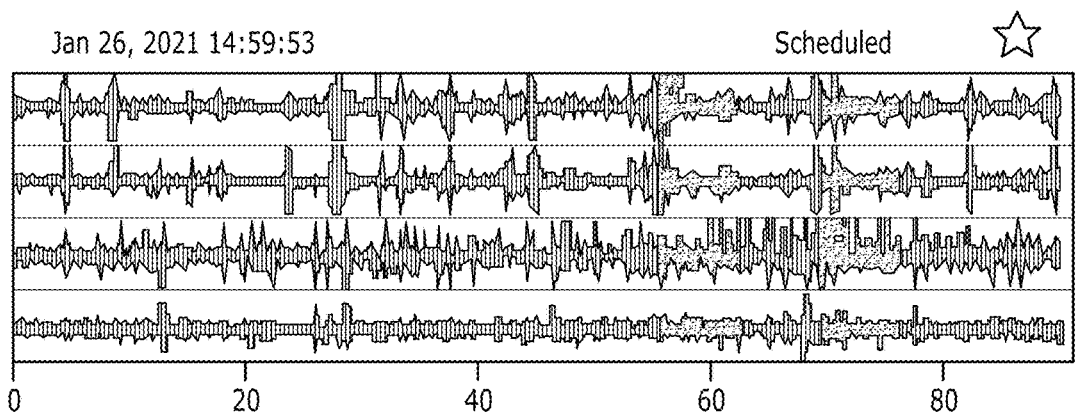
Figure 13C:
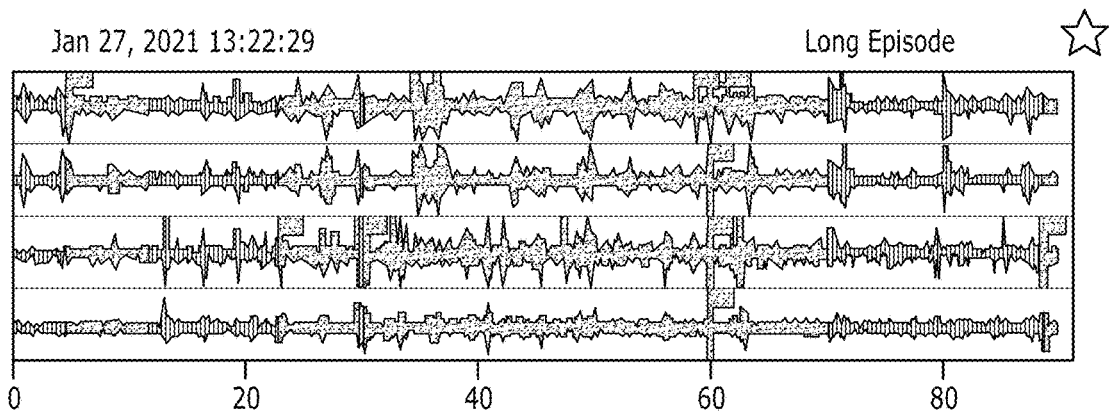
Figure 13D:
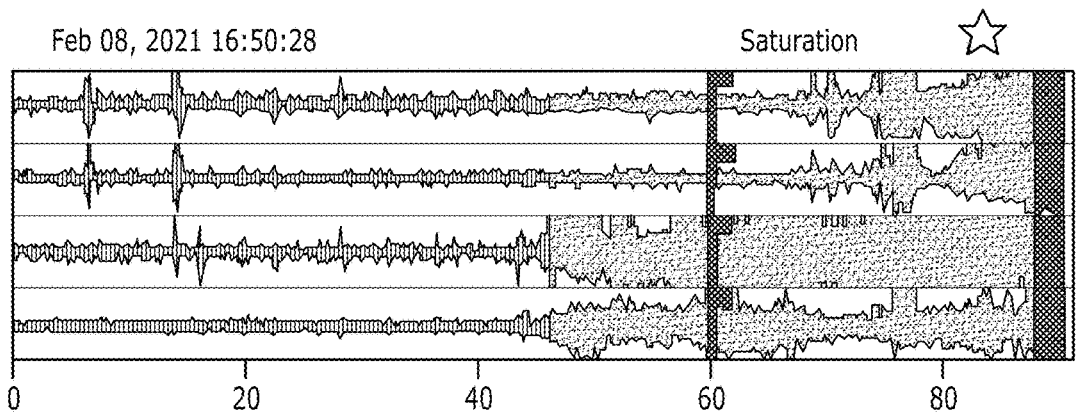
Figure 13E:
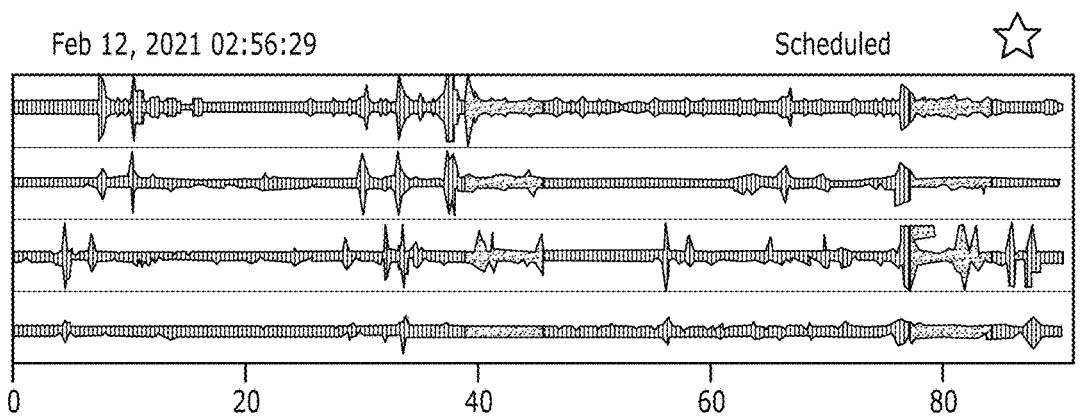
Figure 13F:
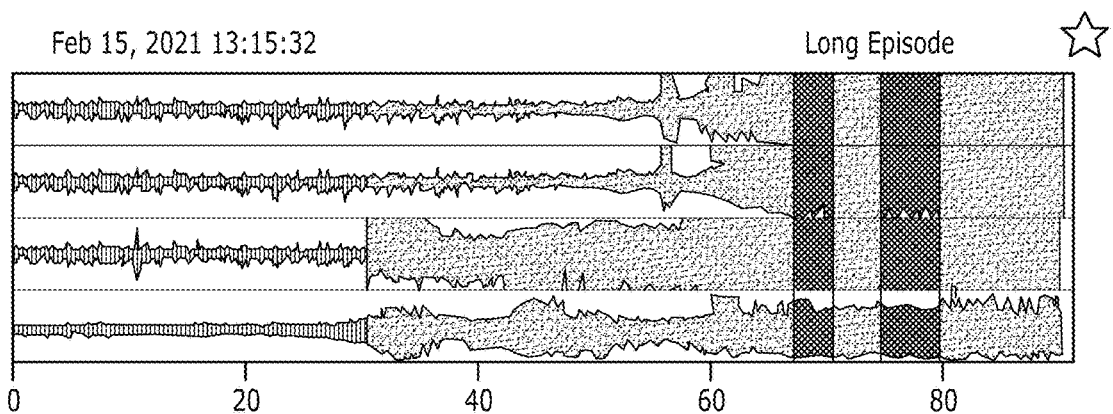
Figure 13G:
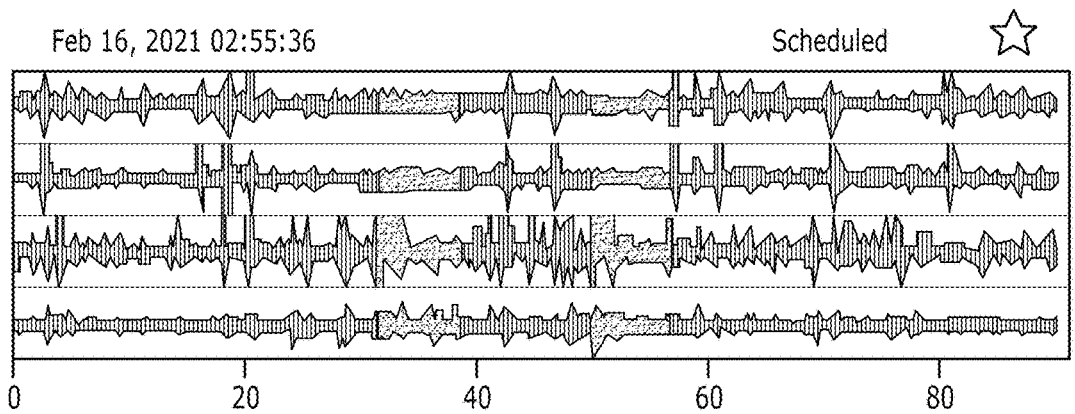
Figure 13H:
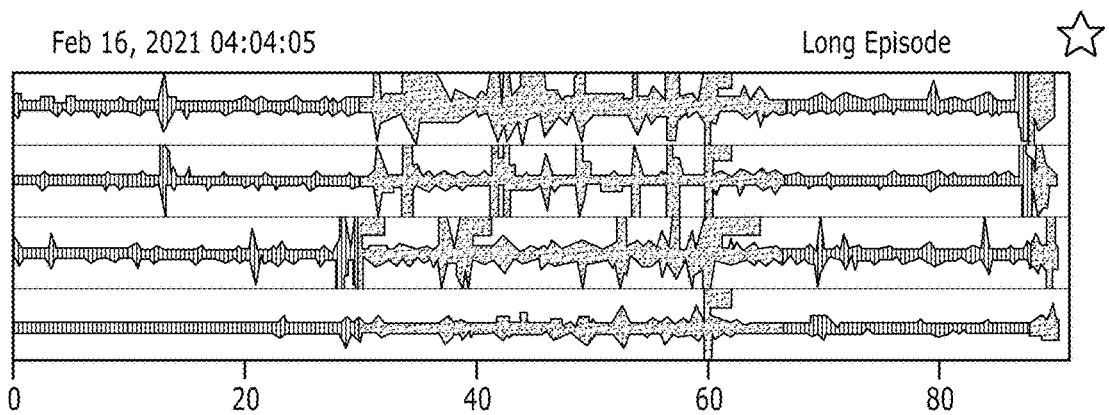
Figure 13I:
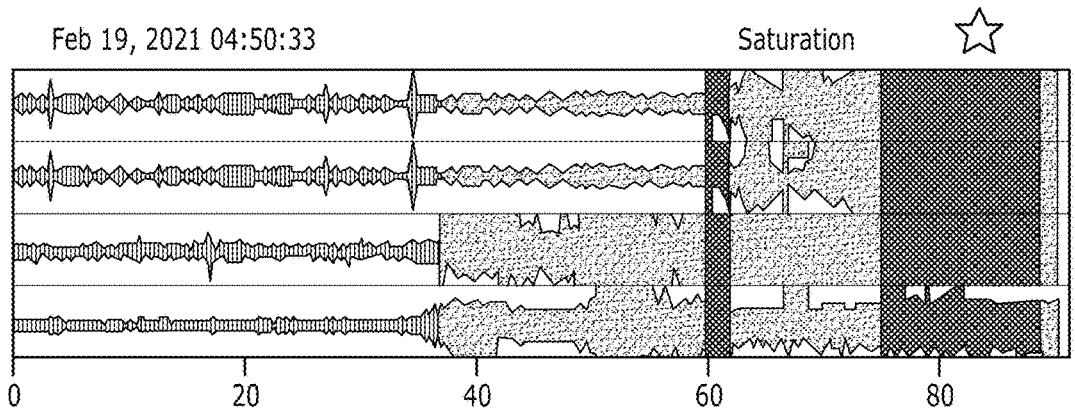

At block 1106, and with reference to FIG. 12, if the CRE biomarker 330 does not satisfy the criterion, the process proceeds to block 1108, where a parameter of the operation of the implanted neurostimulation system is adjusted or the operation of the implanted neurostimulation system is triggered. The operation may relate to electrographic event detection (e.g., how the apparatus 1200 is programmed to detect electrographic events), in which case the parameter that is adjusted is a detection parameter. In this case, a device operation module 1218 of the apparatus 1200 sends a control signal to the detection subsystem 1220 to change a detection parameter. Examples of detection parameters are described in U.S. Pat. No. 9,955,921, which is herein incorporated by reference.

The operation may relate to stimulation delivery (e.g., the stimulation that the apparatus 1200 is programmed to deliver), in which case the parameter that is adjusted is a stimulation parameter, e.g., pulse amplitude, pulse width, pulse waveform, etc. In this case, the device operation module 1218 of the apparatus 1200 sends a control signal to the therapy subsystem 1222 to change a stimulation parameter.

The adjustment made to a stimulation parameter may be based on the value of the CRE biomarker. For example, considering charge density (as determined for example by stimulation pulse amplitude and/or width), if the CRE biomarker value is 0.1, then stimulation parameters may be set so a charge density of 0.1 microcoulomb ($\mu C$) is delivered. If the value of the CRE biomarker is 0.7, then stimulation parameters may be set so a charge density of 1.4 microcoulomb ($\mu C$) is delivered. The relationship between charge density and CRE biomarker value may be based on the output of a linear regression model. In some embodiments, the value of the stimulation delivered is continuously adjusted based on the value of the CRE biomarker.

In some embodiments, at block 1108 instead of (or in addition to) adjusting a parameter of an operation (e.g., detection or stimulation) of the implanted neurostimulation system, an operation of the system may be initiated. The operation to be initiated may be stimulation delivery. For example, if the CRE biomarker determined in block 1102 exceeds a preferred value by a threshold amount (e.g., 50%), the implanted neurostimulation system may respond by delivering stimulation in accordance with current stimulation parameters. In this case, the device operation module 1218 of the apparatus 1200 sends a control signal to the therapy subsystem 1222 to that initiates stimulation delivery.

After the parameter is adjusted or operation is triggered in block 1108, the process returns to block 1102 for further execution of the method.

Returning to block 1106, if the CRE biomarker 330 does satisfy the criterion, the process returns to block 1102 without any parameter adjustment. In either case, the determining, comparing, and adjusting (if any) may be continuously or periodically performed by the implanted neurostimulation system, or may be performed in response to an occurrence of an event of interest. The event of interest may be one of a replacement of a component (e.g., battery) of the IMD, a change in operation of the IMD (e.g., lead revision, detection and/or stimulation programming changes), a change in therapy for the patient (new anti-seizure medication or change in dose), or a change in patient habits (change to diet, sleep, exercise).

FIG. 12 is a schematic block diagram of an apparatus 1200 corresponding to an implantable neurostimulation system 202 having an online or built-in clinical response estimator 204. The apparatus 1200 is configured to execute instructions related to the processes described above with reference to FIGS. 3-6 and 11. The apparatus 1200 may be embodied in any number of processor-driven devices, including, but not limited to, a server computer, a personal computer, one or more networked computing devices, an application-specific circuit, a minicomputer, a microcontroller, and/or any other processor-based device and/or combination of devices.

The apparatus 1200 may include one or more processing units 1202 configured to access and execute computer-executable instructions stored in at least one memory 1204. The processing unit 1202 may be implemented as appropriate in hardware, software, firmware, or combinations thereof. Software or firmware implementations of the processing unit 1202 may include computer-executable or machine-executable instructions written in any suitable programming language to perform the various functions described herein. The processing unit 1202 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The apparatus 1200 may also include a chipset (not shown) for controlling communications between the processing unit 1202 and one or more of the other components of the apparatus 1200. The processing unit 1202 may also include one or more application-specific integrated circuits (ASICs) or application-specific standard products (ASSPs) for handling specific data processing functions or tasks.

The memory 1204 may include, but is not limited to, random access memory (RAM), flash RAM, magnetic media storage, optical media storage, and so forth. The memory 1204 may include volatile memory configured to store information when supplied with power and/or non-volatile memory configured to store information even when not supplied with power. The memory 1204 may store various program modules, application programs, and so forth that may include computer-executable instructions that upon execution by the processing unit 1202 may cause various operations to be performed. The memory 1204 may further store a variety of data manipulated and/or generated during execution of computer-executable instructions by the processing unit 1202.

The apparatus 1200 may further include one or more interfaces 1206 that may facilitate communication between the apparatus and one or more other apparatuses. For example, the interface 1206 may be configured to transmit or send patient-specific datasets or CRE biomarkers to an external apparatus. Communication may be implemented using any suitable communications standard. For example, a LAN interface may implement protocols and/or algorithms that comply with various communication standards of the Institute of Electrical and Electronics Engineers (IEEE), such as IEEE 802.11.

The memory 1204 may store various program modules, application programs, and so forth that may include computer-executable instructions that upon execution by the processing unit 1202 may cause various operations to be performed. For example, the memory 1204 may include an operating system module (O/S) 1208 that may be configured to manage hardware resources such as the interface 1206 and provide various services to applications executing on the apparatus 1200. The memory 1204 may also store a patient-specific dataset 1210 that includes various data types and patient features, such as listed earlier in this disclosure in Tables 1 and 2.

The memory 1204 stores additional program modules such as a data/feature selection module 1212, and data/feature processing module 1214, a CRE module 1216, and a device operation module 1218. These modules 1212, 1214, 1216, 1218 includes computer-executable instructions that when executed by the processing unit 1202 cause various operations to be performed, such as the operations described immediately above and earlier with reference to FIGS. 3-6 and 11. For example, the data/feature selection module 1212 is configured to derive an input dataset from a subject-patient dataset comprising a plurality of data types that are based on electrical activity of the patient's brain sensed and stored by the implanted neurostimulation system, and at least one feature of the patient, wherein the input dataset is derived based on a plurality of key inputs of the subject-patient dataset. The data/feature processing module 1214 is configured to process the input dataset to obtain a plurality of model inputs. The CRE module 1216 is configured to apply a machine-learned clinical response estimator model to the plurality of model inputs to determine the CRE biomarker, wherein the machine-learned clinical response estimator is trained on datasets across a patient population. The device operation module 1218 is configured to compare a CRE biomarker to a criterion and adjust operation parameters of the apparatus 1200 or trigger an operation of the apparatus accordingly in response to the criterion not being met or satisfied.

The apparatus 1200 also includes a detection subsystem 1220 and a therapy subsystem 1222. These subsystems correspond respectively to the detection subsystem and a therapy subsystem in FIG. 21, described later in this disclosure. Briefly, however, the detection subsystem 1220 is configured to detect electrographic events through signals sensed by electrodes (see FIG. 21) in accordance with detection parameters, while the therapy subsystem 1222 is configured to delivery stimulation through electrodes in accordance with stimulation parameters.

The apparatus 1200 and modules disclosed herein may be implemented in hardware or software that is executed on a hardware platform. The hardware or hardware platform may be a general-purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Example of Data Type Combining by Clinical Response Estimator.

As described above with reference to FIG. 3, the data/feature processing module 304 of a clinical response estimator 204 may execute different types of data processing including a combining of two or more components of the input dataset to provide a model input to the CRE model. One example type of combining of the data/feature processing module 304 processes two data types—EEG records and episode duration—to provide a model input corresponding to a duration threshold.

Prior to describing this combining process of the data/feature processing module 304 of the clinical response estimator 204 further, some background description of the operation of an implanted neurostimulation system as it relates to the two data types—EEG records and episode duration—is provided. The implanted neurostimulation system 202 can be programmed to detect patterns in electrical activity of the brain that may represent abnormal activity. After initial detection of such a pattern, re-evaluation occurs on a frequent basis. For example, re-evaluation may occur every 128 msec. If an abnormal pattern is redetected, an episode of abnormal activity is considered to be detected. Once the abnormal pattern is no longer detected the episode is over. The implanted neurostimulation system 202 stores a report for the episode that includes the duration of the episode. Depending on the amount of available memory, the implanted neurostimulation system 202 may also store a raw EEG record of the electrical activity if the duration is above a threshold. For example, the implanted neurostimulation system 202 may be programmed to store EEG records for episode durations greater than 10 seconds.

Examples of EEG records from an implanted neurostimulation system 202 are shown in FIGS. 13A-13I in the form of time-series waveforms or tracings. Periods within the tracings corresponding to "no detection" and ongoing "episode detection" are indicated in accordance with the shown legend. Episode durations vary in these samples from several seconds to over one minute with activity ongoing at the end of the tracing.

Figure 14A:
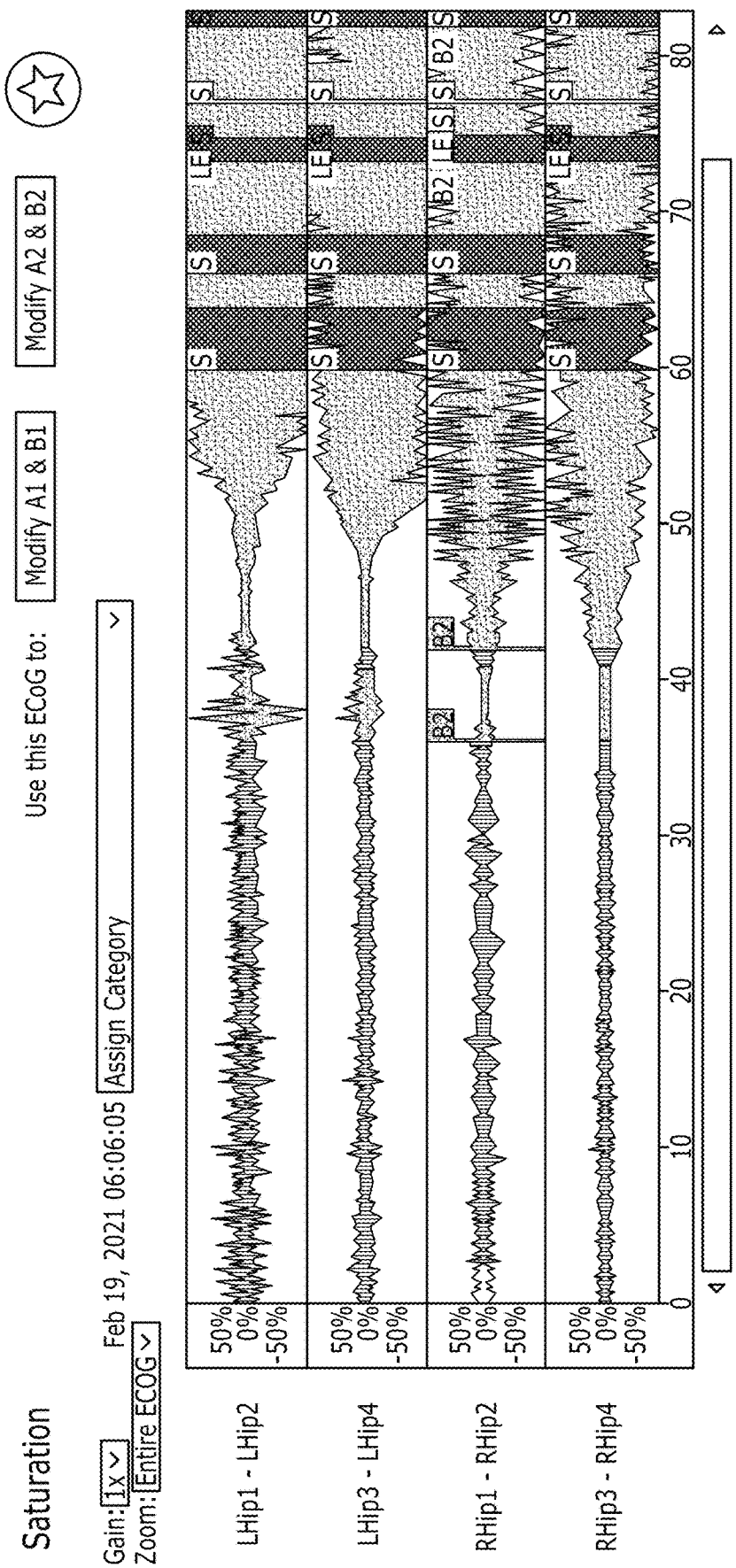
FIG. 14A is a schematic illustration of a time-series waveform representation of an EEG record.

With reference to FIGS. 14A and 14B, an example of an episode duration correlated with a time-series representation of an EEG record is shown. The EEG record in FIG. 14A results from saturation of sensing electronics of the implanted neurostimulation system 202. In FIG. 14B, data and information of the episode corresponding to the EEG record of FIG. 14A is shown as episode #357 in a table of information. Episodes #353-356 correspond to episodes detected by the implanted neurostimulation system 202 before the detection of episode #357. Episodes #358-361 correspond to episodes detected by the implanted neurostimulation system 202 after the detection of episode #357. Due to the short duration of episodes #353-356 and episodes

358-361, the implanted neurostimulation system 202 did not store corresponding EEG records for these episodes.

Figure 15C:
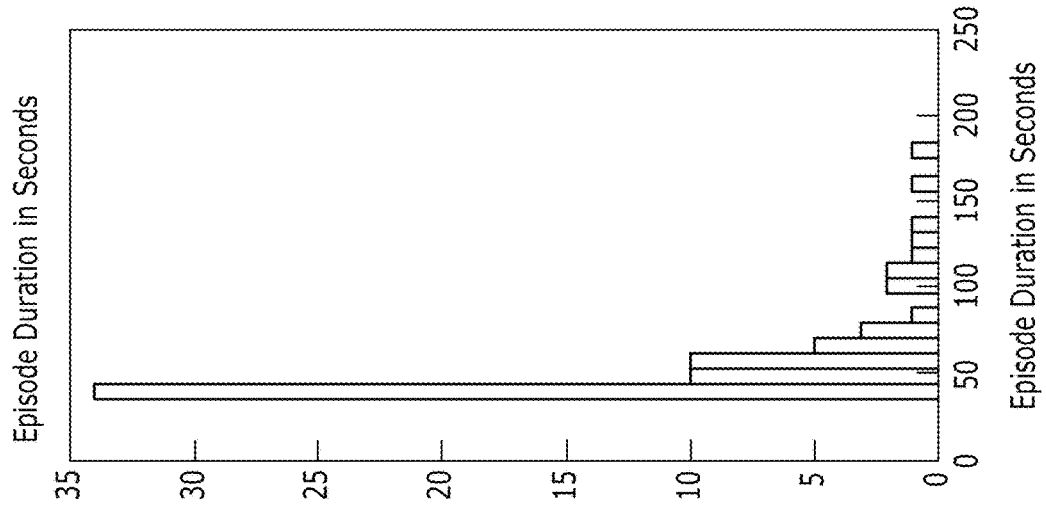
FIGS. 15A-15C are example ways of representing episode durations.
Figure 15B:
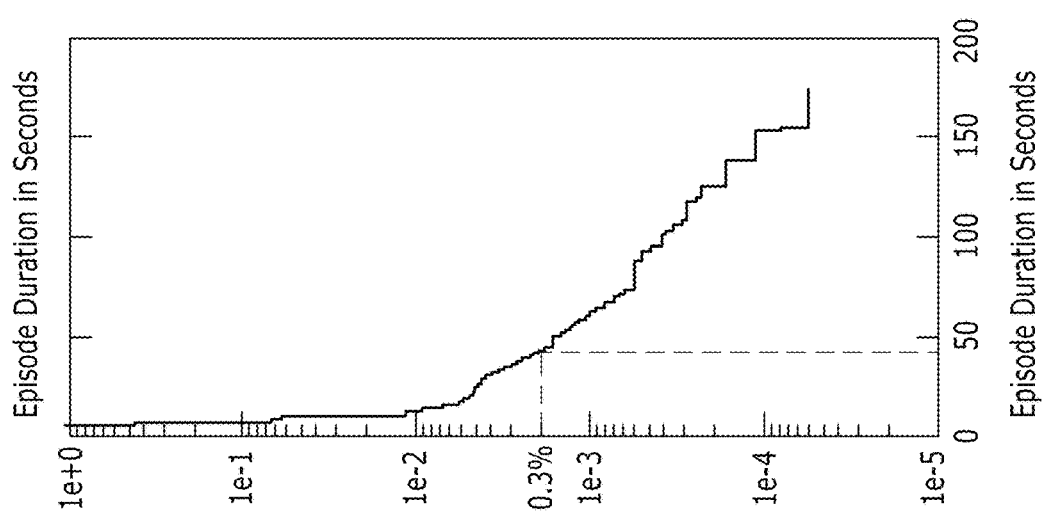
Figure 15A:
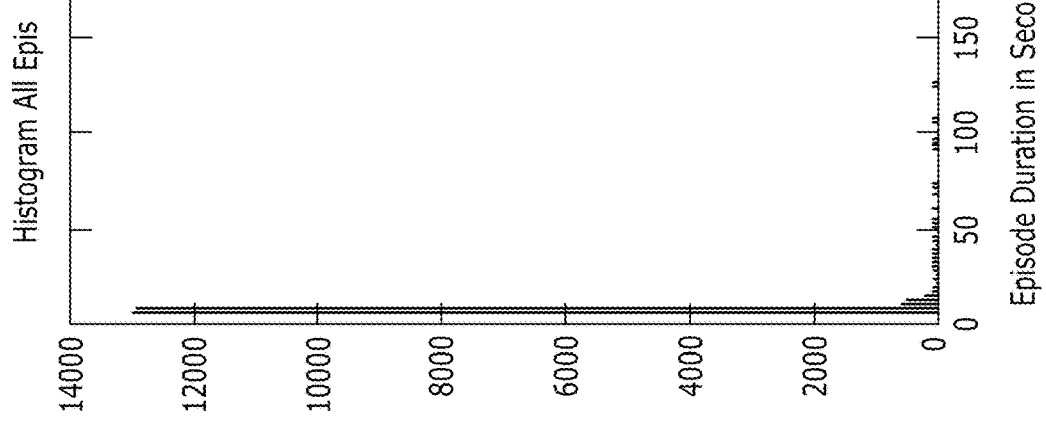

With reference to FIGS. 15A-15C, which present episode durations for 112 days of EEG data in different way, most episodes detected by an implanted neurostimulation system 202 are brief in duration. In FIG. 15A, the episode durations are shown in linear-linear histogram. Most of the occurrences are brief and stacked on the left side of this histogram. These same data are displayed in FIG. 15B as a normalized log-linear survival plot which reveals that only 0.3% of episodes are 40 seconds or longer in duration. FIG. 15C plots only those episodes that exceed 30 seconds. These longer events are in general more likely to be of clinical significance and are typically the events that have stored EEG records.

Now, considering a combining function of the data/feature processing module 304 as described above, raw EEG records and their respective episode durations are included in the input dataset. A machine-learned model of the data/feature processing module 304 is applied to the raw EEG records to provide a seizure probability. To this end, deep learning models of the clinical response estimator 204 may be applied. Example deep learning models for use are disclosed in Barry et al., A High Accuracy Electrographic Seizure Classifier Trained Using Semi-Supervised Labeling Applied to a Large Spectrogram Dataset, Frontiers in Neuroscience, Vol. 15, pgs. 1-20, Jun. 28, 2021. FIG. 16 shows various EEG records of long episodes and a corresponding seizure probability for each, as determined by the machine-learned model of the data/feature processing module 304.

Figure 17:
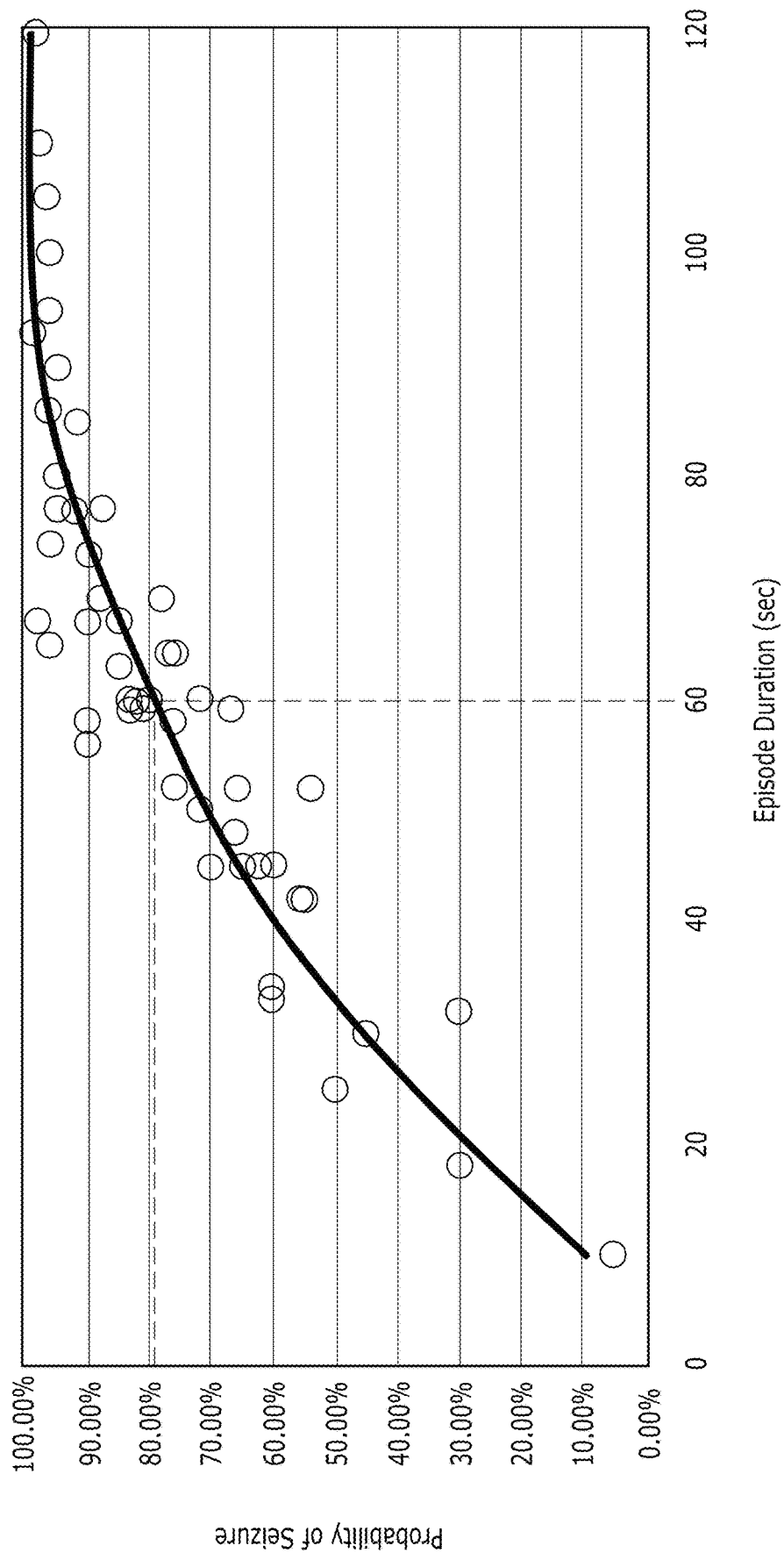
FIG. 17 is a graph illustrating a relationship between seizure probability and episode duration.

The data/feature processing module 304 then creates a mapping between seizure probability and episode duration. With reference to FIG. 17, the mapping may be represented as a plot of episode duration verses seizure probability (as output by the machine-learned model). Providing the seizure probability function converges to a high probability (e.g., >90%) with longer episode durations, the data/feature processing module 304 determines a duration threshold that sets an episode duration that once exceeded has the threshold probability of being ictal in nature. For example, in FIG. 17 an episode duration of 60 seconds corresponds to the probability threshold of 80%, so once the episode duration exceeds 60 seconds the probability of the event being ictal in nature should be at least 80%.

Electrographic Seizure Detection Based on Episode Duration

Figure 18:
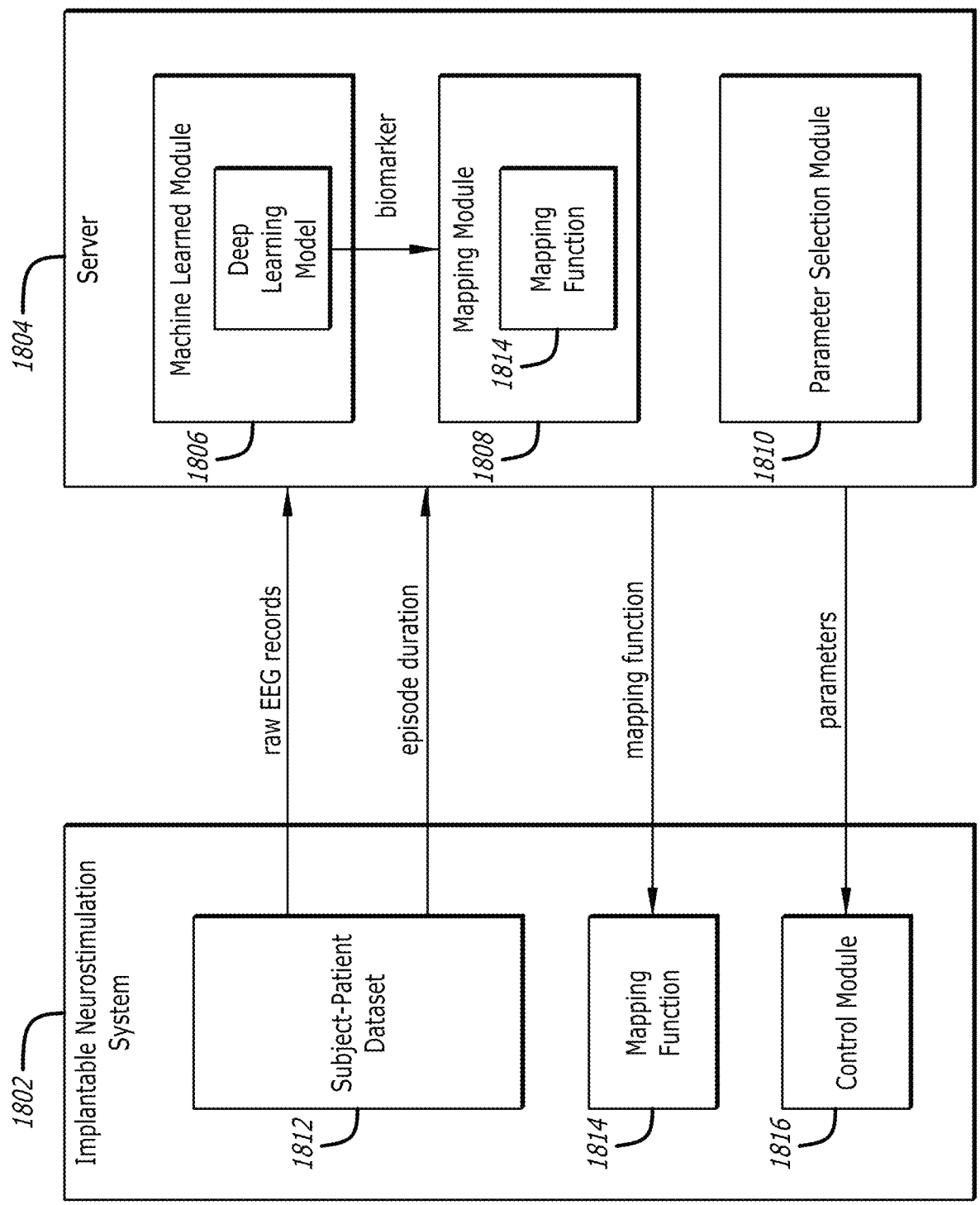
FIG. 18 is a block diagram illustrating a process flow between an implantable neurostimulation system and an external server for developing a mapping function for controlling operations of the implantable neurostimulation system.

FIG. 18 is a block diagram of a process flow between an implantable neurostimulation system 1802 and an external server 1804 for developing a mapping function for controlling operations of the implantable neurostimulation system. The external server 1804 includes a machine-learned module 1806, a mapping module 1808, and a parameter selection module 1810. The implantable neurostimulation system 1802 includes a subject-patient dataset 1812. The implantable neurostimulation system 1802 may also include a mapping function 1814 and a control module 1816. The implantable neurostimulation system 1802 includes other components (e.g., a detection subsystem, therapy subsystem) described below with reference to FIG. 21.

For a given patient, different types of data from a subject-patient dataset 1812 are selected for processing. These data may be retrieved from the implanted neurostimulation system 1802 through periodic telemetry sessions using a patient appliance and transferred for off-line analysis and processing by the server 1804. In the example of FIG. 18, only two data types are selected—raw EEG records and episode duration. In other embodiments, additional data types may be selected.

The machine-learned module 1806 is applied to the raw EEG records to provide a biomarker in the form of electrographic seizure probability, referred to going forward as "seizure probability." In one embodiment, the machine-learned module 1806 applies deep learning models as disclosed in Barry et al., A High Accuracy Electrographic Seizure Classifier Trained Using Semi-Supervised Labeling Applied to a Large Spectrogram Dataset, Frontiers in Neuroscience, Vol. 15, pgs. 1-20, Jun. 28, 2021.

The mapping module 1808 receives the seizure probability biomarkers from the machine-learned module 1806 and the episode durations, and generates a mapping function 1814 that maps each seizure probability biomarker with its corresponding episode duration. To this end, each raw EEG record and episode duration may be identified by an episode number. The episode number of a raw EEG record is linked to the seizure probability biomarker of that EEG record. Thus, seizure probability biomarkers and episode durations are linked by episode numbers.

Referring back to FIG. 17, the mapping function 1814 between seizure probability and episode duration may be represented as a plot of episode duration verses seizure probability biomarker. The mapping function 1814 may be used by the parameter selection module 1810 to automatically determine one or more operation parameters of the implantable neurostimulation system 1802, such as:

1) Electrographic seizure detection parameter. The electrographic seizure detection parameter corresponds to an episode duration that once exceeded has the threshold probability of being ictal in nature. For example, in the mapping function of FIG. 17 an episode duration of 60 seconds corresponds to the probability threshold of 80%, so once the episode duration exceeds 60 seconds the probability of the event being ictal in nature should be at least 80%. The foregoing electrographic seizure detection parameter based on duration may function as a surrogate for more complex, processing-intensive seizure detection normally performed by analysis tools of the implantable neurostimulation system. These analysis tools are described further below and may include one or more of a half-wave tool, a line length tool, and an area tool. Using the foregoing electrographic seizure detection parameter in lieu of these analysis tools may reduce power consumption by the implantable neurostimulation system and thereby increase system longevity.

2) Date/time storage parameter. The date/time storage parameter corresponds to an episode duration that once exceeded triggers the implantable neurostimulation system to store the date/time and duration of the episode. Storing the date/time and episode duration as such eliminates the need for the implantable neurostimulation system to create a corresponding EEG record of the episode. This reduces system processing and memory usage. The amount of memory required to store a date/time stamp accurate to fractions of a second is 13 bytes. Alternatively, a real-time clock value could be stored to mark an event time that has similar memory requirements. This compares favorably to the 720 Kbytes required for a 90-second EEG record (4 channels, 8-bit amplitude resolution, 250 Hz sampling), and allows the implantable neurostimulation system to store data that covers months or possibly years of time without risk of overwrite.

3) EEG record storage parameter. The EEG record storage parameter corresponds to an episode duration that once exceeded triggers the implantable neurostimulation system to create an EEG record of the episode. This parameter may be used in conjunction with the date/time storage parameter to optimize the diagnostic settings in the system. For example, the episode duration (the EEG record storage parameter) that triggers creation of an EEG record could be set to only store EEGs that have a higher probability of being an ictal event, while the episode duration (the date/time storage parameter) is set to only store date/time of episodes that have a lower probability of being an ictal event.

4) Therapy delivery parameter. The therapy delivery parameter corresponds to an episode duration that once exceeded triggers the implantable neurostimulation system to deliver therapy.

5) Warning parameter. The warning parameter corresponds to an episode duration that once exceeded triggers the implantable neurostimulation system to output a warning. To this end, the implantable neurostimulation system may output a real-time warning, for example, through a blue tooth connection to a wireless device, in response to an episode duration that exceeds the warning parameter. In the event the warning is considered too sensitive, or not sensitive enough, the warning parameter could be adjusted to provide a better balance of sensitivity and specificity via a patient appliance in conjunction with the server. For example, the warning parameter may be set to a duration on the mapping function of FIG. 17 that has a higher probability of seizure.

The parameter selection module 1810 may automatically determine one or more of the foregoing operation parameters. The plurality of foregoing parameters could be triggered by the same episode duration corresponding to the same ictal probability (i.e., the same seizure probability biomarker), or these parameters could be set to set to different episode durations corresponding to different ictal probabilities (or different seizure probability biomarkers) as determined to be clinically useful. For example, sufficient EEG record storage may be available to allow the EEG record storage parameter (foregoing parameter 3) to be set to allow storage of events with probabilities as low as 60%, but the warning parameter (foregoing parameter 5) may need to be more specific to avoid most false positives and hence set to a higher level such as 95%.

With reference to FIG. 17, given the example mapping function of a specific patient, the parameter selection module 1810 may be programmed to set different duration parameters based on specified seizure probabilities as follows: For a specified seizure probability of 80%, the electrographic seizure threshold (foregoing parameter 1) is automatically set to 60 seconds. For a specified seizure probability of 30%, the date/time storage threshold (foregoing parameter 2) is automatically set to 30 seconds. This lower threshold is used, not to count seizures, but to quantify episodes exceeding a threshold duration and inform a clinical response estimation. This would be especially usefully if seizures are rare, and episodes longer than 30 seconds are more frequent. The threshold for the EEG record storage threshold (foregoing parameter 3) may be configured similarly to the date/time storage parameter so they are both describing the same phenomenon, one capturing a continuous record of counts, and the other capturing only the most recent EEG records. For a specified seizure probability of 60%, the therapy delivery threshold (foregoing parameter 4) is automatically set to 45 second. This may be done to deliver a specific therapy when an episode exceeds a specific duration such as 45 seconds because it may be desired to deliver that therapy after 45 seconds into an electrographic seizure. Finally, for a specified seizure probability of 100%, the warning threshold (foregoing parameter 4) may be triggered by an episode duration threshold of 2 minutes, for example, so that the user is informed of especially severe episodes that are long in duration. A long threshold would be used in this case so that the patient is not warned too frequently, or because the physician is being alerted.

The server 1804 may provide the operation parameters to a control module 1816 of the implantable neurostimulation system 1802. The control module 1816 (which may correspond to the central processing unit 2140 in FIG. 21) is configured to program appropriate elements (e.g., the detection subsystem 2126 and therapy subsystem 2128) of the implantable neurostimulation system 1802 based on the operation parameters.

The server 1804 may provide the mapping function 1814 to the implantable neurostimulation system 1802. In that case, the mapping function 1814 may be available independent of the server 1804. For example, a physician may access the mapping function 1814 through a programmer 216 (shown in FIG. 2) and view it for purposes of modifying one or more of the operation parameters.

Figure 19A:
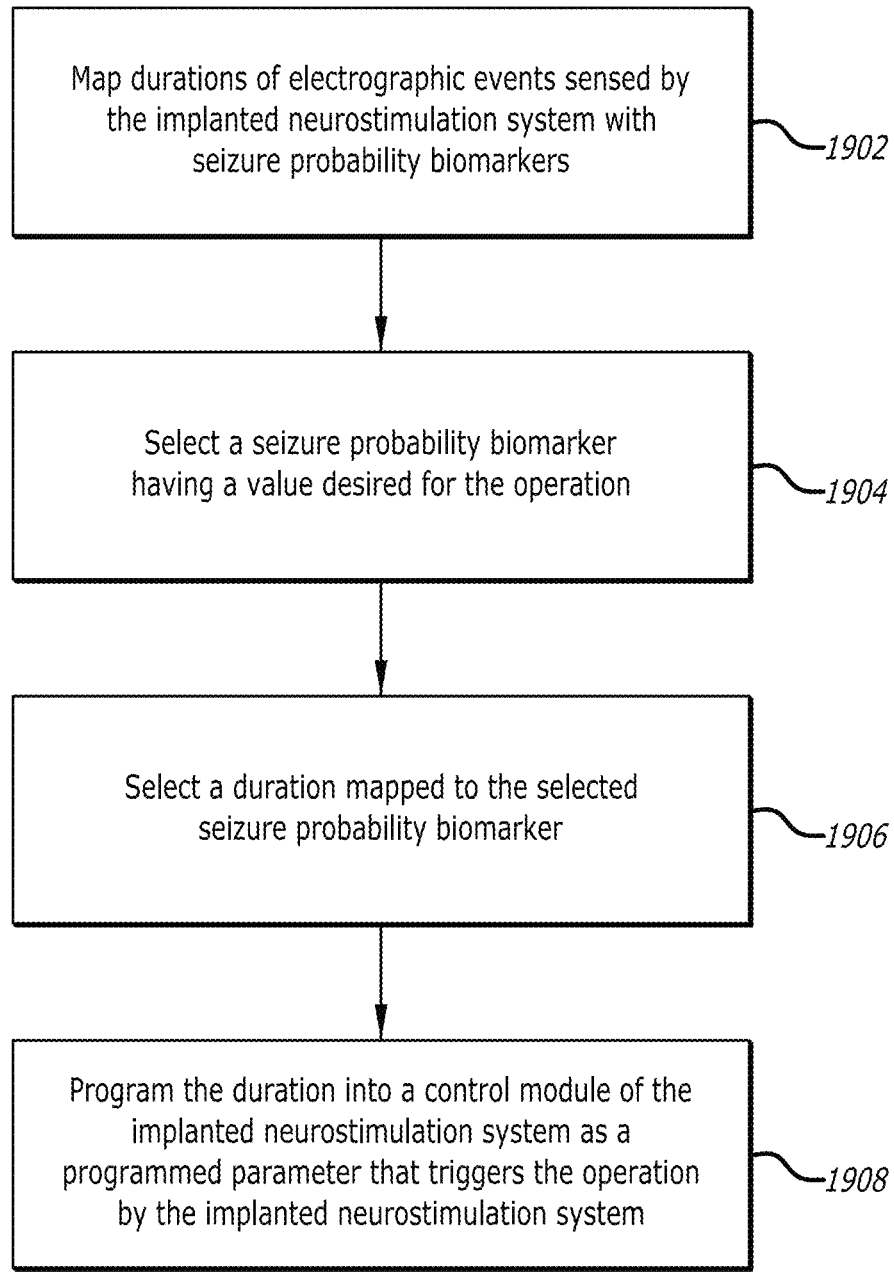
FIG. 19A is a flowchart of a method controlling operation of an implanted neurostimulation system configured to detect episodes of electrographic events and determine corresponding durations.

FIG. 19A is a flowchart of a method of controlling operation of an implanted neurostimulation system 1802 configured to sense episodes of electrographic events and determine durations of episodes. The method may be performed by the server 1804 of FIG. 18.

At block 1902, durations of electrographic events sensed by the implanted neurostimulation system 1802 of a particular patient are mapped with seizure probability biomarkers. The seizure probability biomarkers are derived from records of electrographic events (e.g., raw EEG records) sensed by the implanted neurostimulation system 1802. For example, a machine-learned model included in the machine-leaned module 1806 may be applied to each of the records of the electrographic events to derive a seizure probability biomarker for each record. The machine-learned model may be a deep learning model and the records of electrographic events may correspond to ictal events.

Next, for each of one or more operations of the implanted neurostimulation system 1802: At block 1904, a seizure probability biomarker having a value desired for the operation is selected. The seizure probability biomarker may be, as shown in FIG. 17, a percentage probability between zero and 100 of seizure. At block 1906, a duration mapped to the selected seizure probability biomarker is determined. The duration may be, as shown in FIG. 17, a duration of an electrographic episode. At block 1908, the duration is programmed into a control module 1816 of the implanted neurostimulation system 1802 as a programmed parameter that triggers or initiates the operation by the implanted neurostimulation system. In some embodiments, the duration is the sole (i.e., the only) parameter that triggers the operation.

The operation of the implanted neurostimulation system 1802 may be a detection of an ictal electrographic event. In this case, the programming by the server 1804 causes the implanted neurostimulation system 1802 to detect an event when the system senses an electrographic episode having a duration that exceeds the programmed parameter. The event may be detected by a detection subsystem of the implanted neurostimulation system 1802, such as the detection subsystem 2126 shown in FIG. 21.

The operation of the implanted neurostimulation system 1802 may be a storing of a date/time of a sensed episode. In this case, the programming by the server 1804 causes the implanted neurostimulation system 1802 to store the date/time when the system senses an electrographic episode having a duration that exceeds the programmed parameter. The episode may be sensed by the detection subsystem of the implanted neurostimulation system 1802, such as the detection subsystem 2126 shown in FIG. 21, and the date/time stored in a memory subsystem 2138.

The operation of the implanted neurostimulation system 1802 may be a storing of record of a sensed episode. In this case, the programming by the server 1804 causes the implanted neurostimulation system 1802 to create an EEG record of the sensed episode when the system senses an electrographic episode having a duration that exceeds the programmed parameter. The episode may be sensed by, and the EEG record created by the detection subsystem of the implanted neurostimulation system 1802, such as the detection subsystem 2126 shown in FIG. 21, and the EEG record may be stored in the memory subsystem 2138.

The operation of the implanted neurostimulation system 1802 may be a delivery of stimulation therapy. In this case, the programming by the server 1804 causes the implanted neurostimulation system 1802 to deliver stimulation when the system senses an episode having a duration that exceeds the programmed parameter. The stimulation may be delivered by a therapy subsystem of the implanted neurostimulation system 1802, such as the therapy subsystem 2128 shown in FIG. 21.

The operation of the implanted neurostimulation system 1802 may be an output of a warning. In this case, the programming by the server 1804 causes the implanted neurostimulation system 1802 to output a warning when the system senses an episode having a duration that exceeds the programmed parameter. The warning may be output by a communication subsystem of the implanted neurostimulation system 1802, such as the communication subsystem 2142 shown in FIG. 21.

Figure 19B:
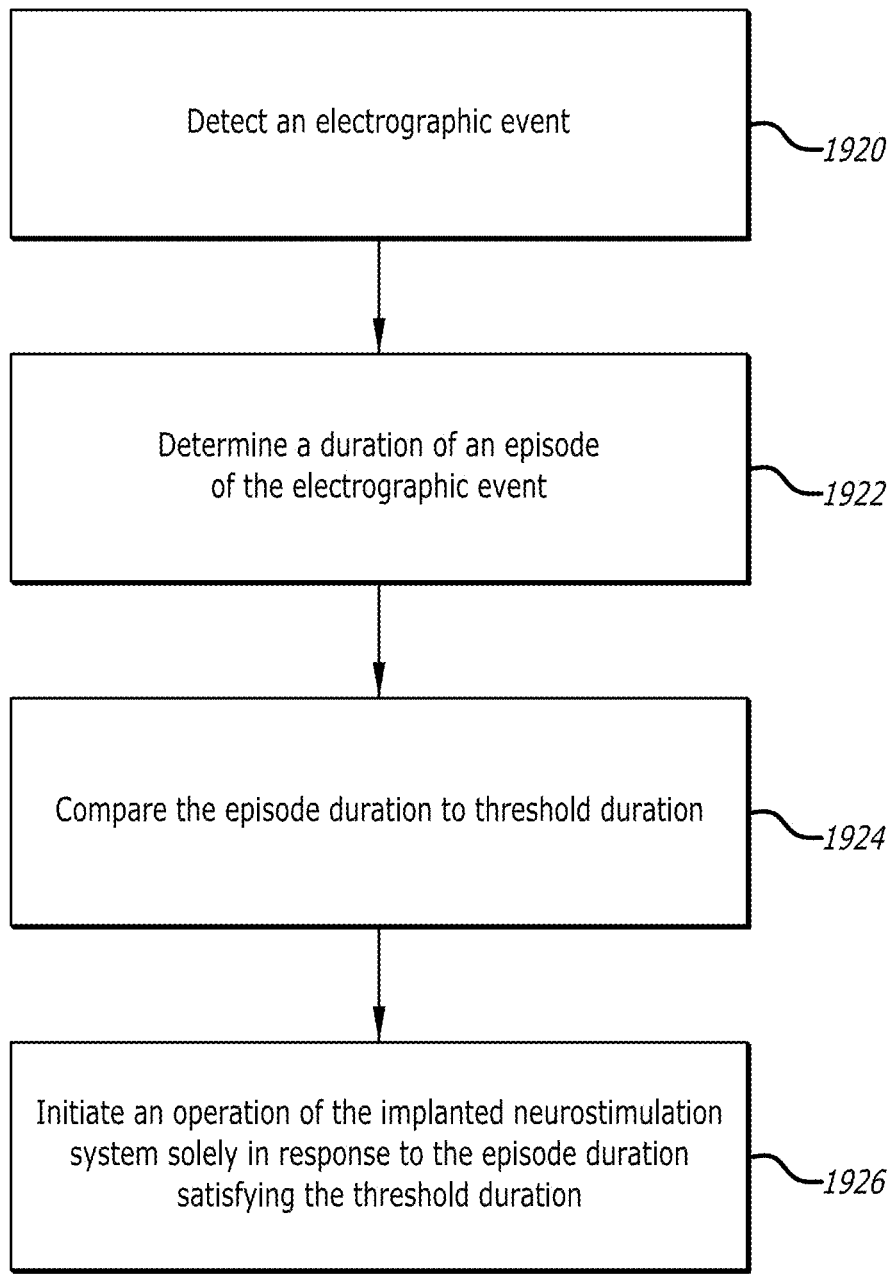
FIG. 19B is a flowchart of a method of operation of an implanted neurostimulation system.

FIG. 19B is a flowchart of a method of operation of an implanted neurostimulation system. The method may be performed by the implantable neurostimulation system of FIGS. 18, 20 and 21.

At block 1920, an electrographic event is detected by the implantable neurostimulation system 1802. At block 1922, a duration of an episode of the electrographic event is determined. To these ends, the implanted neurostimulation system 1802 can be programmed to detect patterns in electrical activity of the brain that may represent abnormal activity. After initial detection of such a pattern, re-evaluation occurs on a frequent basis. For example, re-evaluation may occur every 128 msec. If an abnormal pattern is redetected, an episode of abnormal activity is considered to be detected. Once the abnormal pattern is no longer detected the episode is over. The implanted neurostimulation system 1802 stores a report for the episode that includes the duration of the episode.

At block 1924, the episode duration is compared to a threshold duration.

At block 1926, an operation of the implanted neurostimulation system 1802 is initiated solely in response to the episode duration satisfying the threshold duration. The threshold duration corresponds to one of a plurality of threshold durations, each threshold duration associated with a different seizure probability biomarker.

The operation of the implanted neurostimulation system 1802 may be a detection of an ictal electrographic event. In this case, the implanted neurostimulation system 1802 detects an ictal event in response to the detected episode having an episode duration that exceeds the threshold duration. The ictal event may be detected by a detection subsystem of the implanted neurostimulation system 1802, such as the detection subsystem 2126 shown in FIG. 21.

The operation of the implanted neurostimulation system may be a storing of a date/time of the episode of the electrographic event. In this case, the implanted neurostimulation system 1802 stores the date/time of the detected episode in response to the detected episode having an episode duration that exceeds the threshold duration. The episode may be sensed by the detection subsystem of the implanted neurostimulation system 1802, such as the detection subsystem 2126 shown in FIG. 21, and stored in a memory subsystem 2138.

The operation of the implanted neurostimulation system 1802 may be a storing of record of the episode of the electrographic event. In this case, the implanted neurostimulation system 1802 creates an EEG records of the detected episode in response to the detected episode having an episode duration that exceeds the threshold duration. The episode may be detected by, and the EEG record created by the detection subsystem of the implanted neurostimulation system 1802, such as the detection subsystem 2126 shown in FIG. 21, and the EEG record may be stored in the memory subsystem 2138.

The operation of the implanted neurostimulation system 1802 may be a delivery of stimulation therapy. In this case, the implanted neurostimulation system 1802 delivers stimulation in response to the detected episode having an episode duration that exceeds the threshold. The stimulation may be delivered by a therapy subsystem of the implanted neurostimulation system 1802, such as the therapy subsystem 2128 shown in FIG. 21.

The operation of the implanted neurostimulation system 1802 may be an output of a warning. In this case, the implanted neurostimulation system 1802 outputs a warning in response to detected episode having an episode duration that exceeds the threshold duration. The warning may be output by a communication subsystem of the implanted neurostimulation system 1802, such as the communication subsystem 2142 shown in FIG. 21.

Overview of Implanted Neurostimulation System

Figure 20:
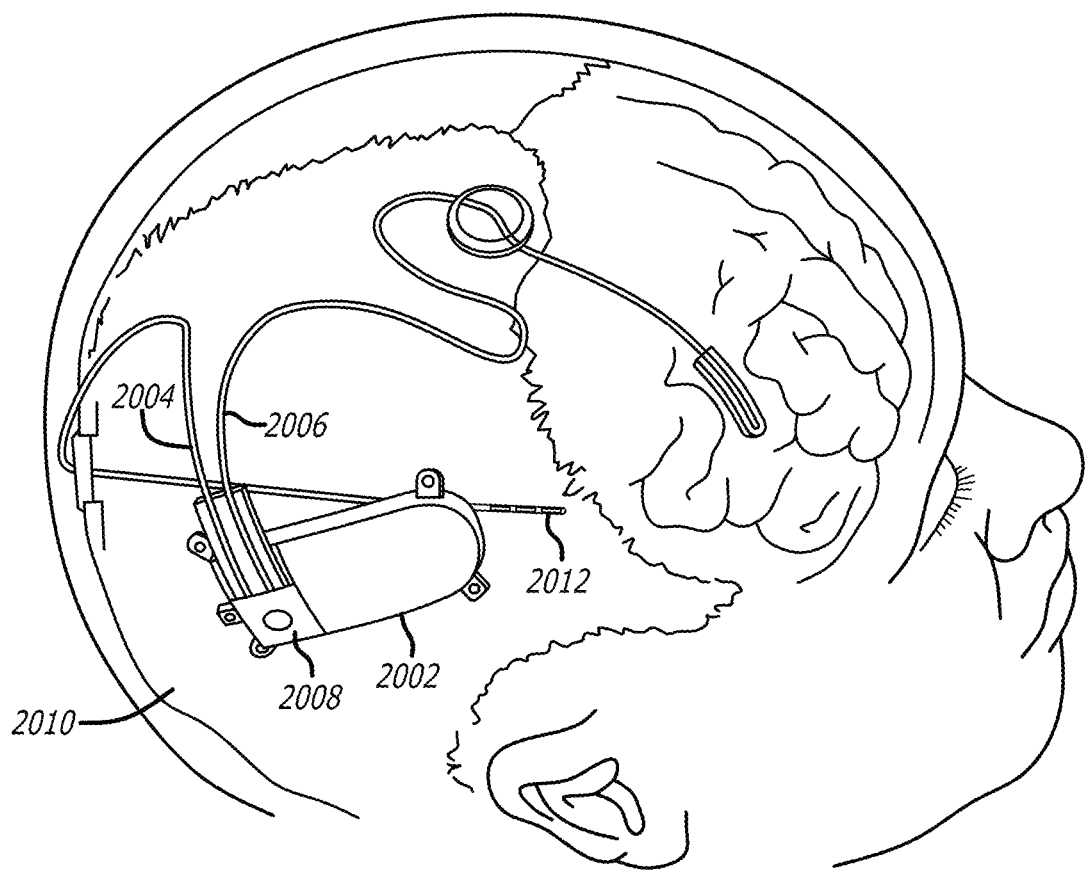
FIG. 20 is a perspective, schematic illustration of a neurostimulation system implanted in a patient and configured to sense and record EEG records and other physiological information used by the system of FIG. 2.

FIG. 20 is an illustration of the implanted neurostimulation system including a neurostimulator 2002 and two electrode-bearing brain leads 2004, 2006, implanted in a patient. The system is configured to sense and record electrical brain activity and other physiological information to be used by the training system of FIG. 3.

The neurostimulator 2002 includes a lead connector 2008 adapted to receive one or more of the brain leads, such as a deep brain or depth lead 2004 and a cortical strip lead 2006. The depth lead is implanted so that a distal end of it is situated within the patient's neural tissue, whereas the cortical strip lead is implanted under the dura mater so that a distal end of it rests on a surface of the brain. The lead connector 2008 acts to physically secure the brain leads 2004, 2006 to the neurostimulator 2002, and facilitates electrical connection to conductors in the brain leads 2004, 2006 coupling one or more electrodes at or near a distal end of the lead to circuitry within the neurostimulator 2002.

The proximal portion of the deep brain lead 2004 is generally situated on the outer surface of the cranium 2010 (and under the patient's scalp), while the distal portion of the lead enters the cranium 2010 and is coupled to at least one depth electrode 2012 implanted in a desired location in the patient's brain. The proximal portion of the cortical lead 2006 is generally situated on the outer surface of the cranium 2010 (and under the patient's scalp), while the distal portion of the lead enters the cranium 2010. The distal portion of the cortical lead 2006 includes at least one cortical electrode (not visible) implanted in a desired location on the patient's brain.

Figure 21:
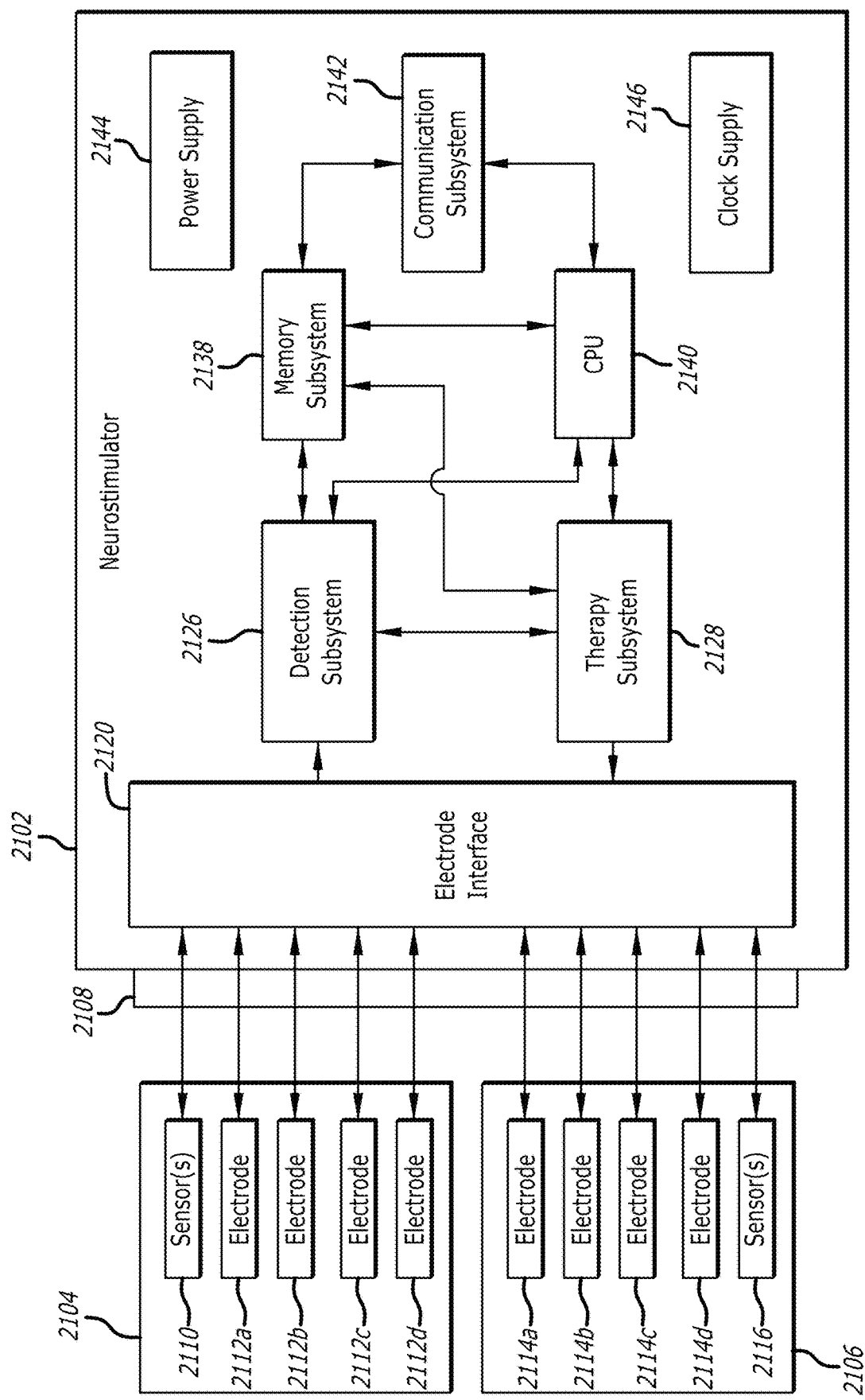
FIG. 21 is a block diagram of an implantable neurostimulation system like the one shown in FIG. 20, illustrating some of the functional subsystems of the system.

FIG. 21 is a block diagram of the implanted neurostimulation system of FIG. 20 The system may be configured to sense electrical brain activity, detect neurological events in accordance with a set of detection parameters, delivery electrical neurostimulation to the brain in accordance with a set of stimulation parameters, and store records of electrical brain activity and other physiological information for use by the training system of FIG. 3.

The neurostimulator 2102 includes a lead connector 2108 adapted to receive a connector end of each brain lead 2104, 2106, to thereby electrically couple each lead and its associated electrodes 2112a-d, 2114a-d with the neurostimulator. The neurostimulator 2102 may configure an electrode 2112a-d, 2114a-d as either a sensor (for purposes of sensing electrical activity of the brain) or a stimulator (for purposes of delivering therapy to the patient in the form of electrical stimulation) or both.

The electrodes 2112a-d, 2114a-d are connected to an electrode interface 2120. The electrode interface 2120 can select each electrode 2112a-d, 2114a-d as required for sensing and stimulation. The electrode interface 2120 may also provide any other features, capabilities, or aspects, including but not limited to amplification, isolation, and charge-balancing functions, which are required for a proper interface with neurological tissue.

The electrode interface 2120 is coupled to a detection subsystem 2126, which is configured to process electrical activity of the brain sensed through the electrode 2112a-d, 2114a-d. To this end, the detection subsystem 2126 may include a data analyzer with an EEG waveform analysis module for analyzing EEGs. The EEG waveform analysis module is adapted to receive EEG signals from the electrodes 2112a-d, 2114a-d and to process those signals to detect electrographic activity indicative of a seizure, a seizure onset, or any other electrographic activity or neurological event of interest. The implanted neurostimulation system 202 may be programmed with detection parameters (i.e., a detection parameter set) related to the operation of one or more analysis tools. These analysis tools are described further below and may include one or more of a half-wave tool, a line length tool, and an area tool. The neurostimulator 2102 may process a segment of an acquired EEG using one or more of the analysis tools to determine if the segment satisfies an event detection criterion corresponding to one of the detection parameters. If the criterion is satisfied, an event is considered to be detected. These analysis tools are described in detail, for example, in U.S. Pat. No. 6,810,285 for "Seizure Sensing and Detection Using an Implantable Device", issued Oct. 26, 2004; and U.S. Pat. No. 7,966,073 for "Differential Neurostimulation Therapy Driven by Physiological Therapy" issued Jun. 21, 2011, each of which is incorporated herein by reference in the entirety.

The electrode interface 2120 may also be coupled to a therapy subsystem 2128, which is configured to deliver therapy to the patient through the electrode 2112a-d, 2114a-d in the form of electrical stimulation. The therapy subsystem 2128 is capable of applying electrical stimulation to neurological tissue through the electrodes 2112a-d, 2114a-d. This can be accomplished in any of a number of different manners. For example, it may be advantageous in some circumstances to provide stimulation in the form of a substantially continuous stream of pulses, or on a scheduled basis. This form of stimulation, sometimes referred to as "programmed stimulation," is provided by a programmed stimulation function of the therapy subsystem 2128. Preferably, therapeutic stimulation is also provided in response to abnormal events detected by the data analysis functions of the detection subsystem 2126. This form of stimulation, namely responsive stimulation, is provided by a responsive stimulation function of the therapy subsystem 2128. The implanted neurostimulation system 202 may be programmed with stimulation parameters (i.e., a stimulation parameter set). The stimulation parameters define an instance of stimulation therapy (e.g., an electrical stimulation waveform to be generated by the neurostimulator and delivered through stimulation electrodes) and may include pulse amplitude, pulse frequency, inter-burst interval, pulse width, and burst duration.

One or both of the brain leads 2104, 2106 may have one or more physiological sensors 2110, 2116 that enable the capture and recording of other types of physiological information, e.g., pH levels, blood oxygen levels, neurotransmitters concentrations, heart rate, blood pressure, blood glucose levels, hormone levels, sleep states, posture, etc. To this end, one or both of the brain leads 2104, 2106 may be configured as disclosed in U.S. Pat. No. 10,123,717, entitled Multimodal Brain Sensing Lead, which is herein incorporated by reference, and the one or more physiological sensors 2110, 2116 may correspond to different transducers, e.g., macroelectrodes, microelectrodes, light emitters, and photodetectors that enable different sensing modalities.

The neurostimulator 2102 includes a memory subsystem 2138 and a central processing unit (CPU) 2140, which can take the form of a microcontroller. The memory subsystem 2138 is coupled to the detection subsystem 2126, and may receive and store records of data representative of sensed electrographic signals. The memory subsystem 2138 is also coupled to the therapy subsystem 2128 and the CPU 2140. In addition to the memory subsystem 2138, the CPU 2140 is also connected to the detection subsystem 2126 and the therapy subsystem 2128 for direct control of those subsystems.

The neurostimulator 2102 also includes a communication subsystem 2142. The communication subsystem 2142 enables communication between the neurostimulator 2102 and an external device, such as a programmer 216 or patient monitor 210, through a wireless communication link. As described above with reference to FIG. 2, the programmer 216 allows a clinician to read out records of patient data, as well as ancillary information associated with those records. The neurostimulator 2102 also includes a power supply 2144 and a clock supply 2146. The power supply 2144 supplies the voltages and currents necessary for each of the other subsystems. The clock supply 2146 supplies substantially all the other subsystems with any clock and timing signals necessary for their operation.

Building a Clinical Response Estimator

Figure 22A:
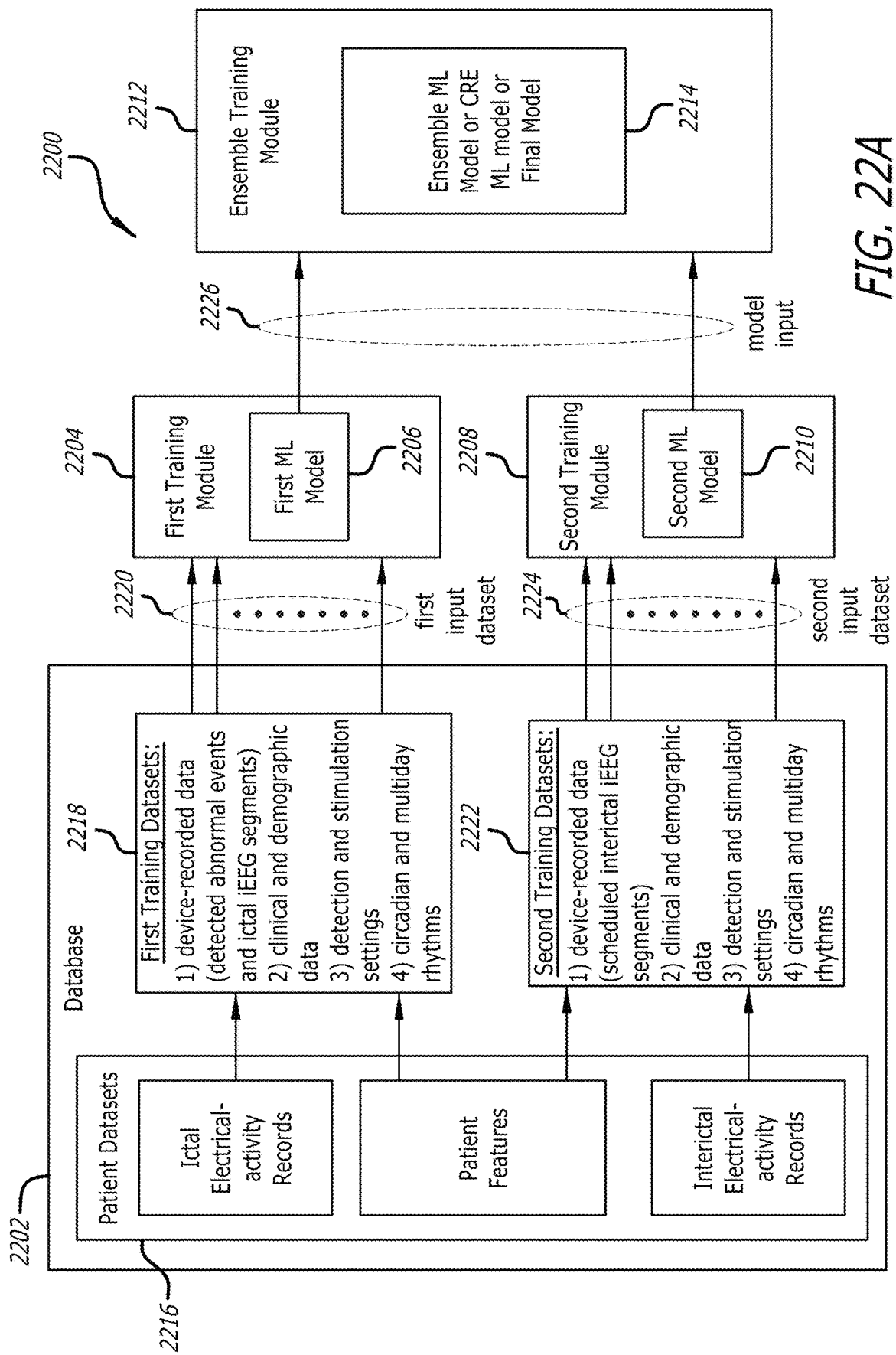
FIG. 22A is a block diagram of an architecture for producing a clinical response estimator having machine-learned CRE model (or ensemble model) configured to provide a CRE biomarker.

FIG. 22A is a block diagram of an architecture 2200 for building or producing a clinical response estimator having an ensemble machine-learned model (or CRE model or final model) configured to provide CRE biomarkers indicative of a patient's response to a treatment. For example, the treatment may relate to epilepsy and may comprise one or more of neurostimulation, drug therapy, or surgery. In the case of epilepsy, the CRE biomarker may provide an estimate of a patient's change in seizure frequency.

The architecture 2200 includes a database 2202 having information available for training, a first training module 2204 configured to train a first machine-learned model 2206, a second training module 2208 configured to train a second machine-learned model 2210, and an ensemble training module 2212 configured to generate an ensemble machine-learned model 2214. The training of these models 2204, 2208, 2214 involves aspects of supervised training/learning, and unsupervised, deep training/learning. The database 2202 includes patient datasets 2216 that include the information described earlier with reference to FIG. 1. The first machine-learned model 2206 and the second machine-learned model 2210 are trained on data from patient datasets 2216 across a patient population and are thus referred to herein at times, as "cross-patient" models. The ensemble machine-learned model is derived from the first cross-patient model and the second cross patient model and is thus referred to herein an ensemble model.

Figure 23:
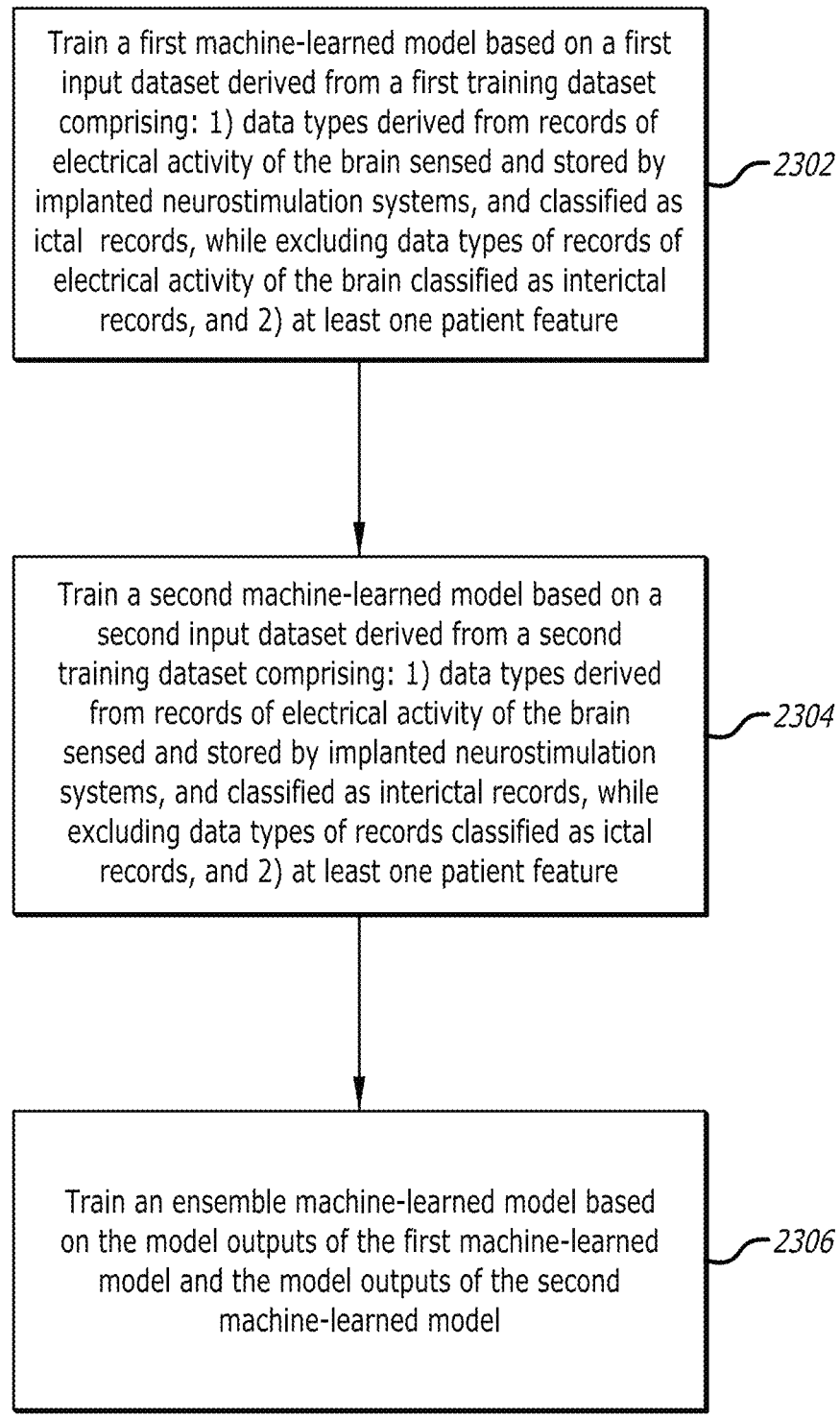
FIG. 23 is a flowchart of a method of producing a clinical response estimator for applying to a plurality of data inputs and at least one feature input to derive a CRE biomarker for a patient.

FIG. 23 is a flowchart of a method of producing a machine-learned clinical response estimator model (i.e., the ensemble machine-learned model 2214 in FIG. 22A) for applying to a plurality of model inputs to derive a clinical response estimate (CRE) biomarker for a patient. The method may be performed by the architecture 2200 of FIG. 22A.

At block 2302, a first machine-learned model 2206 is trained/produced based on a first input dataset 2220 derived from a first training dataset 2218 comprising: 1) data types derived from records of electrical activity of the brain sensed and stored by implanted neurostimulation systems, and classified as ictal records, while excluding data types of records of electrical activity of the brain sensed and stored by implanted neurostimulation systems and classified as interictal records, and 2) at least one patient feature. Details on the training of the first machine-learned model are provided below in the "First Machine-learned Model" section of this disclosure.

At block 2304, a second machine-learned model 2210 is trained/produced based on a second input dataset 2224 derived from a second training dataset 2222 comprising: 1) data types derived from records of electrical activity of the brain sensed and stored by implanted neurostimulation systems, and classified as interictal records, while excluding data types of records of electrical activity of the brain sensed and stored by implanted neurostimulation systems and classified as ictal records, and 2) at least one patient feature. Details on the training of the first machine-learned model are provided below in the "Second Machine-learned Model" section of this disclosure.

At block 2306, an ensemble machine-learned model 2214 is trained/produced based on the model outputs 2226 of the first machine-learned model 2206 and the model outputs of the second machine-learned model 2210. Details on the training of the ensemble machine-learned model are provided below in the "Ensemble Machine-learned Model (CRE Model)" section of this disclosure.

Training Models

One or more of the following types of supervised training/learning models and deep training/learning models (unsupervised) may be used to produce the first machine-learned model, the second machine-learned model, and the ensemble machine-learned model.

Partial Least Squares Regression (PLSR): By virtue of its computational efficiency, as well as its ability to achieve dimensionality reduction and model learning simultaneously, PLSR may be used. However, one limitation of PLSR is that it assumes a linear relationship. The relationships between RNS System data and changes in seizure frequency may not be linear. See Quigg, M. et al., Electrocorticographic events from long-term ambulatory brain recordings can potentially supplement seizure diaries. *Epilepsy Res* 161, 106302, (2020). As a result, models better suited to handle non-linear data, such as Random Forest Regression models may be used. The PLSR is a type of supervised training/learning model.

Random Forest Regression: This is an ensemble learning method for regression that constructs a multitude of decision trees at training time and outputs the mean prediction (regression) of the individual trees. Though random forest regression can capture non-linear relationships between input features and outputs, they are not able to extrapolate and understand growing/decreasing trends in data. As a result, they might need to be constantly updated and trained with random data that lies outside the range in the training dataset. Random forest regression is a type of supervised training/learning model Recurrent Neural Networks (RNNs): Long short-term memory (LSTM) subnetworks are designed to learn from sequence data, and thus are already designed to be able to incorporate cyclic information in features that result from daily and multi-day cycles, any lags between changes in features and the resulting changes in seizure rates, etc. These models effectively learn varying-length sequences and capture both short and long-range dependencies. The RNN is a type of deep training/learning model.

Transformers: Transformers are designed to learn from sequence data, and thus are already designed to be able to incorporate cyclic information in features that result from daily and multi-day cycles, any lags between changes in features and the resulting changes in seizure rates, etc. See Gorospe et al., A Generalization Performance Study Using Deep Learning Networks in Embedded Systems. *Sensors (Basel)* 21, (2021). These models effectively learn varying-length sequences and capture short, medium-range, and long-range dependencies. Additionally, transformers are much easier to train on standard deep learning hardware compared to other sequence models such as recurrent neural networks, since they process the sequence data in parallel by encoding the position of each time-step thus optimally utilizing the processing cores available in GPUs. Transformers may be used to recognize patterns in the device data in order to estimate relative change in seizure frequency. Transformers are a type of deep training/learning model.

Classification Models: As an alternative to regression models, classification models may be used. In this circumstance, the continuous output measure of seizure rate is replaced with bins of change in seizure rate. Bin sizes may be varied to achieve reasonably good performance accuracy with the highest bin resolution. Because of noise in patient self-reports, if including all bins does not lead to reliable model training, only bins corresponding to large changes in patient-reported seizure frequencies (e.g., >50% change) are used, since these are likely to contain more reliable patient-reported data than other bins.

Deep-learning Models: Deep-learning models may be used to train the second machine-learned model. Deep-learning models are used to train models without the need for feature extraction. These models include convolutional neural networks (CNN), which are a category of artificial neural networks that are suited for processing two-dimensional (2D) spatial data, and Recurrent Neural Networks (RNNs) that are suited for processing sequenced data analysis such as time-series, sentiment analysis, NLP, language translation, speech recognition, image captioning. One of the most common types of RNN model is Long Short-Term Memory (LSTM) network. The primary idea is to train two-dimensional filters to extract local features from EEG spectrograms in different level of hierarchies.

Hybrid CNN+LSTM: Modeling may be done with Hybrid CNN+LSTM models.

First Machine-Learned Model

Returning to block 2302 of FIG. 23, the first training module 2204 is configured to train the first machine-learned model 2206 based on a first training dataset 2218 that includes different data types and patient features from patient datasets across a patient population. The first training dataset 2218 includes different data types that are based on electrical activity of the brain sensed and stored by implanted neurostimulation systems and classified as ictal activity. For example, the first training dataset 2218 may include data types derived from EEG records comprising device-detected abnormal events and ictal EEG records. The first training dataset 2218 may also include a patient feature, such as a patient demographic, a patient characteristic, a device setting (detection or stimulation), and circadian and multiday rhythms. Excluded from the first training dataset 2218 is data types based on electrical activity of the brain classified as interictal.

Example of different data types and patient features that may be included in the first training dataset 2218 and in a first input dataset 2220 used by the first training module 2204 when training the first machine-learned model are listed in Table 3:

TABLE 3

| Model Input (Data Type/Feature) | Comments and Additional Information |
|---|---|
| long episode (LE) counts (e.g., daily count, multiday count), rate | Long episode events are known to covary with seizures. See Quigg, M. et al. |
| spike detection, abnormal pattern detection counts (e.g., daily count, multiday count), rate | Total number of detections may covary with seizures. |
| temporal information (e.g., lag between changes in LE counts/rates, spike count/rate, etc. and patient reported seizures) | Temporal information is incorporated into the regression models as described below in the Spearman Cross-Correlations - By First Training Module section of this disclosure. |
| type of activity patterns the implanted neurostimulator is configured to detect (e.g., e.g., delta activity, theta activity, interictal spiking activity, alpha activity, etc.) | Activity type is included even though the relationship between daily LE counts and patient-reported seizures is not influenced by the sensitivity of detection or by the type of activity being detected. See Quigg, M. et al. |
| circadian and multiday cycles in device-detected ictal activity (e.g., the time within the circadian and multidien cycle when the EEG was captured - for instance EEG was captured during the nighttime, or EEG was captured during the rising phase of the multidien cycle). | Circadian and multiday rhythms in device-detected interictal activity could be used to forecast seizure risk. See Baud, M. O. et al., Multi-day rhythms modulate seizure risk in epilepsy. Nat Commun 9, 88, (2018), and Karoly, P. J. et al. Forecasting cycles of seizure likelihood. Epilepsia 61, 776-786, (2020). Including these cycles in predictive models improve seizure forecasting. See Karoly, P. J. et al., The circadian profile of epilepsy improves seizure forecasting. Brain 140, 2169-2182, (2017). Morlet wavelet transform are used to identify the predominant periodicities, power, and phase of the hourly and daily interictal counts timeseries. These are incorporated into the regression models by inputting the phase of each cycle. For the RNNs, hour and day # are supplied as inputs so the model can learn these cycles implicitly. For example, the raw data are a time series, for example, hourly counts of detection episodes (aka, detections, or episodes) made by the neurostimulator. Circadian phase can be defined relative to daily maxima and minima in the hourly counts. Multidien (aka, multiday) phase can also be defined relative to the local maxima and minima in the multidien waveform extracted by the Morlet wavelet transform, or low-pass filtering the signal, or other phase-extraction methods. |
| proportion of LE-EEG records containing electrographic seizures (e.g., proportion of the total daily LE-EEG records classified as ictal) | The proportion of LE-EEG records that contained electrographic seizures influence the strength of the correlation between counts of detected LEs and seizures, such that higher proportions are associated with stronger correlations. See Quigg, M. et al. To efficiently extend the analysis to a larger patient population, a developed cross-patient EEG segment classifier may be employed to classify the LE-EEG records as ictal or not ictal. See Barry et |

TABLE 3-continued

| Model Input (Data Type/Feature) | Comments and Additional Information |
|---|---|
| | al., A High Accuracy Electrographic Seizure Classifier Trained Using Semi-Supervised Labeling Applied to a Large Spectrogram Dataset, Frontiers in Neuroscience, Vol. 15, pgs. 1-20, Jun. 28, 2021. |
| electrographic seizure morphology (e.g., seizure onset type, predominant frequencies, and seizure offset. Seizure onsets may include low-voltage fast or abrupt high-voltage beta oscillation or high amplitude beta type. Predominant frequencies may include gamma or beta or a progression from low voltage gamma to high voltage beta. Seizure offsets may include an abrupt transition to baseline, or alternation between high-amplitude spiking and very low amplitude EEG.) | A deep-learning model may be used to identify patients with similar electrographic seizure morphologies. See U.S. Pat. No. 10/729,907. |
| relative change in data type counts, measures, identifications in adjacent time windows (e.g., features extracted from EEG data such as total spectral power or power in specific frequency bands such as delta, theta, alpha, beta, and gamma. Features may also include spike rate or seizure morphology) | |
| device stimulation settings (e.g., current amplitude, pulse width, frequency, and burst duration) | Different stimulation settings can have different neuromodulatory effects. Example: low frequency stimulation can have an entraining effect, and high frequency stimulation can have a desynchronizing activity. So, passing in the stimulation settings to the model may improve the model's performance. |
| device detector (e.g., half wave, line length, and area under the curve)/detection type (e.g., delta activity detected, theta activity detected) | Using a simplified categorical description of what the detector is detecting provides better model explainability. |
| device detection settings (e.g., parameters for line length, bandpass, and area under the curve device detectors) | Using detection settings may provide better model performance. |
| clinical characteristics (e.g., the region of seizure onset, anatomical MRI abnormalities, lead location, age of onset, duration of epilepsy, and whether the patient had a prior resection or a vagal nerve stimulator, patient reported seizures) | Brain activity patterns may depend on these inputs. For example, in Nune et al., 2019 we have shown that patients with PVNH - a type of brain abnormality - have a specific type of electrographic seizures. So, feeding in the anatomical abnormality to the model may improve the model's predictions. |

The different data types may also be partially based on ictal electrical activity of the brain that is sensed and stored by an external neurostimulation system using scalp electrodes. In cases where EEG records resulting from intracranial sensing of ictal electrical activity and EEG records resulting from external scalp electrodes are used, data processing steps include: (1) skipping the stimulation artifact rejection step for both datasets and (2) for the data types based on external EEG records, applying a 60 Hz denoising notch filter to the raw timeseries data of external EEG record before the spectrograms are created since 60 Hz noise is commonly present in EEG data. In addition, for models that include device count data as inputs, the data of the external EEG record are passed through a benchtop system running the types of detectors that the implantable neurostimulation systems run.

The different data types and patient features may be used "as is" during model training. The different data types and patient features may be manipulated or transformed from the "as is" state during model training. Generally, EEG records are transformed—filtered in some way, or passed through machine or deep learning models. Patient clinical characteristics are least likely to be transformed. But they can also be transformed through, for example, a combining operation as earlier described.

Spearman Cross-Correlations—by First Training Module

In some embodiments Spearman cross-correlations are used to determine if there are monotonic relationships between data types (e.g., LE counts, interictal spike rate and spectral power features) based on EEG records of a patient and a clinical characteristic of the patient (e.g., patient-reported seizures) within a window time from a clinical event. Monotonic in this context means a scenario in which the size of one variable increases as the other variables also increases, or where the size of one variable increases as the other variable also decreases. An example window of time is ±14 days. The clinical event may be, for example, a clinical seizure. One example is that clinical seizures and long episodes have a monotonic relationship. So, when one increases, the other also increases. Another example could be that the proportion of episode durations exceeding a threshold increases as clinical seizures increases.

The Spearman cross-correlations analysis not only indicates if a significant relationship exists between data types (e.g., LE counts, interictal spike rate and spectral power features) based on EEG records of a patient and a clinical characteristic of the patient (e.g., patient-reported seizures), but also indicates useful temporal information, such as a time of occurrence of a change in a device-recorded data type relative to changes in seizure frequency. For example, the Spearman cross-correlation may indicate if a change in a device-recorded data type occurred before, after or coincident with changes in seizure frequency. The existence of a significant may be quantified as a p-value as determined by the Spearman cross-correlation, which value may be an input in model training.

In the case of regression models (e.g., PLSR model or random forest regression models), this temporal information is incorporated into the regression models by explicitly offsetting the inputs from the outputs at the best lags, which improves model estimates. For example, if a Spearman cross-correlation reveals that the LE rate increases 4 days prior to seizure rate increase, then when building the PLSR to predict the seizure rate on day 0, the LE rate from 4 days prior is used as an input for model training. In another example, if an increase in episode duration always precedes a seizure by a day, offsetting the timestamps of the episode durations by one day (adding a day) would make them vary together in time. In the case of RNN models, these explicit corrections are not performed. Instead, the RNN models incorporate LSTMs, which are expected to capture those lags implicitly.

This temporal information may be used to: 1) improve the first machine-learned model 2206 by temporally offsetting data types included in the first input dataset 2220 corresponding to the data types in the cross-patient models; and 2) inform model hyperparameters such as window length. In machine learning model training, there are several variables that are user-selected as part of the model training process. These variables are called hyperparameters. If the Spearman cross-correlation determines that the LE rate for example changes 15 days prior to the seizure rate change, then a window that is at least 15 days in length (the window length being a hyperparameter that is user selected) is used when training machine learning models. That is, the LE rate data from that 15-day window is used.

Second Machine-Learned Model

Returning to block 2304 of FIG. 23, the second training module 2208 is configured to train the second machine-learned model 2210 based on a second training dataset 2222 that includes different data types and patient features from patient datasets across a patient population. The second training dataset 2222 includes a different data types that are based on electrical activity of the brain sensed and stored by implanted neurostimulation systems and classified as interictal activity. For example, the second training dataset 2222 may include data types derived from EEG records comprising scheduled EEG records corresponding to interictal EEG records. The second training dataset 2222 may also include a patient feature, such as a patient demographic, a patient characteristic, a device setting (detection or stimulation), and circadian and multiday rhythms. The different data types may also be partially based on interictal electrical activity of the brain that are sensed and stored by an external neurostimulation system. Excluded from the second training dataset 2222 is data types based on electrical activity of the brain classified as ictal.

Regarding scheduled EEG records, while a limited amount of EEG activity is stored on an implanted neurostimulation system between downloads due to storage limitations, the timeseries data provided in the scheduled-EEG records represent a potentially richer data set than device event counts. Even though recorded scheduled-EEG records are discontinuous, interictal spike rates and interictal spectral power from these recordings can be used to accurately classify whether the patients are in the upper vs. lower quartiles of clinical response to responsive stimulation therapy. See Desai et al., Quantitative electrocorticographic biomarkers of clinical outcomes in mesial temporal lobe epileptic patients treated with the RNS system, Clinical Neurophysiology 130 (2019) 1364-1374. Furthermore, deep learning models can use spectral images of the interictal scheduled-EEG records to accomplish the same task without predefining features of interest. See Desai et al., Transfer-learning for differentiating epileptic patients who respond to treatment based on chronic ambulatory ECoG data, 9th International IEEE/EMBS Conference on Neural Engineering (NER), San Francisco, CA, USA, Mar. 20-23, 2019. pages 1-4, IEEE, 2019.

Example of different data types and patient features that may be included in the second training dataset 2222 and included in a second input dataset 2224 used by the second training module 2208 when training the second machine-learned model 2210 are listed in Table 4:

TABLE 4

| Model Input (Data Type/Features) | Comments and Additional Information |
| --- | --- |
| hand-engineered features of interest extracted from interictal EEG records (e.g., spike rate or spectral power) | Machine-learning models incorporate hand-engineered features extracted from interictal EEG records. The hand-engineered features are used to train PLSR and Random Forest Regression models. Features like delta power, theta power are defined by the user and are called hand-engineered. In case of deep learning model training, generally the user will not design features, the model takes raw data and figures out the relevant features as part of model training. |
| hand-engineered features - across multiple channels per interictal EEG record (e.g., average/median/maximum/minimum spike rate or spectral power across two or all four channels, or calculating cross-channel coherence across a range of frequencies for every combination of two channels.) | Hand-engineered features may be aggregated across channels to attain one value per segment. |

TABLE 4-continued

| Model Input (Data Type/Features) | Comments and Additional Information |
| --- | --- |
| temporal information (e.g., lag between changes in hand-engineered data types and patient reported seizures) | Temporal information is incorporated into the regression models as describe below in the Spearman Cross-Correlations - By Second Training Module section of this disclosure. |
| interictal spike rate (e.g., number of spikes detected in EEG record divided by the duration of the record | The interictal spike rate can be used to classify high vs. low clinical response in MTLE patients. See Desai et al., Quantitative electrocorticographic biomarkers of clinical outcomes in mesial temporal lobe epileptic patients treated with the RNS system, Clinical Neurophysiology 130, 1364-1374, (2019). |
| interictal spectral power (e.g., total interictal gamma power, total interictal delta power, total interictal theta power, (across all frequencies) as well as within specific frequency bands including delta, theta, alpha, beta, and gamma, usually calculated for each channel, but can be averaged across channels as well) | The interictal gamma power can be used to classify high vs low clinical response in patients with seizures arising from the neocortex. |
| coherence (e.g., cross channel coherence; coherence value may be a normalized value, wherein if the value is 1, there is 100% coherence, and if 0, there is no coherence) | Changes in coherence across channels of EEG can be used to identify changes in a patient's ASMs. See Meisel et al., Intrinsic excitability measures track antiepileptic drug action and uncover increasing/decreasing excitability over the wake/sleep cycle. Proc Natl Acad Sci USA 112, 14694-14699, (2015). |
| autocorrelation and variance (e.g., a variance value, such 5) | Within channel signal autocorrelation, variance, and interictal spike rates can reliably forecast seizure risk. See Maturana, et al., Critical slowing down as a biomarker for seizure susceptibility. Nat Commun 11, 2172, (2020). |
| entropy in the raw EEG signals (e.g., an entropy value, such as 10) | Entropy provides information about seizure rates. See Uriguen et al., Comparison of background EEG activity of different groups of patients with idiopathic epilepsy using Shannon spectral entropy and cluster-based permutation statistical testing. PLoS One 12, (2017). |
| skewness in the raw EEG signals (e.g., a skewness value, such a 2) | Skewness provides information about seizure rates. See Mooij et al., A skew-based method for identifying intracranial EEG channels with epileptic activity without detecting spikes, ripples, or fast ripples. Clin Neurophysiol 131, 183-192, (2020). |
| rate of zero-crossings in the raw EEG signals (e.g., a number of crossing per time period, such as five zero crossing in 1 second) | Rate of zero-crossing provides information about seizure rates. |
| spectral and time-series images (e.g., spectral transformations of the timeseries data and/or raw timeseries data) | For deep learning models. |
| circadian and multiday cycles in device-detected interictal activity (e.g., the time within the circadian and multidien cycle when the EEG was captured - for instance EEG was captured during the nighttime, or EEG was captured during the rising phase of the multidien cycle). | Circadian and multiday rhythms in device-detected interictal activity could be used to forecast seizure risk. See Baud, et al., and Karoly, et al., Forecasting cycles of seizure likelihood. Epilepsia 61, 776-786, (2020). Including these cycles in predictive models improve seizure forecasting. See Karoly, P. J. et al. The circadian profile of epilepsy improves seizure forecasting. Brain 140, 2169-2182, (2017). Morlet wavelet transform are used to identify the predominant periodicities, power, and phase of the hourly and daily interictal counts timeseries. These are incorporated into the regression models by inputting the phase of each cycle. For the RNNs, hour and day # are supplied as inputs so the model can learn these cycles implicitly. For example, the raw data are a time series, for example, hourly counts of detection episodes (aka, detections, or |

TABLE 4-continued

| Model Input (Data Type/Features) | Comments and Additional Information |
| --- | --- |
| | episodes) made by the neurostimulator. Circadian phase can be defined relative to daily maxima and minima in the hourly counts. Multidien (aka, multiday) phase can also be defined relative to the local maxima and minima in the multidien waveform extracted by the Morlet wavelet transform, or low-pass filtering the signal, or other phase-extraction methods. |
| electrographic seizure morphology (e.g., seizure onset type, predominant frequencies, and seizure offset. Seizure onsets may include low-voltage fast or abrupt high-voltage beta oscillation or high amplitude beta type. Predominant frequencies may include gamma or beta or a progression from low voltage gamma to high voltage beta. Seizure offsets may include an abrupt transition to baseline, or alternation between high-amplitude spiking and very low amplitude EEG.) | A deep-learning model may be used to identify patients with similar electrographic seizure morphologies. See U.S. Pat. No. 10/729,907. |
| device stimulation settings (e.g., current amplitude, pulse width, frequency, and burst duration) | Different stimulation settings can have different neuromodulatory effects. Example: low frequency stimulation can have an entraining effect, and high frequency stimulation can have a desynchronizing activity. So, passing in the stimulation settings to the model may improve the model's performance. |
| device detector (e.g., half wave, line length, and area under the curve)/detection type (e.g., delta activity detected, theta activity detected) | Using a simplified categorical description of what the detector is detecting provide better model explainability. |
| device detection settings (e.g., parameters for line length, bandpass, and area under the curve device detectors) | Using detection settings may provide better model performance. |
| clinical characteristics (e.g., the region of seizure onset, anatomical MRI abnormalities, lead location, age of onset, duration of epilepsy, and whether the patient had a prior resection or a vagal nerve stimulator) | Brain activity patterns may depend on these inputs. For example, in Nune et al., 2019 we have shown that patients with PVNH - a type of brain abnormality - have a specific type of electrographic seizures. So, feeding in the anatomical abnormality to the model may improve the model's predictions. |

Spearman Cross-Correlations—by Second Training Module

In some embodiments Spearman cross-correlations are used to determine if there are monotonic relationships between hand-engineered data types (e.g., spike rate or spectral power) based on EEG records of a patient and a clinical characteristic of the patient (e.g., patient-reported seizures) within a window time from a clinical event. Monotonic in this context means a scenario in which the size of one variable increases as the other variables also increases, or where the size of one variable increases as the other variable also decreases. An example window of time is ±14 days. The clinical event may be, for example, a clinical seizure. One example is that clinical seizures and long episodes have a monotonic relationship. So, when one increases, the other also increases. Another example could be that the proportion of episode durations exceeding a threshold increases as clinical seizures increases.

The Spearman cross-correlations analysis not only indicates if a significant relationship exists between hand-engineered data types (e.g., spike rate or spectral power) based on EEG records of a patient and a clinical characteristic of the patient (e.g., patient-reported seizures), but also indicates useful temporal information, such as a time of occurrence of a change in a device-recorded data type relative to changes in seizure frequency. For example, the Spearman cross-correlation may indicate if a change in a device-recorded data type occurred before, after or coincident with changes in seizure frequency. The existence of a significant may be quantified as a p-value as determined by the Spearman cross-correlation, which value may be an input in model training.

In the case of regression models (e.g., PLSR model or random forest regression models), this temporal information is incorporated into the regression models by explicitly offsetting the inputs from the outputs at the best lags, which improves model estimates. For example, if a Spearman cross-correlation reveals that the LE rate increases 4 days prior to seizure rate increase, then when building the PLSR to predict the seizure rate on day 0, the LE rate from 4 days prior is used as an input for model training. In another example, if an increase in episode duration always precedes a seizure by a day, offsetting the timestamps of the episode durations by one day (adding a day) would make them vary together in time. In the case of RNN models, these explicit corrections are not performed. Instead, the RNN models incorporate LSTMs, which are expected to capture those lags implicitly.

This temporal information may be used to: 1) improve the training of the second machine-learned model 2210 by temporally offsetting data types included in the second input dataset 2224 corresponding to the data types in the cross-patient models; and 2) inform model hyperparameters such as window length. For example, for cross-correlation analyses using hand-engineered interictal EEG data types (such as spike rate or spectral power), data types may be aggregated across channels to obtain a single value per EEG segment and weighting may be used to account for differing amounts of data available per patient.

The different data types may also be partially based on interictal electrical activity of the brain that are sensed and stored by an external neurostimulation system using scalp electrodes. In cases where EEG records resulting from intracranial sensing of ictal electrical activity and EEG records resulting from external scalp electrodes are used, data processing steps include: (1) skipping the stimulation artifact rejection step for both datasets and (2) for the data types based on external EEG records, applying a 60 Hz denoising notch filter to the raw timeseries data of external EEG record before the spectrograms are created since 60 Hz noise is commonly present in EEG data. In addition, for models that include device count data as inputs, the data of the external EEG record are passed through a benchtop system running the types of detectors that the implantable neurostimulation systems run.

Figure 24:
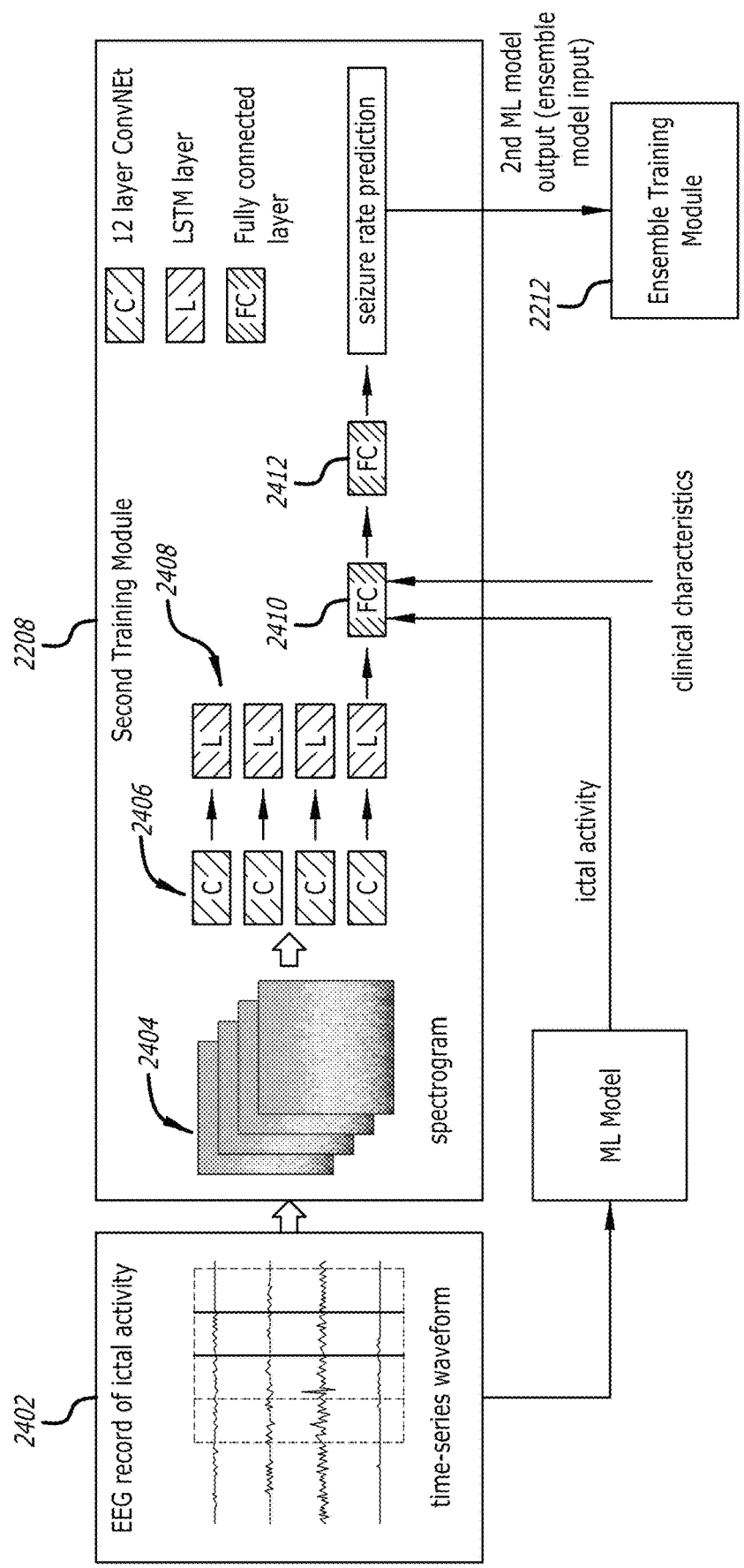
FIG. 24 is a schematic of a hybrid CNN+LSTM model architecture.

With reference to FIG. 24, in some embodiments a hybrid CNN+LSTM model architecture is used to generate model inputs that are used to train the ensemble machine-learned model. CNNs are sensitive to the length of EEG files used for training. The addition of the LSTM layer to the CNNs facilitates the analysis of EEG records of varying lengths, thus eliminating a preprocessing step converting all records to a fixed length. Starting from the left side of FIG. 24, and with additional reference to FIG. 22A, an EEG record 2402 of ictal activity is obtained from a patient dataset 2216 and included in a second input dataset 2224 used by the second training module 2208 to generate a model input. The second training module 2208 is configured to convert each channel of the EEG record 2402 into a spectrogram 2404. The spectrograms 2404 are then passed into a second ML model that includes a 12-layer CNN 2406. Respective features generated by the 12-layer CNN 2406 then enter an LSTM layer 2408 and subsequently two fully connected layers 2410, 2412. Additional data types and patient features included in the second input dataset 2224 are included as embeddings in the first fully connected layer 2410. Additional data types may include electrographic seizure morphologies obtained from an ML model that determines type of ictal activity. The patient features may include one or more clinical characteristics.

Data Modifications

EEG records included in a patient dataset may include date for each of four sensing channels of an implanted neurostimulation system.

Missing channels: Vectors of zeros may be substituted for missing channels in an EEG record.

Data down sampling: With reference to FIG. 22A, the patient datasets 2216 from which the first input dataset 2220 for the first training module 2204 and the second input dataset 2224 for the second training module 2208 are obtained may be from patients having differing amounts of EEG records. Data from patients with higher amounts of EEG records may be randomly down sampled, so their data does not overly influence the models. Alternatively, weighting may also be used to account for patient differences in data availability.

Data augmentation: Data augmentation may be done by swapping the order of the channels within leads and the order of the leads within the input images (spectrograms or timeseries). This produces more input data potentially improving model performance and reduces the dependence of the models on channel order. Data augmentation means making more training data than actually available. This can be done by manipulating the training data to create additional training data. For example, since there are generally 4 channels of data in an EEG record, a "new" EEG record may be created by changing the ordering of channels in the record. So, if the original EEG record has 4 channels of data (channels 1, 2, 3, 4) then the "new" EEG record can have channels in the other combinations (example 2, 3, 1, 4 or 4, 2, 3, 1 etc.).

Windowing

Figure 25A:
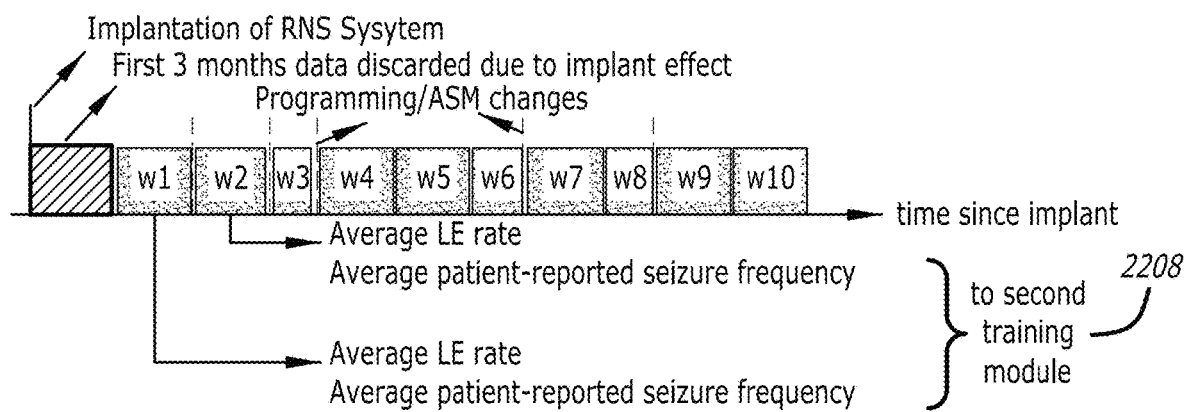
FIGS. 25A, 25B, and 25C illustrate a windowing method employed during model training to account for changes in model inputs that may occur over time.
Figure 25B:
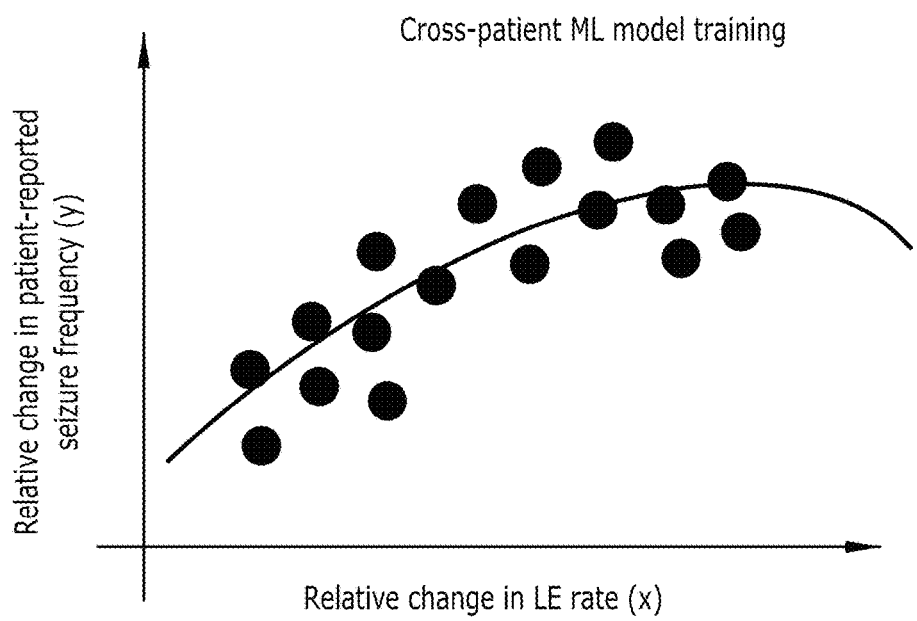
Figure 25C:
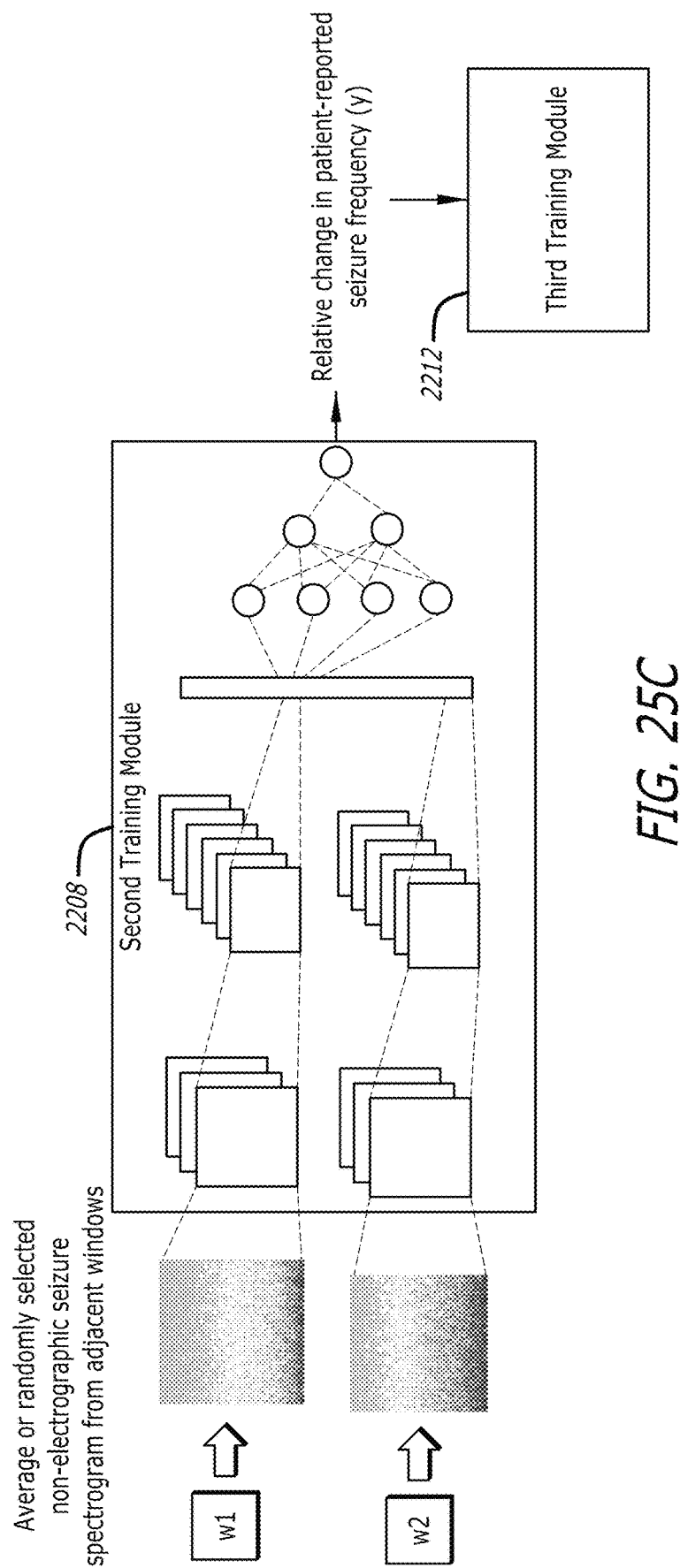

With reference to FIG. 25A-25C, a windowing method may be employed during model training to account for changes in model inputs that may occur over time due to an event of interest. An event may be the start of a new antiepileptic drug, or a change in stimulation parameters, for example. The window may be a month before vs a month after the event. Other window sizes such as 1 week or 2 weeks may be used. In some contexts, the windows are as short as possible but still long enough to observe a meaningful change in the clinical response between the two windows. In the case of a CRE model being trained to provide CRE biomarkers indicative of relative change in seizure frequency, the model inputs during training may consist of relative change in data type values (e.g., counts, measures, rates, etc.) and patient feature values (e.g., patient reported seizure frequency) in adjacent time windows.

With reference to FIG. 25A, ten time windows (w1 through w10) associated with an implanted neurostimulation system that provides datasets of a patient are shown. Data type values and patient features values from one or more of the ten windows may be used for training. Data type and patient features values in the first three months after implant are discarded due to implant effect. Following the first three months, average data type and patient feature values are computed between: 1) adjacent event epochs separated by an event of interest, e.g., a change in device programming or a change or new antiseizure medication (ASM), or 2) between adjacent windows of a select duration, e.g., 1-3 month. For example, the result of a Spearman output of spearman cross-correlation may inform the size of window used for model training. Relative changes in computed average data type values between adjacent epochs or adjacent windows are computed. The associated relative change in patient-reported seizure rates during the adjacent epochs or adjacent windows are also computed and used as the target for model training and validation. FIG. 25B is a graph illustrating relative change in patient-reported seizure frequency as a function of relative change in LE rate.

When more than one type of detected activity (e.g., delta activity detected by a delta detector, theta activity detected by a theta detector, etc.) is included in the dataset of a patient, a change in detection counts for each type of detector may be used as model input. In the case of epochs separated by a device programming change, abnormal events and detection counts are normalized across programming epochs by computing the change in detection rates in ictal and interictal EEG records captured in each patient with the old and new programming epochs. For example, if the old detector settings produce 80 detections on ten stored ictal and interictal EEG records in a patient, and the new detector settings produce 100 detections, the daily detection counts in the new programming epoch are scaled by a factor of 8/10 to normalize it to the sensitivity levels of the old detectors.

FIG. 25C is an example second machine-learned model 2210 having a CNN architecture for predicting relative change in seizure frequency between two adjacent time windows. In this example, data types corresponding to spectrograms and coherograms computed from scheduled EEG records are included in a second input dataset 2224 for a second training module 2208 that generates the second machine-learned model 2210. In some embodiments, random non-seizure EEG records are selected from each of the time windows (w1 through w10) for training the CNN. Alternatively, the average spectrogram in each time window may be included in a second input dataset 2224 for training the CNN. In this case, the average spectrogram within each time window, or a randomly selected spectrogram from each time window, are used as inputs to the CNN. The CNN is trained to identify changes in the spectrograms and predict the change in seizure frequency.

Due to anticipated long-term plasticity changes in electrical activity of the brain, in some embodiments only feature and seizure frequency differences in adjacent windows are included in the second input dataset 2224 for training the second machine-learned model 2210. However, in cases where there are insufficient adjacent windows for computing training data, relative changes in features and patient reported seizure frequency from non-adjacent windows can be used for augmenting the training dataset.

Ensemble Machine-Learned Model (CRE Model)

Returning to block 2306 of FIG. 23, and with additional reference to FIG. 22A, the ensemble machine-learned model 2214 is trained/produced based on the model outputs of the first machine-learned model 2206 and the model outputs of the second machine-learned model 2210. The ensemble machine-learned model 2214 may be a stacked model, e.g., linear regression or shallow neural networks, trained by the ensemble training module 2212 based on the model inputs 2226 fed to the ensemble training module by the first machine-learned model 2206 and the second machine-learned model 2210. Additional machine-learned models or a variation of the first and second machine-learned models may be included to provide model inputs 2226. For example, scheduled EEG records may be used to train the second machine-learned model 2210, while ictal values/counts (LE counts, detection counts, etc.) may be used to train the first machine-learned model 2206. A third machine-learned model (not shown) may be trained on a subset of ictal datasets and scheduled EEG records. A fourth machine-learned model (not shown) may be trained on only the demographic features. The outputs of all of these individually trained models are fed into the ensemble training module 2212 to train the ensemble machine-learned model 2214.

Figures 22B, 22C:
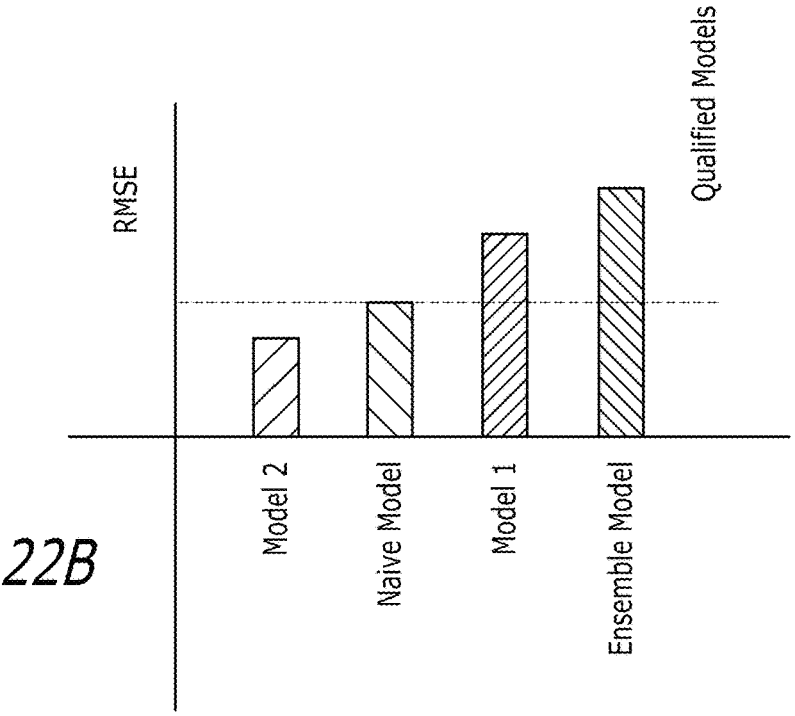
FIG. 22B is a graph of model quantifications of various machine-learned models included in the architecture of FIG. 22A.
FIG. 22C is a table showing an example of data type importance for a qualified CRE model.

With reference to FIG. 22B, each of the first machine-learned model, the second machine-learned model, and the ensemble machine-learned model is evaluated by comparing the model estimate of changes in seizure frequency with the relative changes in patient-reported seizure frequency. For each model, the Root Mean Square Error (RMSE) is calculated as the standard deviation of the residuals (model estimates versus patient-report). The RMSE for the models is compared to the RMSE for naïve models. Naïve models provide outcome estimates based solely on the distribution of the training data. Their outputs are simply the most frequent (mode) value in the training dataset. Significant differences between the real models and naïve models are determined using Wilcoxon Rank Sum with p=0.05.

FIG. 22C is a table showing an example of feature importance for a qualified CRE biomarker model. CRE biomarkers are identified by determining the importance of each EEG feature (e.g., model input) to the ensemble machine-learned model. Due to the large volume of training data, the trained model associates higher weights to relevant input features without overfitting to irrelevant features. The amount that each feature contributes to a CRE biomarker is not simply determined by the weights assigned by a model since that does not account for interdependencies between the different features. As a result, the "importance" of each feature is measured by using two complementary approaches: permuting feature values, and recursive feature elimination.

Permuting feature values calculates the change in the model's prediction error (RMSE) after shuffling the feature values. A feature is "important" if shuffling its values increases the model error, because in this case the model relied on the feature. A feature is "unimportant" if shuffling its values leaves the model error unchanged, because in this case the model ignored the feature. See Uriguen et al., Comparison of background EEG activity of different groups of patients with idiopathic epilepsy using Shannon spectral entropy and cluster-based permutation statistical testing. PLoS One 12, e0184044, (2017). Similarly, recursive feature elimination tests the "importance" of a feature by calculating the model's prediction error when that feature is held out. See Mooij et al.

If any of the "important" features are features identified by deep-learning algorithms, saliency maps are used to visualize the features. Saliency maps are computed as the gradient of the output with respect to the input, and highlight the input regions in the datasets that contribute most towards the output. See Si, K. et al. Fully end-to-end deep-learning-based diagnosis of pancreatic tumors. Theranostics 11, 1982, (2021). These maps are used to make sure the biomarkers found are not spurious EEG features (such as the length of EEG files, signal baselines, or some other device-induced artifact). This process will define the CRE biomarker used by each model to estimate changes in seizure frequency.

The clinical response estimator model may be too complex for on-board implementation in an implantable neurostimulation system. For example, many deep learning models require intense processing power, often relying on graphic processing units (GPUs), to conduct training and inference. Running a deep learning model on-board implementation in an implantable neurostimulation system, which has less powerful processing chips and storage space may be a challenge. According, a simple linear model may be implemented. For example, the clinical response estimator model resulting from the process of FIG. 23, may be simplified by converting the model using TensorFlow lite with the goal of reducing file size without impacting accuracy. See Vaswani, A. et al. Attention is all you need. Advances in neural information processing systems 30 (2017).

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of controlling operation of an implanted neurostimulation system configured to sense episodes of electrographic events and determine durations of episodes, the method comprising:
    mapping durations of electrographic events sensed by the implanted neurostimulation system with seizure probability biomarkers derived from records of the electrographic events to create a mapping function; and
    for each of one or more operations of the implanted neurostimulation system:
        selecting a seizure probability biomarker having a value desired for the operation,
        selecting a duration mapped to the selected seizure probability biomarker, and
        programming the duration into a control module of the implanted neurostimulation system as a programmed parameter that triggers the operation by the implanted neurostimulation system.

2. The method of claim 1, wherein the duration is a sole parameter that triggers the operation.

3. The method of claim 1, wherein a machine-learned model is applied to each record included in the records of the electrographic events to derive a seizure probability biomarker for each record.

4. The method of claim 3, wherein the machine-learned model is a deep learning model.

5. The method of claim 3, wherein the records of electrographic events correspond to ictal events.

6. The method of claim 1, wherein the operation is a detection of an ictal electrographic event, and the operation is triggered in response to the duration of a sensed episode exceeding the programmed parameter.

7. The method of claim 1, wherein the operation is a storing of a date/time of a sensed episode, and the operation is triggered in response to the duration of the sensed episode exceeding the programmed parameter.

8. The method of claim 1, wherein the operation is a storing of record of a sensed episode, and the operation is triggered in response to the duration of the sensed episode exceeding the programmed parameter.

9. The method of claim 1, wherein the operation is a delivery of stimulation therapy, and the operation is triggered in response to the duration of a sensed episode exceeding the programmed parameter.

10. The method of claim 1, wherein the operation is an output of a warning, and the operation is triggered in response to the duration of a sensed episode exceeding the programmed parameter.

11. The method of claim 1, further comprising providing the mapping function to the implanted neurostimulation system.

12. An apparatus for controlling operation of an implanted neurostimulation system configured to sense episodes of electrographic events and determine durations of episodes, the apparatus comprising:
    a memory having a plurality of modules; and
    a processor coupled to the memory, and configured to execute operations based on the plurality of modules to:
        map durations of electrographic events sensed by the implanted neurostimulation system with seizure probability biomarkers derived from records of the electrographic events; and
        for each of one or more operations of the implanted neurostimulation system:
            select a seizure probability biomarker having a value desired for the operation,
            select a duration mapped to the selected seizure probability biomarker, and
            program the duration into a control module of the implanted neurostimulation system as a programmed parameter that triggers the operation by the implanted neurostimulation system.

13. A method of operation of an implanted neurostimulation system of a patient, the method comprising:
    detecting an electrographic event;
    determining a duration of an episode of the electrographic event;
    comparing the episode duration to a threshold duration; and
    initiating an operation of the implanted neurostimulation system solely in response to the episode duration satisfying the threshold duration;
    wherein the threshold duration corresponds to one of a plurality of threshold durations, each threshold duration associated with a different seizure probability biomarker by a mapping function.

14. The method of claim 13, wherein the operation is a detection of an ictal electrographic event, and the operation is initiated in response to the episode duration exceeding the threshold duration.

15. The method of claim 13, wherein the operation is a storing of a date/time of the episode of the electrographic event, and the operation is initiated in response to the episode duration exceeding the threshold duration.

16. The method of claim 13, wherein the operation is a storing of a record of the episode of the electrographic event, and the operation is initiated in response to the episode duration exceeding the threshold duration.

17. The method of claim 13, wherein the operation is a delivery of stimulation therapy, and the operation is initiated in response to the episode duration exceeding the threshold duration.

18. The method of claim 13, wherein the operation is an output of a warning, and the operation is initiated in response to the episode duration exceeding the threshold duration.

19. An implantable neurostimulation system comprising:
    a detection subsystem;
    a therapy subsystem;
    a memory having a plurality of modules; and
    a processor coupled to the memory, the detection subsystem, and the therapy subsystem, and configured to execute operations based on the plurality of modules to:
        detect an electrographic event through the detection subsystem,
        determine a duration of an episode of the electrographic event,
        compare the episode duration to threshold duration, and
        initiate an operation of the implanted neurostimulation system solely in response to the episode duration satisfying the threshold duration, wherein the threshold duration corresponds to one of a plurality of threshold durations, each threshold duration associated with a different seizure probability biomarker.

* * * * *